(12) United States Patent
Kitazawa et al.

(10) Patent No.: US 8,558,108 B2
(45) Date of Patent: Oct. 15, 2013

(54) ELECTRON DONATING MATERIAL, MATERIAL FOR PHOTOVOLTAIC DEVICES AND PHOTOVOLTAIC DEVICE

(75) Inventors: Daisuke Kitazawa, Otsu (JP); Shuhei Yamamoto, Otsu (JP); Jun Tsukamoto, Otsu (JP)

(73) Assignee: Toray Industries, Inc. (JP)

( * ) Notice: Subject to any disclaimer, the term of this patent is extended or adjusted under 35 U.S.C. 154(b) by 375 days.

(21) Appl. No.: 12/936,061

(22) PCT Filed: Mar. 13, 2009

(86) PCT No.: PCT/JP2009/054836
§ 371 (c)(1),
(2), (4) Date: Oct. 1, 2010

(87) PCT Pub. No.: WO2009/125647
PCT Pub. Date: Oct. 15, 2009

(65) Prior Publication Data
US 2011/0023964 A1 Feb. 3, 2011

(30) Foreign Application Priority Data

Apr. 11, 2008 (JP) ................................. 2008-103205
Oct. 22, 2008 (JP) ................................. 2008-271688

(51) Int. Cl.
*H01L 31/00* (2006.01)
*C08G 75/32* (2006.01)

(52) U.S. Cl.
USPC .......................................... 136/263; 528/380

(58) Field of Classification Search
None
See application file for complete search history.

(56) References Cited

U.S. PATENT DOCUMENTS

| | | |
|---|---|---|
| 2004/0115473 A1 | 6/2004 | Burroughes et al. |
| 2006/0052612 A1 | 3/2006 | Stossel et al. |
| 2006/0174937 A1 | 8/2006 | Zhou |

FOREIGN PATENT DOCUMENTS

| | | |
|---|---|---|
| JP | 2003-104976 | 4/2003 |
| JP | 2003-347565 | 12/2003 |
| JP | 2004-165474 | 6/2004 |
| JP | 2004-534863 | 11/2004 |
| JP | 2006-222429 | 8/2006 |

OTHER PUBLICATIONS

Li et al., "Synthesis of a benzothiadiazole/thiophene-based oligomer for bulk heterojunction photovoltaic cells," Synth. Met. 159 (2009) 201-208.*

J. J. M. Halls, C. A. Walsh, N. C. Greenham, E. A. Marseglia, R. H. Friend, S. C. Moratti, A. B. Homes, "Efficient photodiodes from interpenetrating polymer networks", *Nature*, No. 376, p. 498, 1995.

(Continued)

*Primary Examiner* — Ling Choi
*Assistant Examiner* — Catherine S Branch
(74) *Attorney, Agent, or Firm* — DLA Piper LLP (US)

(57) ABSTRACT

An electron donating organic material includes a benzothiadiazole compound including (a) a benzothiadiazole skeleton and (b) an oligothiophene skeleton, and having a band gap (Eg) of 1.8 eV or less, and a level of highest occupied molecular orbital (HOMO) of −4.8 eV or less, wherein said benzothiadiazole compound is formed by covalently combining the benzothiadiazole skeleton and the oligothiophene skeleton alternately, a proportion between the benzothiadiazole skeleton and the oligothiophene skeleton is within a range of 1:1 to 1:2 (however, excluding 1:1), and the number of thiophene rings contained in an oligothiophene skeleton is 3 or more and 12 or less.

9 Claims, 1 Drawing Sheet

(56) References Cited

OTHER PUBLICATIONS

E. Kymakis, G. A. J. Amaratunga, "Single-wall carbon nanotube/conjugated polymer photovoltaic devices", *Applied Physics Letters* (*U. S. A.*), vol. 80, p. 112, 2002.

G. Yu, J. Gao, J. C. Hummelen, F. Wudl, A. J. Heeger, "Polymer Photovoltaic Cells: Enhanced Efficiencies via a Network of Internal Donor-Acceptor Heterojunctions", *Science*, vol. 270, p. 1789, 1995.

E. Bundgaard, F. C. Krebs, "Low band gap polymers for organic photovoltaics", *Solar Energy Materials & Solar Cells*, vol. 91, p. 954, 2007.

X. Li, W. Zeng, Y. Zhang, Q. Hou, W. Yang, Y. Cao, "Synthesis and properties of novel poly(*p*-phenylenevinylene copolymers for near-infrared emitting diodes", *European Polymer Journal*, vol. 41, p. 2923, 2005.

E. Bundgaard, F. C. Krebs, "Low-Band-Gap Conjugated Polymers Based on Thiophene, Benzothiadiazole, and Benzobis(thiadiazole)", *Macromolecules*, vol. 39, p. 2823, 2006.

Bundgaard Eva et al., "Low band gap polymers for organic solar cells", *Proceedings of SPIE—The International Society for Optical Engineering*, 2006, 6334, 6334OT/1-6334OT/10, Abstract, Scheme 4, Table 3.

\* cited by examiner

ELECTRON DONATING MATERIAL, MATERIAL FOR PHOTOVOLTAIC DEVICES AND PHOTOVOLTAIC DEVICE

RELATED APPLICATIONS

This is a §371 of International Application No. PCT/JP2009/054836, with an international filing date of Mar. 13, 2009, which is based on Japanese Patent Application Nos. 2008-103205 filed Apr. 11, 2008 and 2008-271688 filed on Oct. 22, 2008, the subject matter of which is incorporated by reference.

TECHNICAL FIELD

This disclosure relates to an electron donating organic material, a material for photovoltaic devices and a photovoltaic device using the same.

BACKGROUND ART

Solar cells have been attracting attention as an environment-friendly electric energy source. Now, inorganic substances, such as monocrystalline silicon, polycrystalline silicon, amorphous silicon and compound semiconductor, are used as a semiconductor material of a photovoltaic device of a solar cell. However, solar cells produced using inorganic semiconductors have not spread widely for home use because of their cost higher than that of power generation systems such as thermal power generation and nuclear power generation. Such a high cost is derived mainly from the process of producing a semiconductor film in vacuum at high temperatures. Therefore, to simplify the production process, organic solar cells using organic semiconductors such as conjugated polymers and organic crystals or organic dyes as semiconductor materials have been investigated.

However, the most serious problem with organic solar cells using organic semiconductors such as conjugated polymers and the like is that such solar cells are low in photoelectric conversion efficiency in comparison with solar cells using conventional inorganic semiconductors, and therefore such solar cells have not been used practically, yet. The following three points are major reasons for the low photoelectric conversion efficiency of organic solar cells using conventional conjugated polymers. The first reason is that solar light absorption efficiency is low. The second reason is that a bound state called exciton in which an electron and a hole generated by solar light are resistant to separation is formed. The third reason is that since a trap which captures a carrier (electron or hole) is likely to be formed, a produced carrier tends to be captured by the trap, resulting in low mobility of carriers. In other words, while a semiconductor material is generally required that the carriers of the material has a high mobility μ, there is a problem that conjugated polymers have mobilities μ being lower than those of conventional inorganic crystalline semiconductors or amorphous silicon.

Therefore, finding the means for successfully separating a produced electron and a produced hole from exciton and the means for preventing carriers from scattering in an amorphous region of a conjugated polymer or between conjugated polymer chains or from being captured by the trap to increase the mobility is the key for bringing solar cells using organic semiconductors in practical use.

The hitherto known photoelectric conversion devices using organic semiconductors can now be generally classified into the following elemental constitutions; that is, a Schottky type in which an electron donating organic material (p-type organic semiconductor) and metal with a small work function are joined, and a heterojunction type in which an electron accepting organic material (n-type organic semiconductor) and an electron donating organic material (p-type organic semiconductor) are joined, and so on. In such devices, since only organic layers (almost several molecular layers) in a junction contribute to the generation of a photocurrent, the photoelectric conversion efficiency is low and, and therefore the improvement in the efficiency is a pending problem.

One approach for increasing the photoelectric conversion efficiency is a bulk heterojunction type in which an electron accepting organic material (n-type organic semiconductor) and an electron donating organic material (p-type organic semiconductor) are mixed so that joined surfaces which contribute to photoelectric conversion are increased (for example, J. J. M. Halls, C. A. Walsh, N. C. Greenham, E. A. Marseglia, R H. Friend, S. C. Moratti, A. B. Homes, "Nature" No. 376, p. 498, 1995). In particular, photoelectric conversion materials using a conjugated polymer as an electron donating organic material (p-type organic semiconductor) and using fullerene such as $C_{60}$ or carbon nanotubes as well as a conducting polymer having n-type semiconductor properties as an electron accepting organic material have been reported (for example, E. Kymakis, G. A. J. Amaratunga, "Applied Physics Letters" (U.S.A.), Vol. 80, p. 112, 2002, G. Yu, J. Gao, J. C. Hummelen, F. Wudl, A. J. Heeger, "Science", Vol. 270, p. 1789, 1995, Japanese Unexamined Patent Application Publication No. 2003-347565 and Japanese Unexamined Patent Application Publication No. 2004-165474).

Moreover, a photoelectric conversion material has been reported which comprises an organic semiconductor with a band gap having been reduced by the introduction of an electron donating group and an electron attracting group into a main chain to cause the organic semiconductor to efficiently absorb the radiant energy of a wide range of the solar light spectrum (for example, E. Bundgaard, F. C. Krebs, "Solar Energy Materials & Solar Cells", Vol. 91, p. 954, 2007). Strenuous researches are made to thiophene skeletons as the electron donating group and to benzothiadiazole skeletons as the electronic attracting group (for example, X. Li, W. Zeng, Y. Zhang, Q. Hou, W. Yang, Y. Cao, "European Polymer Journal", Vol. 41, p. 2923, 2005, E. Bundgaard, F. C. Krebs, "Macromolecules", Vol. 39, p. 2823, 2006, U.S. Unexamined Patent Application Publication No. 2006-52612, Japanese Unexamined Patent Application Publication No. 2003-104976, U.S. Unexamined Patent Application Publication No. 2006-174937 and U.S. Unexamined Patent Application Publication No. 2004-115473). However, sufficient photoelectric conversion efficiency has not been obtained, yet.

As described above, all of such conventional organic solar cells have a problem that photoelectric conversion efficiency is low. It could therefore be helpful to provide a photovoltaic device with high photoelectric conversion efficiency.

SUMMARY

This disclosure pertains to an electron donating organic material containing a benzothiadiazole compound in which (a) a benzothiadiazole skeleton and an oligothiophene skeleton are contained, (b) a band gap (Eg) is 1.8 eV or less, and (c) the level of the highest occupied molecular orbital (HOMO) is −4.8 eV or less, wherein the benzothiadiazole compound is formed by covalently combining the benzothiadiazole skeleton and the oligothiophene skeleton alternately, the proportion between the benzothiadiazole skeleton and the oligothiophene skeleton is within a range of 1:1 to 1:2 (however, excluding 1:1), and the number of thiophene rings contained in an oligothiophene skeleton is 3 or more and 12 or less, and a material for photovoltaic devices using the electron donating organic material, and a photovoltaic device.

It is thus possible to provide a photovoltaic device with high photoelectric conversion efficiency, which achieves a high short-circuit current density (Isc) and a high open circuit voltage (Voc) simultaneously.

EXPLANATION OF REFERENTIAL SYMBOLS

Figure 1:
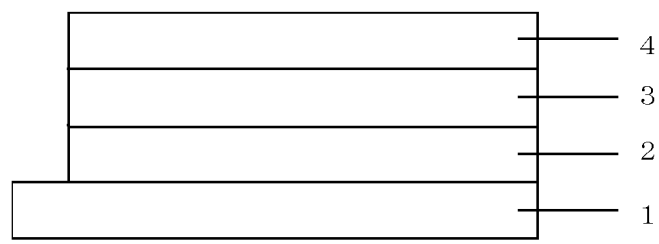
FIG. 1 is a schematic diagram showing one aspect of the photovoltaic device.

| | |
|---|---|
| 1 | substrate |
| 2 | positive electrode |
| 3 | organic semiconductor layer |
| 4 | negative electrode |
| 5 | layer containing a benzothiadiazole compound having a structure represented by formula (1) |
| 6 | layer containing an electron accepting organic material |

DETAILED DESCRIPTION

The electron donating organic material comprises a benzothiadiazole compound in which (a) a benzothiadiazole skeleton and an oligothiophene skeleton are contained, (b) a band gap (Eg) is 1.8 eV or less, and (c) the level of the highest occupied molecular orbital (HOMO) is −4.8 eV or less. The electron donating organic material can be used for a material for photovoltaic devices, a material for organic electroluminescence devices, a material for organic transistors, a material for wavelength conversion elements, and a material for organic laser, and in particular, it can be preferably used as a material for photovoltaic devices. Hereinafter, the benzothiadiazole compound to be used for the electron donating organic material will be described.

The benzothiadiazole compound contains (a) a benzothiadiazole skeleton and an oligothiophene skeleton. Herein, the oligothiophene skeleton refers to a skeleton in which 3 or more and 12 or less thiophene rings are linked by a conjugated bond. By having both of the benzothiadiazole skeleton and the oligothiophene skeleton, it becomes possible to achieve (1) a deep level of the highest occupied molecular orbital (HOMO), (2) a wide optical absorption wavelength range, and (3) high carrier mobility at a high level simultaneously. Furthermore, by employing 3 or more as the number of thiophene rings contained in an oligothiophene skeleton, the optical absorption wavelength range of the benzothiadiazole compound can be widened more. Therefore, a high short-circuit current density (Isc) can be achieved in the photovoltaic device. The number of thiophene rings is more preferably 4 or more. On the other hand, by employing 12 or less as the number of thiophene rings contained in an oligothiophene skeleton, the level of the highest occupied molecular orbital (HOMO) of the benzothiadiazole compound can be made deeper. Therefore, a high open circuit voltage (Voc) can be achieved in the photovoltaic device. The number of thiophene rings is more preferably 8 or less.

In the benzothiadiazole compound, (b) a band gap (Eg) is 1.8 eV or less. The band gap refers to an energy difference between the level of the highest occupied molecular orbital (HOMO) and the level of the lowest unoccupied molecular orbital (LUMO). By maintaining the band gap at 1.8 eV or less, the absorption efficiency of light can be increased. Particularly in the case where the benzothiadiazole compound is used as a material for photovoltaic devices, if the band gap is more than 1.8 eV, since the absorption efficiency of solar light is deteriorated, the photoelectric conversion efficiency is decreased. On the other hand, when the band gap is too small, this may cause the reduction in open circuit voltage (Voc). From these viewpoints, the band gap is preferably 1.8 eV or less and 0.8 eV or more, more preferably 1.8 eV or less and 1.2 eV or more, more preferably 1.8 eV or less and 1.4 eV or more, and furthermore preferably 1.8 eV or less and 1.6 eV or more. Herein, the band gap of the benzothiadiazole compound is determined by forming a thin film from the benzothiadiazole compound and substituting a wavelength at an optical absorption edge of the thin film into the following formula.

$Eg(eV)=1240/\text{wavelength (nm) at an optical absorption edge of thin film}$

A method for forming a thin film to be used here is not particularly limited, and the benzothiadiazole compound is usually dissolved in an organic solvent such as chloroform, tetrahydrofuran, chlorobenzene or the like and the resulting solution is applied onto a glass substrate by a wet coating method such as spin coating to form a thin film. Generally, the thickness of the thin film is preferably within a range of 5 to 500 nm, and more preferably within a range of 10 to 200 nm since if the thickness is too small, the absorbance of the film may be too low and if the thickness is too large, the absorbance of the film may be too high to interfere with measurement.

To maintain the band gap of the benzothiadiazole compound at 1.8 eV or less, it is effective to make intramolecular charge transfer (CT) easily occur. That is, it is effective to covalently combine the benzothiadiazole skeleton being an electron attracting group and the oligothiophene skeleton being an electron donating group alternately. Further, it is also effective for maintaining the band gap at 1.8 eV or less to minimize the twist between thiophene rings constituting the oligothiophene. To realize this, it is effective that at least one of two substituents adjacent to each other of two thiophene rings adjacent to each other is a hydrogen atom which is low in steric hindrance.

In the benzothiadiazole compound, it is important that the level of the highest occupied molecular orbital (HOMO) is deep, specifically, the level of the highest occupied molecular orbital (HOMO) is maintained at −4.8 eV or less, as described in the paragraph (c). When the level of the highest occupied molecular orbital (HOMO) is more than −4.8 eV, the photoelectric conversion efficiency is decreased since the open circuit voltage (Voc) of the photovoltaic device is reduced. On the other hand, when the level of the highest occupied molecular orbital (HOMO) is too low, an electron and a hole produced by the charge separation of an exciton takes place may be recombined on an electron accepting organic material side to vanish. From these viewpoints, the level of the highest occupied molecular orbital (HOMO) is preferably −4.8 eV or less and −6.5 eV or more, more preferably −4.8 eV or less and −6.1 eV or more, more preferably −4.8 eV or less and −5.5 eV or more, and furthermore preferably −4.8 eV or less and −5.3 eV or more. Herein, the level of the highest occupied molecular orbital (HOMO) of the benzothiadiazole compound is determined by forming a thin film from the benzothiadiazole compound and measuring photoelectron spectrum. While a method for forming a thin film to be used here is not particularly limited, generally, the above-mentioned method can be used. Generally, the thickness of the thin film is preferably within a range of 5 to 500 nm, and more preferably within a range of 10 to 200 nm since if the thickness is too small, the underlying substrate may have an effect on the thin film and if the thickness is too large, the film thickness may become uneven to interfere with measurement. In addition, the term "−4.8 eV or less" means that its absolute value is 4.8 or more like −4.9 eV or −5.0 eV.

To maintain the HOMO at −4.8 eV or less, it is important that both the number of the oligothiophene skeletons being an electron donating group and the number of thiophene rings contained in the oligothiophene skeleton are not too large. Specifically, it is preferable that the proportion between the benzothiadiazole skeleton being an electron attracting group and the oligothiophene skeleton being an electron donating group is 1:1 to 1:2 (however, excluding 1:1), and it is preferable to maintain the number of thiophene rings contained in an oligothiophene skeleton at 12 or less.

From the viewpoint of widening an optical absorption wavelength range more, increasing carrier mobility more and securing chemical stability and thermal stability, a position of the benzothiadiazole compound molecule to which a benzothiadiazole skeleton is linked is preferably a fourth position and a seventh position. Specifically, 2,1,3-benzothiadiazole-4,7-diyl is preferred. Further, from the same viewpoint, a position of the benzothiadiazole compound molecule to which a thiophene ring is linked is preferably a second position and a fifth position (carbon adjacent to a sulfur atom contained in the thiophene ring). Specifically, the oligothiophene skeleton is preferably oligo(thiophene-2,5-diyl).

As the benzothiadiazole compound having characteristics described above, a compound having a structure represented by the following formula (1) is preferred. Optical absorption efficiency in a long wavelength range is improved by arranging the benzothiadiazole skeleton and the oligothiophene skeleton orderly in the form of oligothiophene skeleton-benzothiadiazole skeleton-oligothiophene skeleton as shown in formula (1) in comparison with the case where these skeletons are arranged in a random fashion.

undecyl group and a dodecyl group. The alkyl group may be linear, branched or cyclic, and also may be unsubstituted or substituted. Examples of the substituent in the case of being substituted include an alkoxy group, an aryl group, a heteroaryl group and halogen, which will be described below. The number of carbon atoms of the alkyl group is preferably 2 or more from the viewpoint of processability, and preferably 20 or less for enhancing optical absorption efficiency more.

Further, the alkoxy group represents an aliphatic hydrocarbon group with an ether linkage, such as a methoxy group, an ethoxy group, a propoxy group and a butoxy group. The aliphatic hydrocarbon group may be unsubstituted or substituted. The number of carbon atoms of the alkoxy group is preferably 2 or more from the viewpoint of processability and preferably 20 or less for achieving higher optical absorption efficiency. Examples of the substituents in the case where the alkoxy group is substituted include an aryl group, a heteroaryl group, and halogen, described later.

The aryl group represents an aromatic hydrocarbon group, such as a phenyl group, a naphthyl group, a biphenyl group, phenanthryl group, an anthryl group, a terphenyl group, a pyrenyl group, a fluorenyl group and a perylenyl group. The aryl group may be unsubstituted or substituted. The number of carbon atoms of the aryl group is preferably 6 or more and 30 or less from the viewpoint of processability. Examples of the substituents in the case where the aryl group is substituted include an alkyl group, and a heteroaryl group and halogen, described later.

The heteroaryl group represents a heteroaromatic ring group having an atom or atoms other than carbon, such as a thienyl group, a furyl group, a pyrrolyl group, an imidazolyl group, a pyrazolyl group, an oxazolyl group, a pyridyl group, a pyrazyl group, a pyrimidyl group, a quinolinyl group, an isoquinolyl group, a quinoxalyl group, an acridinyl group, an indolyl, a carbazolyl group, a benzofuran group, a dibenzofuran group, a benzothiophene group, a dibenzothiophene group, a benzodithiophene group, a silole group, a benzosilole group and a dibenzosilole group. The heteroaryl group may be unsubstituted or substituted. Examples of the substituents in the case where the heteroaryl group is substituted include an alkyl group, an aryl group, and halogen described later.

[Chem. 1]

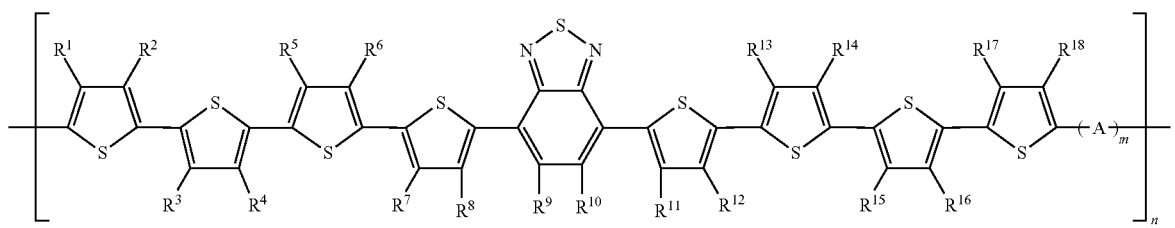

(1)

In the formula (1), $R^1$ to $R^{18}$ may be the same or different from each other and are each selected from among hydrogen, an alkyl group, an alkoxy group, an aryl group, a heteroaryl group and halogen. A represents a divalent arylene group having a six-membered ring structure or a divalent heteroarylene group having a six-membered ring structure. m is 0 or 1. n is within a range of 1 to 1000.

Herein, the alkyl group represents a saturated aliphatic hydrocarbon group such as a methyl group, an ethyl group, a propyl group, a butyl group, a pentyl group, a hexyl group, a heptyl group, an octyl group, a nonyl group, a decyl group, an The halogen is fluorine, chlorine, bromine or iodine.

The divalent arylene group having a six-membered ring structure represents a divalent (i.e., having two binding sites) aromatic hydrocarbon group. The arylene group may be unsubstituted or substituted. Examples of the substituents in the case where the arylene group is substituted include an alkyl group, a heteroaryl group, and halogen. Preferable specific examples of the divalent arylene group having a six-membered ring structure include a phenylene group, a naphthylene group, a biphenylene group, phenanthrylene group, an anthrylene group, a terphenylene group, a pyrenylene group, a fluorenylene group and a perylenylene group.

The divalent heteroarylene group having a six-membered ring structure represents a group having a six-membered ring structure of divalent heteroaromatic ring groups. The heteroarylene group may be unsubstituted or substituted. Examples of the substituents in the case where the heteroarylene group is substituted include an alkyl group, an aryl group, and halogen. Preferable specific examples of the divalent heteroarylene group having a six-membered ring structure include a pyridylene group, a pyrazylene group, a quinolinylene group, an isoquinolylene group, a quinoxalylene group, an acridinylene group, an indolylene, a carbazolylene group, a benzofuran group, a dibenzofuran group, a benzothiophene group, a dibenzothiophene group, a benzodithiophene group, a benzosilole group and a dibenzosilole group.

$R^1$ to $R^{18}$ in a compound represented by formula (1) are preferably hydrogen, an alkyl group or an alkoxy group from the viewpoint of securing ease of synthesis and solubility.

In formula (1), n represents a polymerization degree of the benzothiadiazole compound and is within a range of 1 to 1000. In view of the ease of film formation, the benzothiadiazole compound is preferably soluble in a solvent. n is preferably 1 to 500 from the viewpoint of this. The polymerization degree of the benzothiadiazole compound can be determined from a weight average molecular weight. The weight average molecular weight can be determined by conducting measurement by the use of GPC (gel permeation chromatography) and converting the measurement to standard samples of polystyrene. To make it soluble in a solvent, it is preferable that at least one of $R^1$ to $R^{18}$ be an alkyl group or an alkoxy group. When the molecular weight of the benzothiadiazole compound is small, a glass transition temperature or a melting point of the benzothiadiazole compound is lowered and therefore thermal stability is reduced if the number of alkyl groups or alkoxy groups is too large. Therefore, when n in formula (1) is not less than 1 and less than 10, it is more preferable that 1 to 8 groups of $R^1$ to $R^{18}$ be an alkyl group or an alkoxy group. On the contrary, when the molecular weight of the benzothiadiazole compound is large, the solubility of the benzothiadiazole compound decreases to make the formation of a thin film difficult if the number of alkyl groups or alkoxy groups is too small. Therefore, when n in formula (1) is 10 or more, it is more preferable that 4 or more groups of $R^1$ to $R^{18}$ be an alkyl group or an alkoxy group.

In formula (1), m is 0 or 1, but m is preferably 1 when n is 2 or more. Since A in formula (1) has a six-membered ring structure, a main chain of the benzothiadiazole compound is twisted due to the steric hindrance of the structure and conjugation is hardly expanded, and therefore the level of the highest occupied molecular orbital (HOMO) can be maintained at a deep level even in high molecular weight substances.

The skeleton of A in formula (1) is not particularly limited, and specific examples of the skeleton include m-phenyl, p-phenyl, biphenyl, terphenyl, quaterphenyl, naphthyl, anthrane, pyrene, benzothiophene, dibenzothiophene, indole, carbazole, fluorene, and dibenzosilole. Among these, fluorene and dibenzosilole are preferable from the viewpoint of solubility since two soluble substituents such as an alkyl group can be easily introduced into these compounds. Fluorene and dibenzosilole, described above, can achieve higher photoelectric conversion efficiency than other skeletons. The reason for this is likely that fluorene and dibenzosilole easily form a morphology which is favorable for the photovoltaic device, for example, the formation of carrier paths by the phase separation at nano level, in addition to the solubility described above.

Examples of the benzothiadiazole compound having a structure represented by formula (1) include the structures provided below. In the following structures, n is in a range of 1 to 1000.

[Chem. 2]

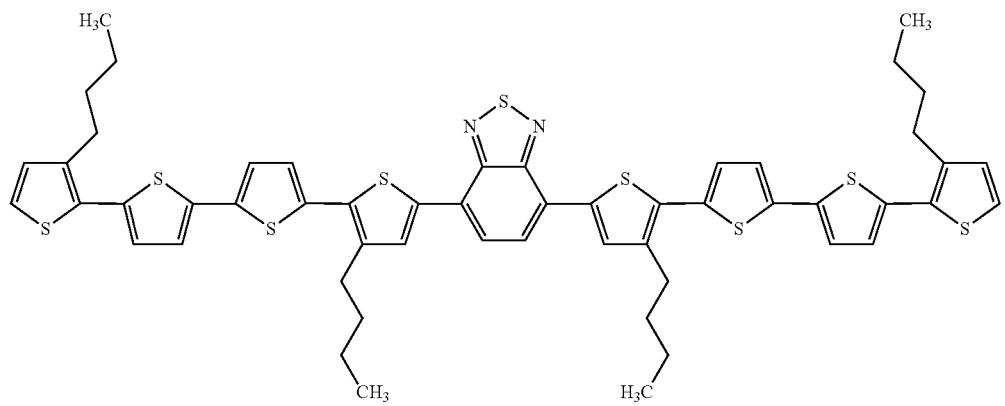

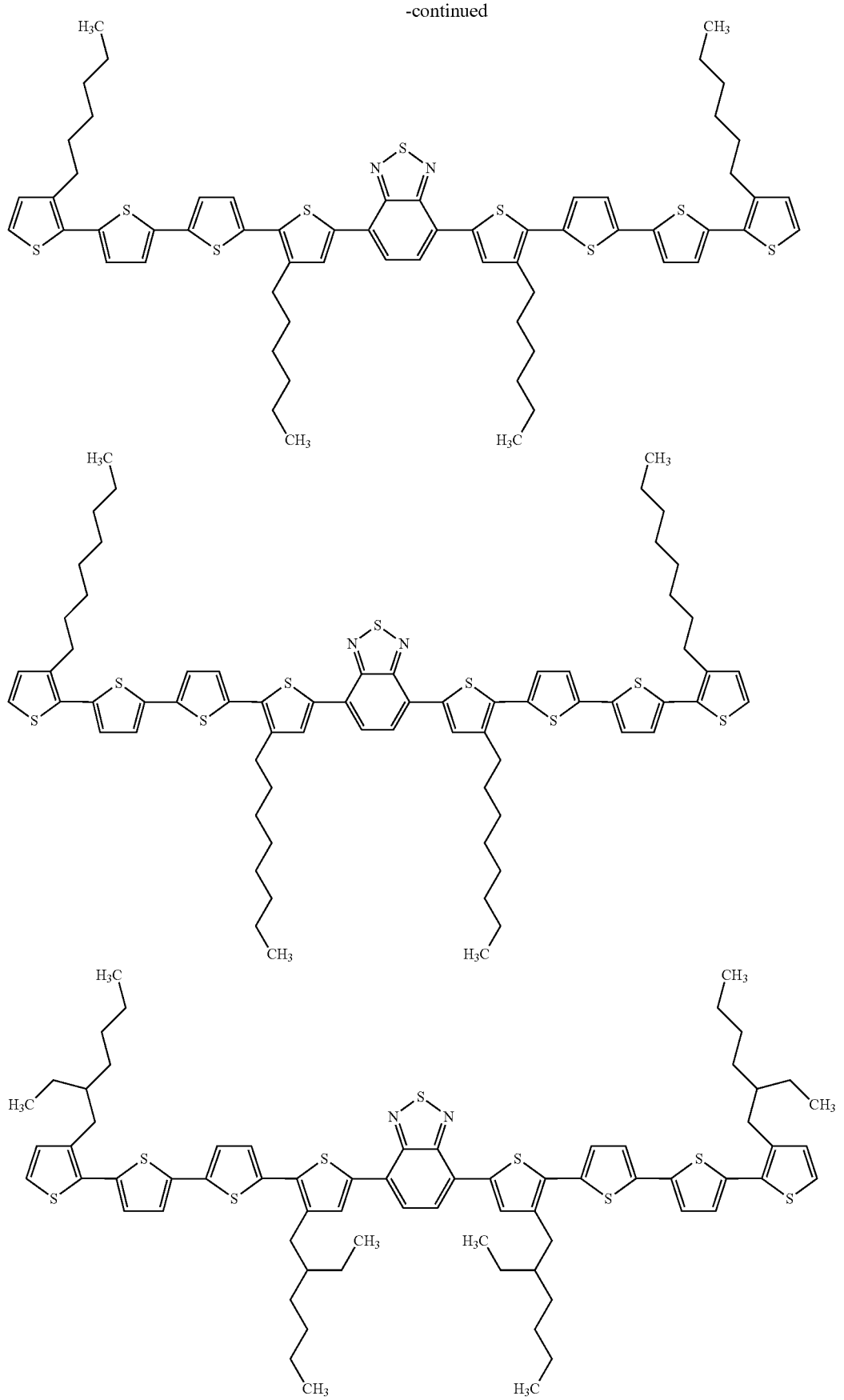

[Chem. 3]
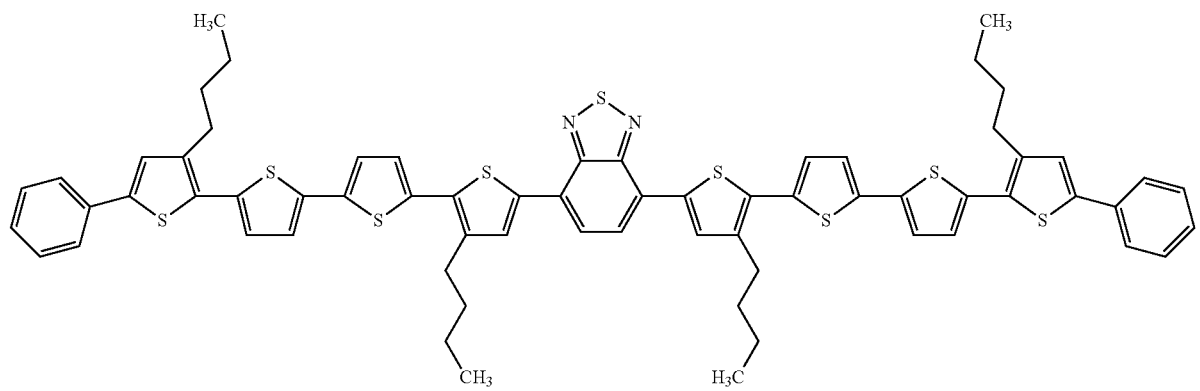
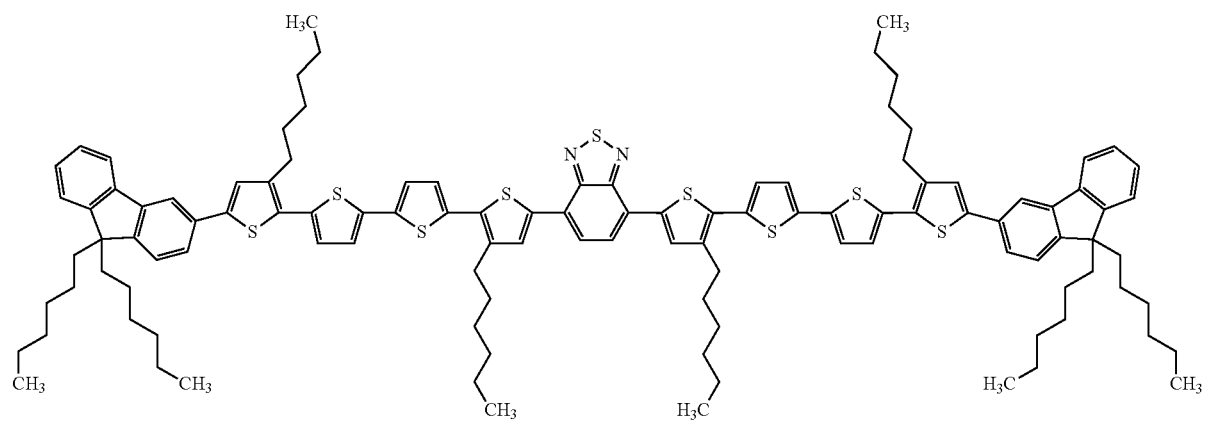
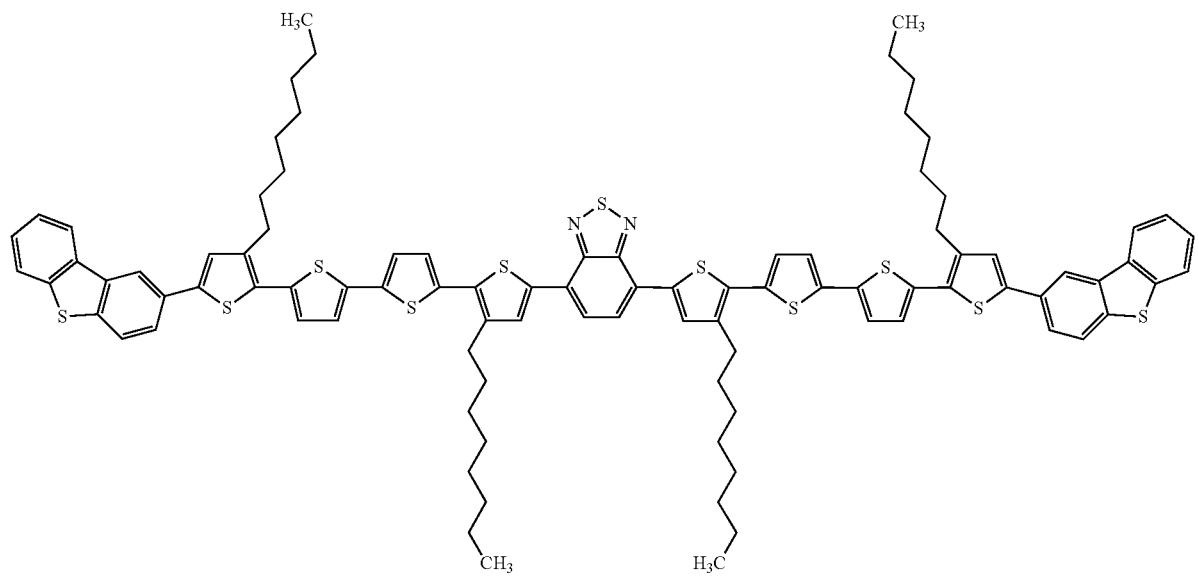

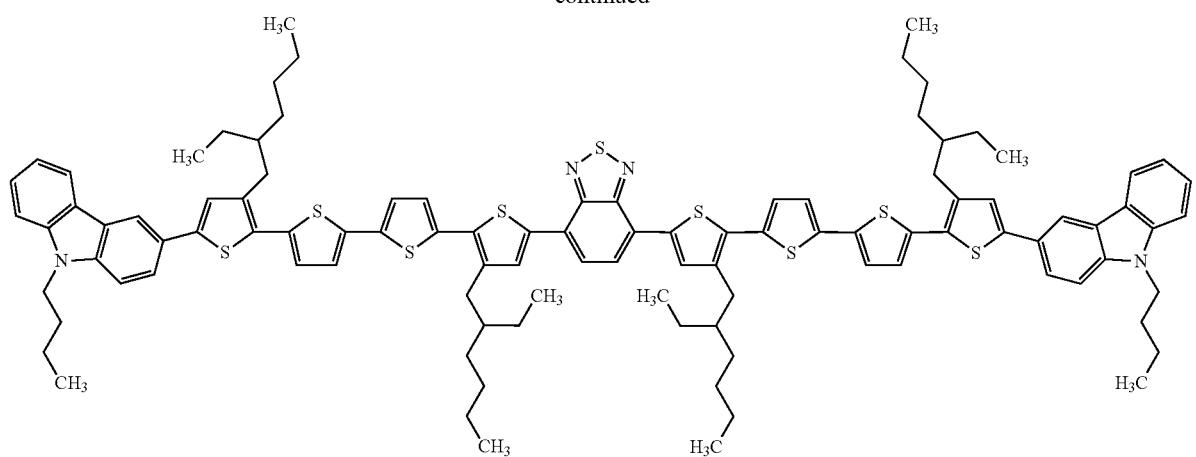
[Chem. 4]
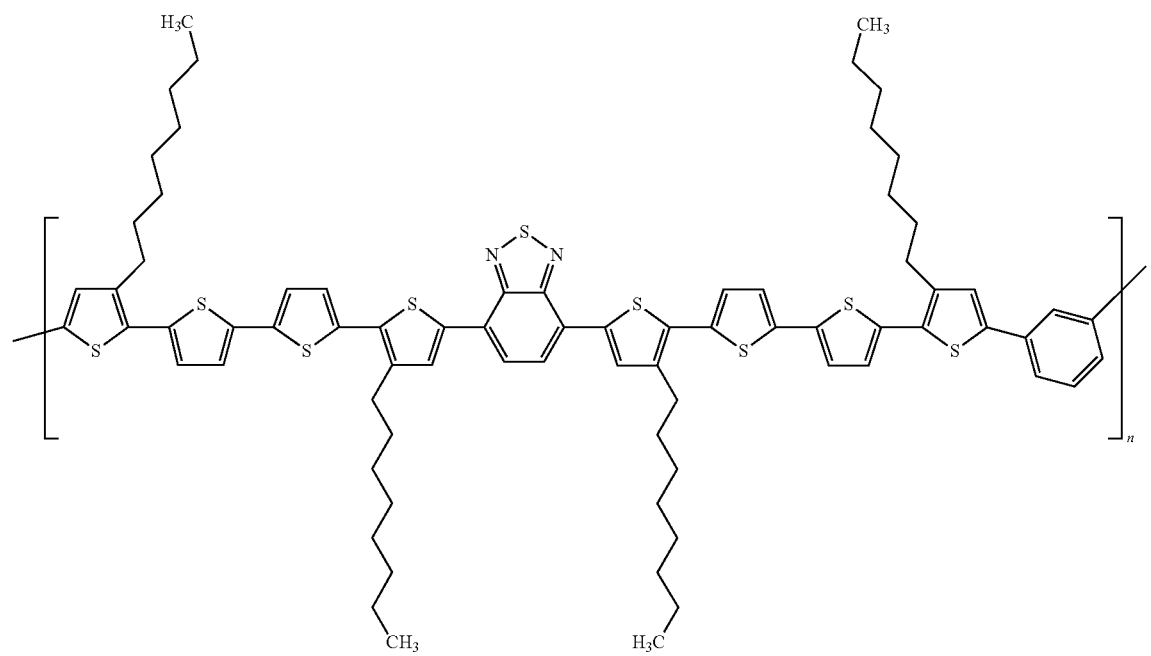

15
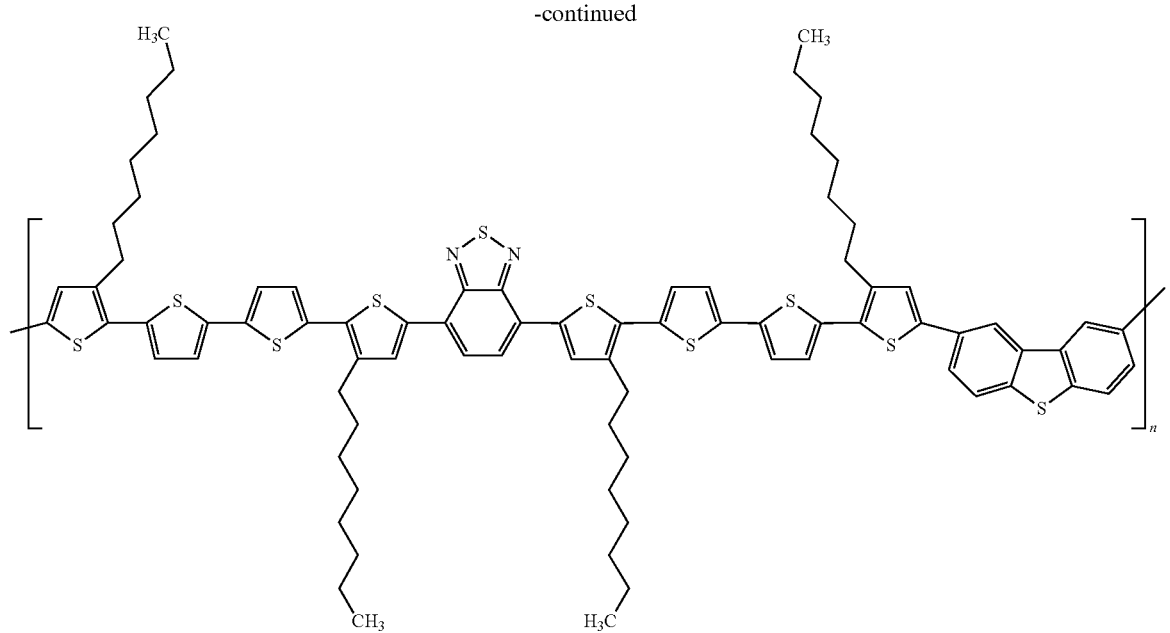
16
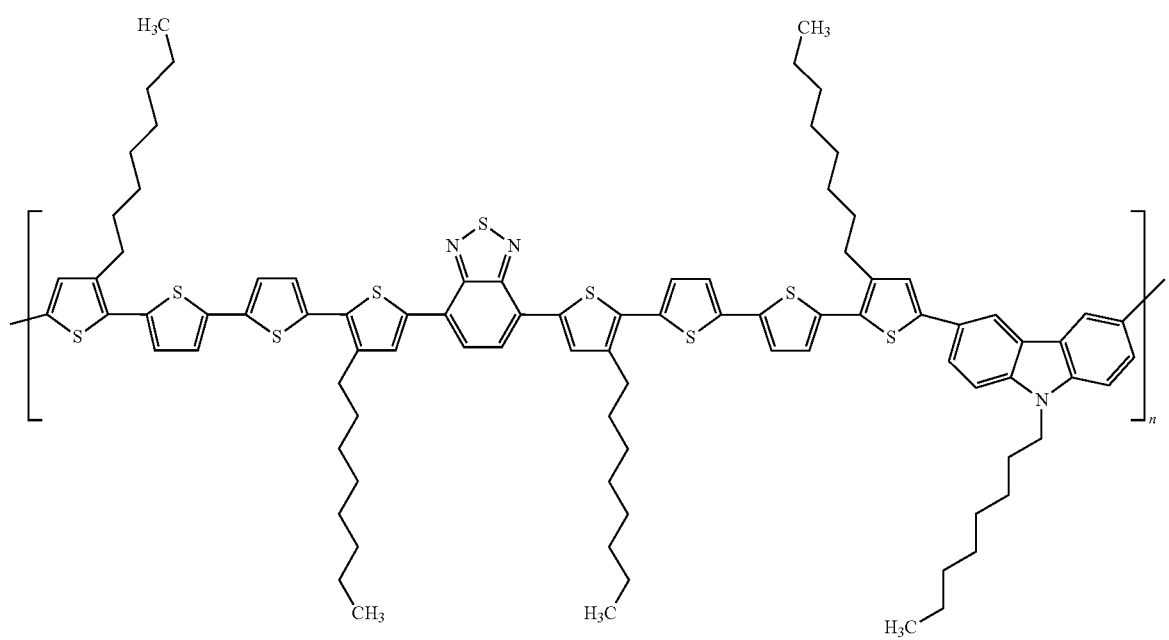

[Chem. 5]
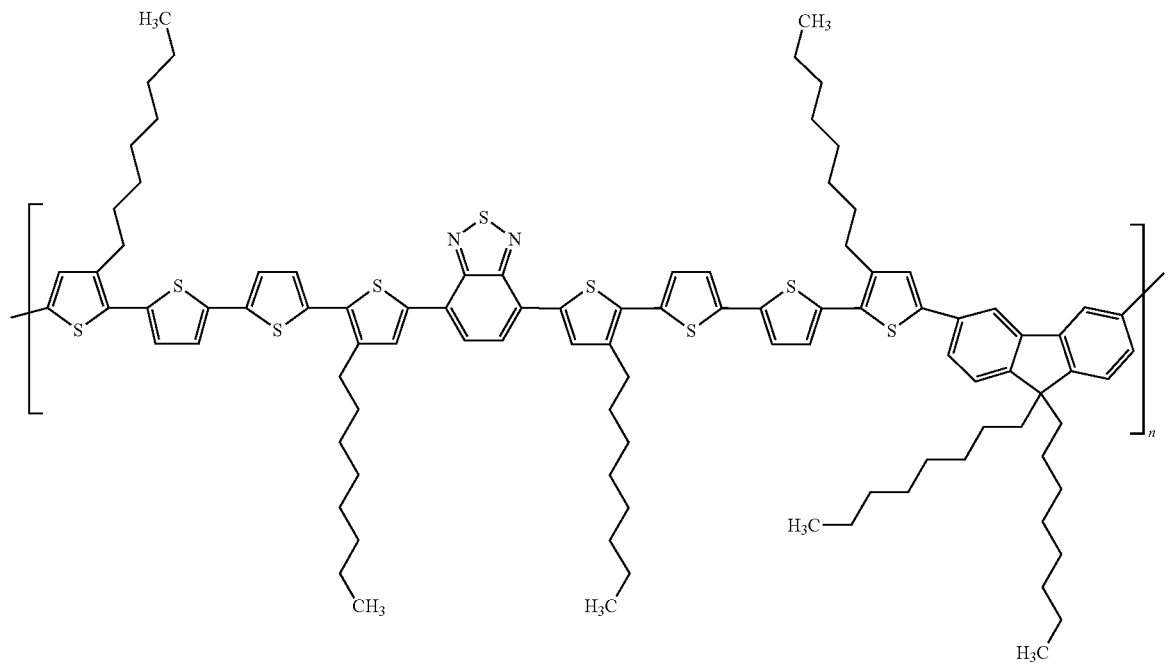
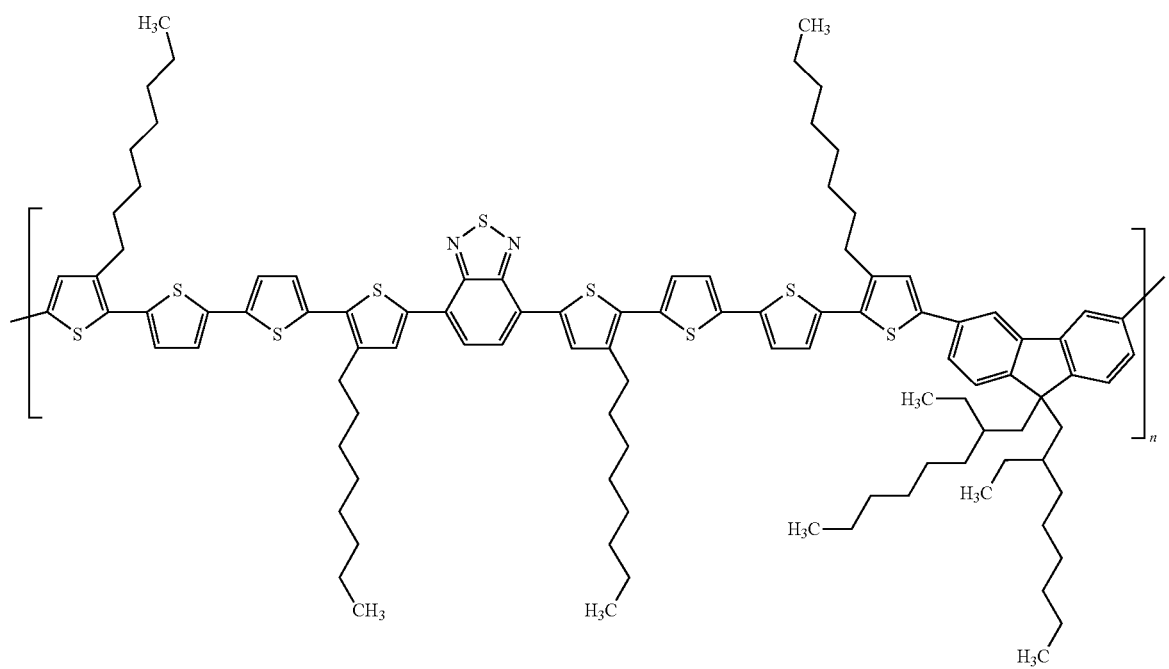

-continued
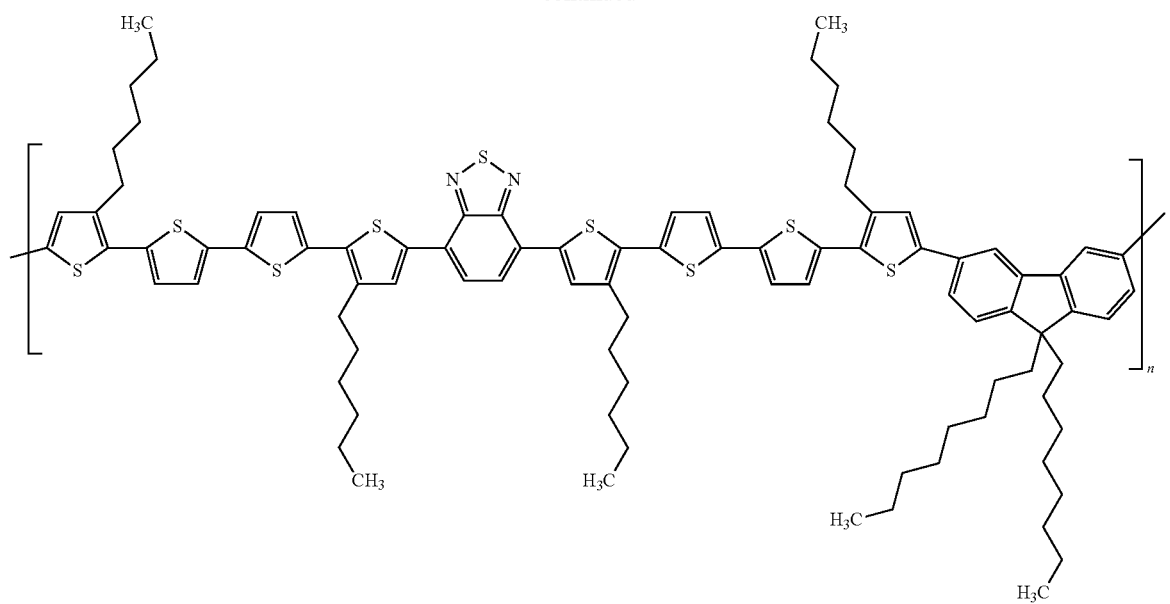
[Chem. 6]
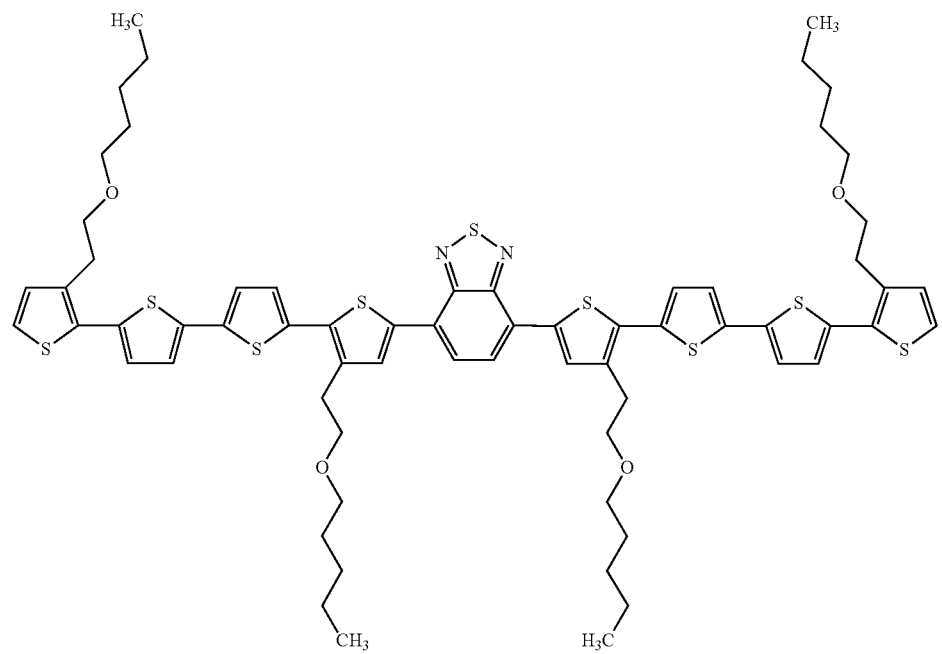

21
22
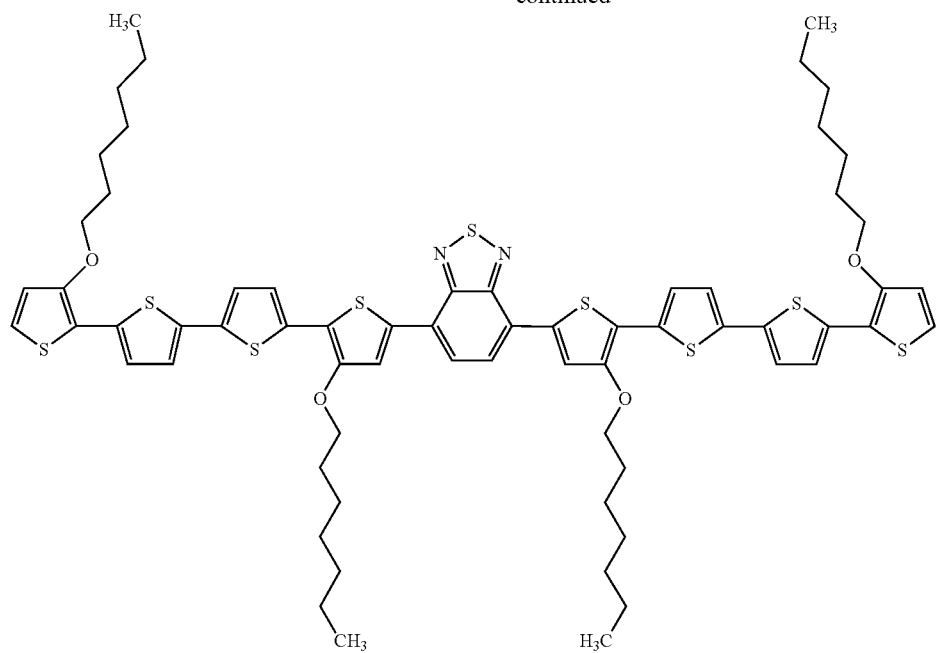
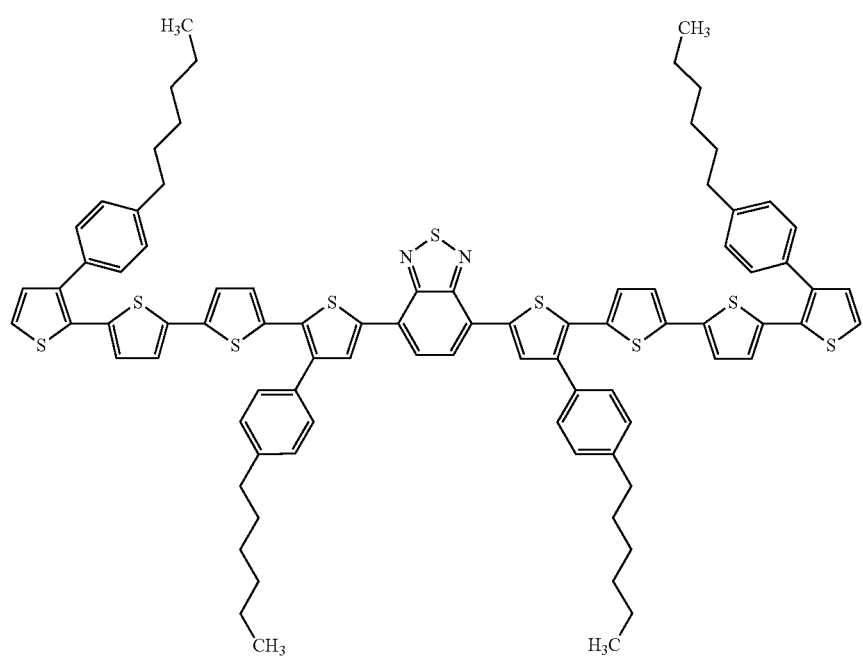

[Chem. 7]
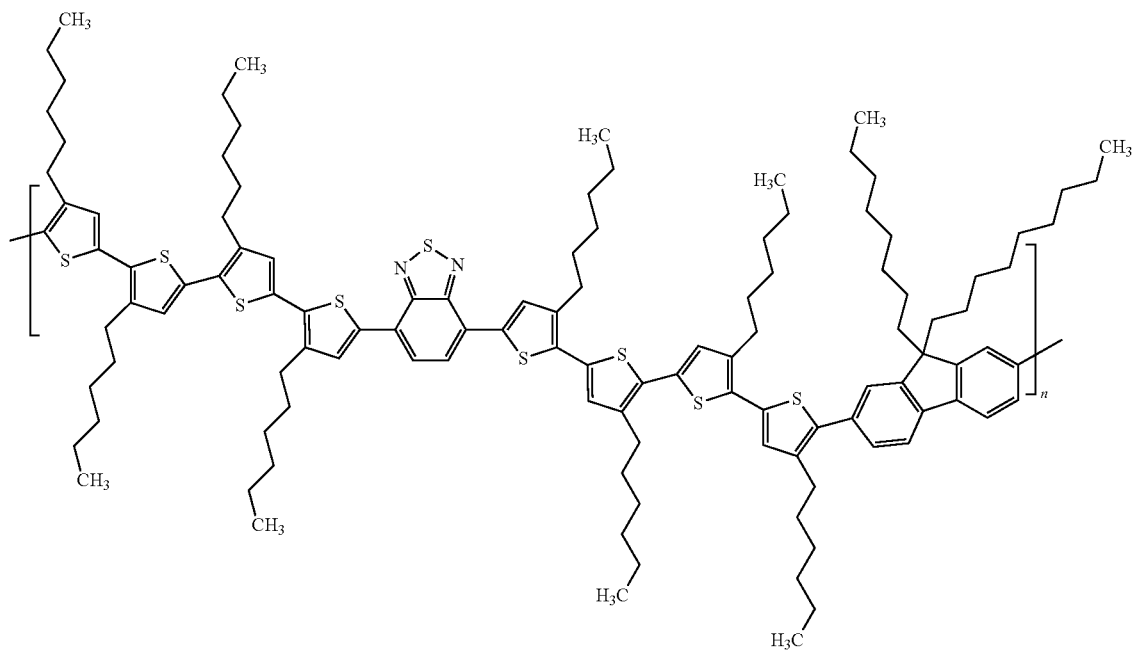
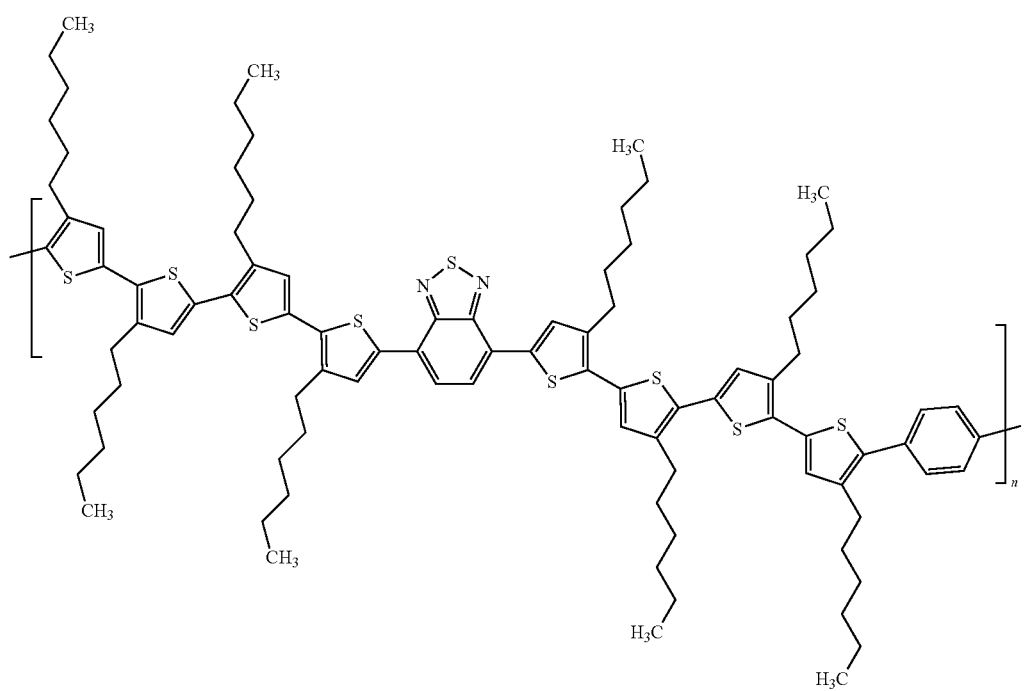

25
-continued
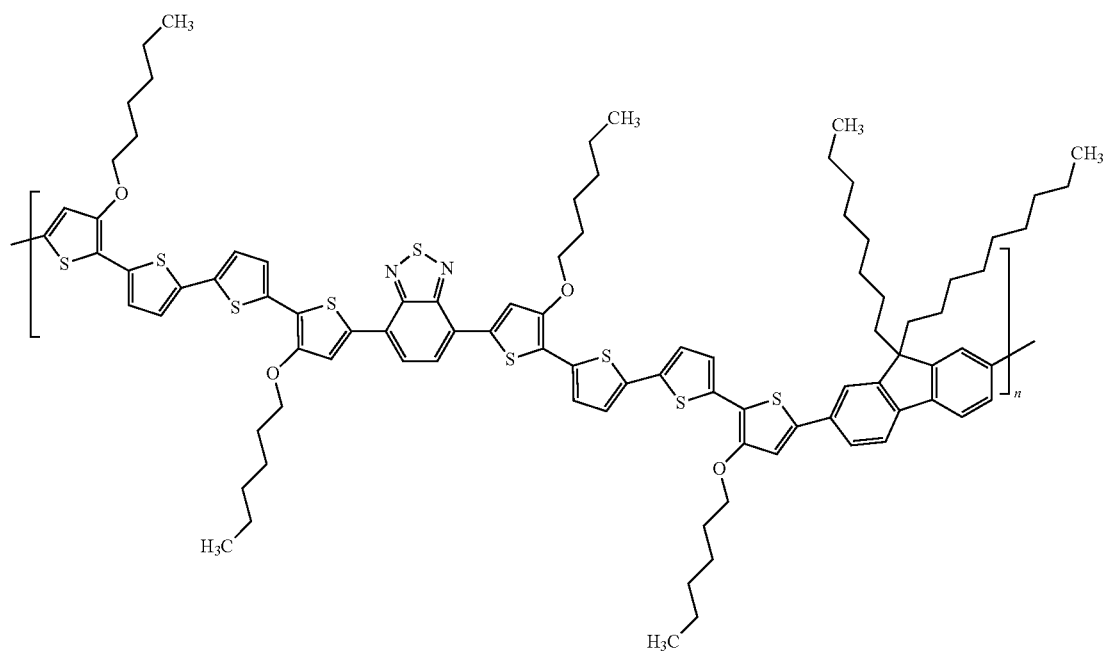
26
[Chem. 8]
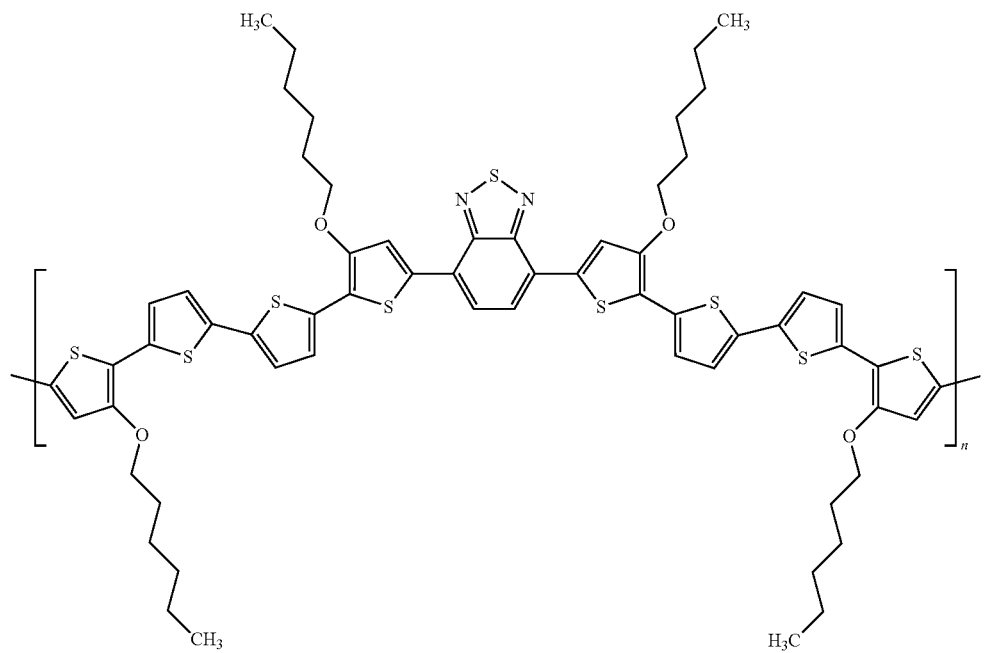

-continued
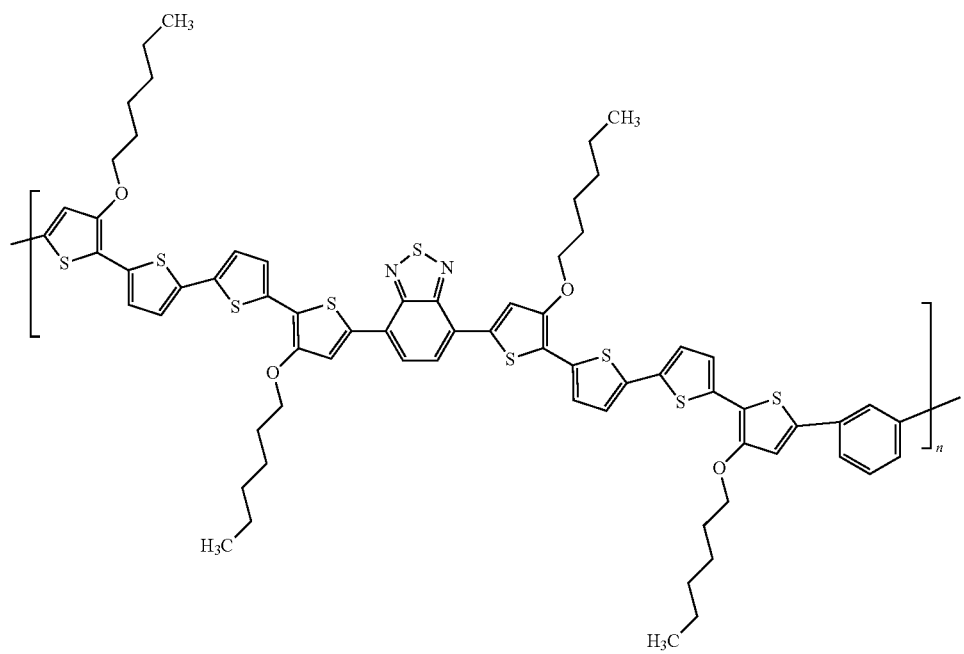
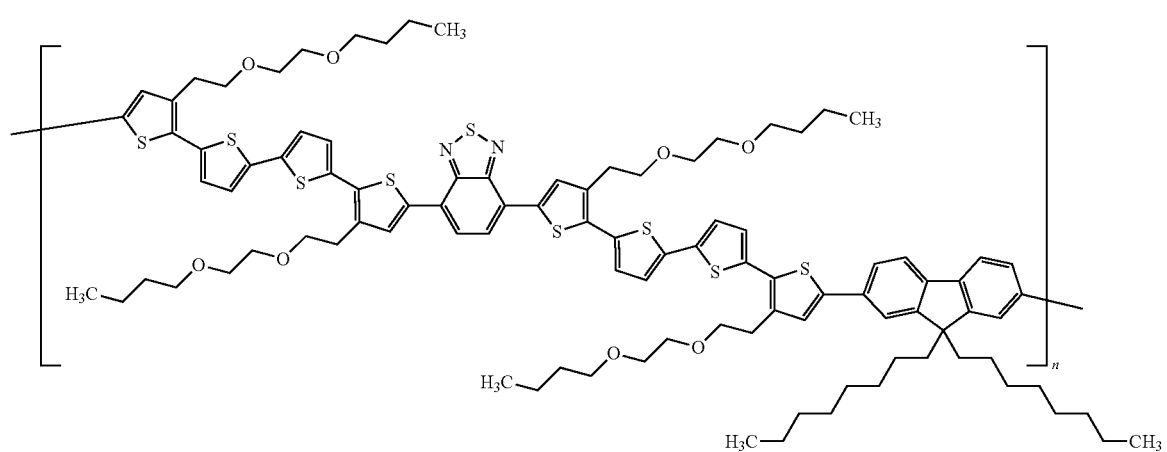
[Chem. 9]
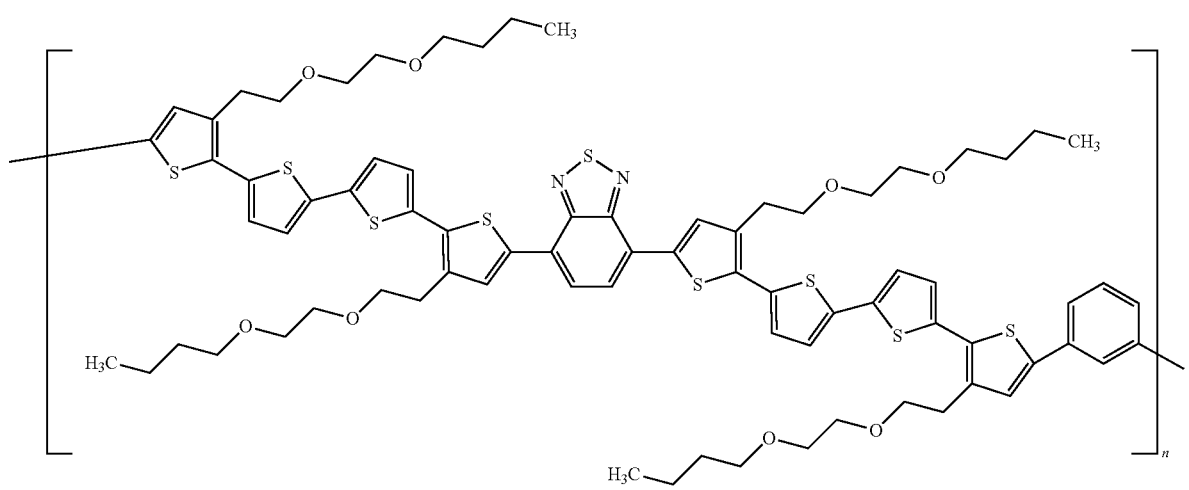

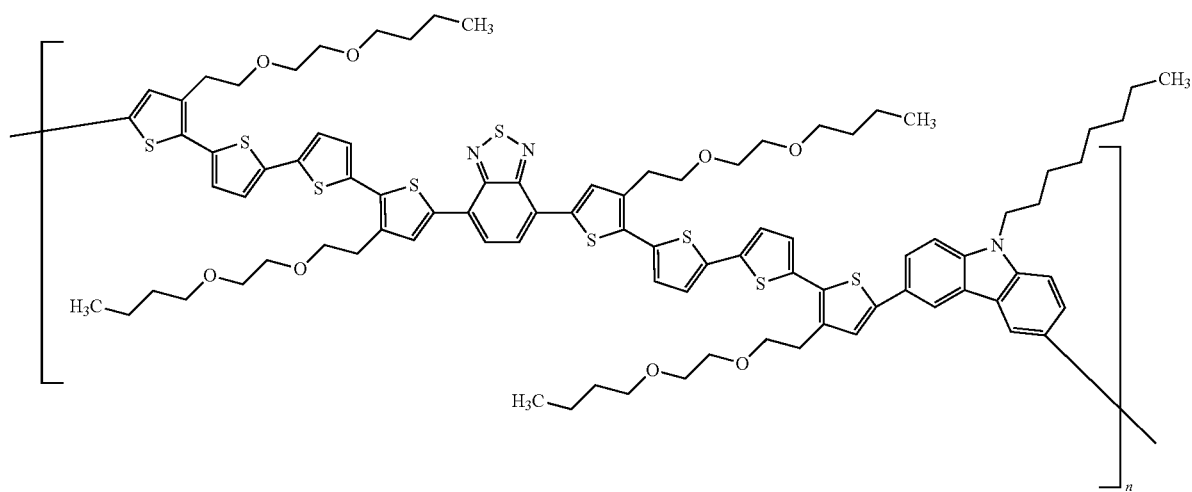
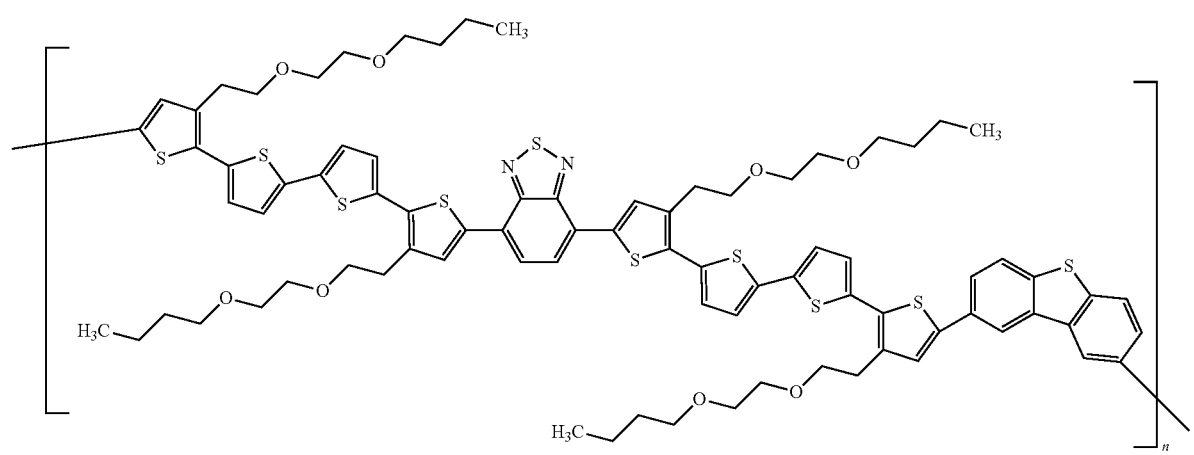
[Chem. 10]
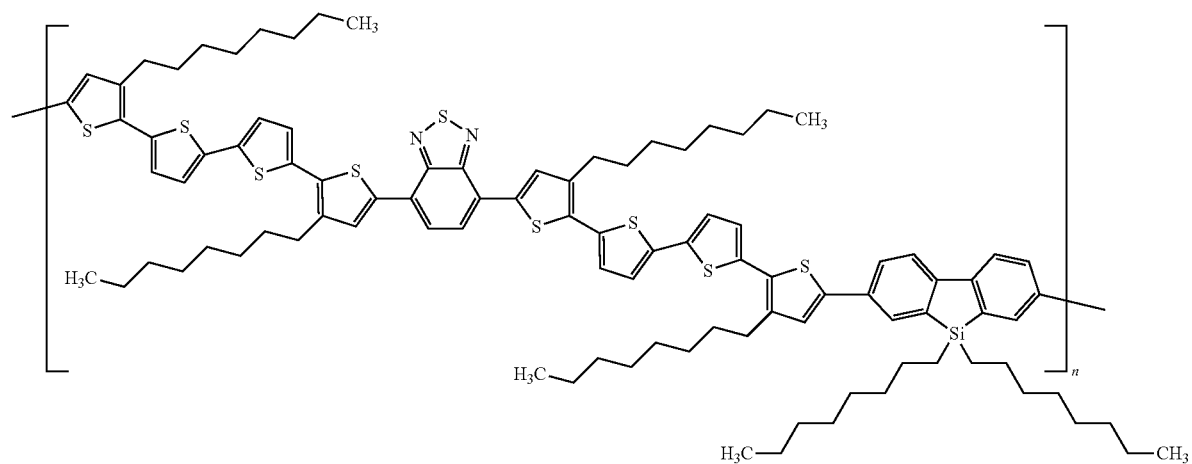

31
32
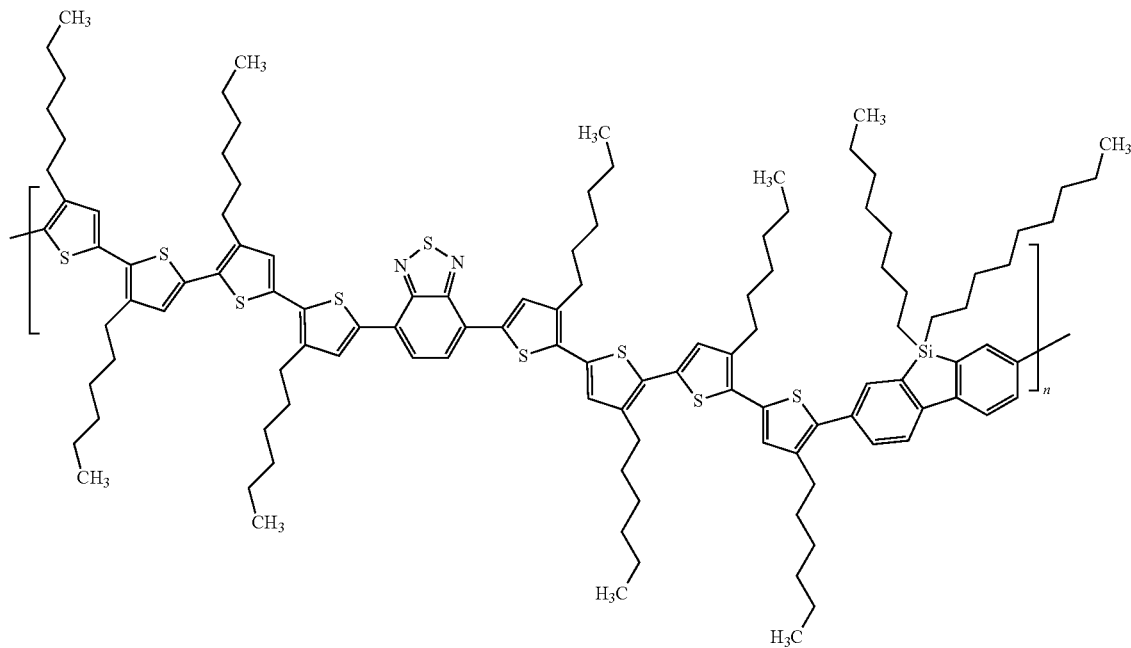
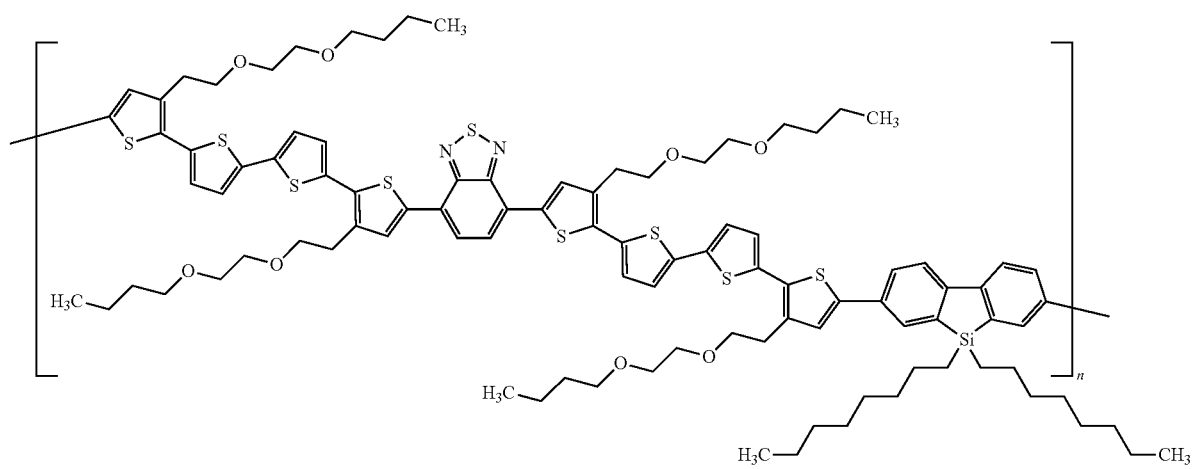

-continued
[Chem. 11]
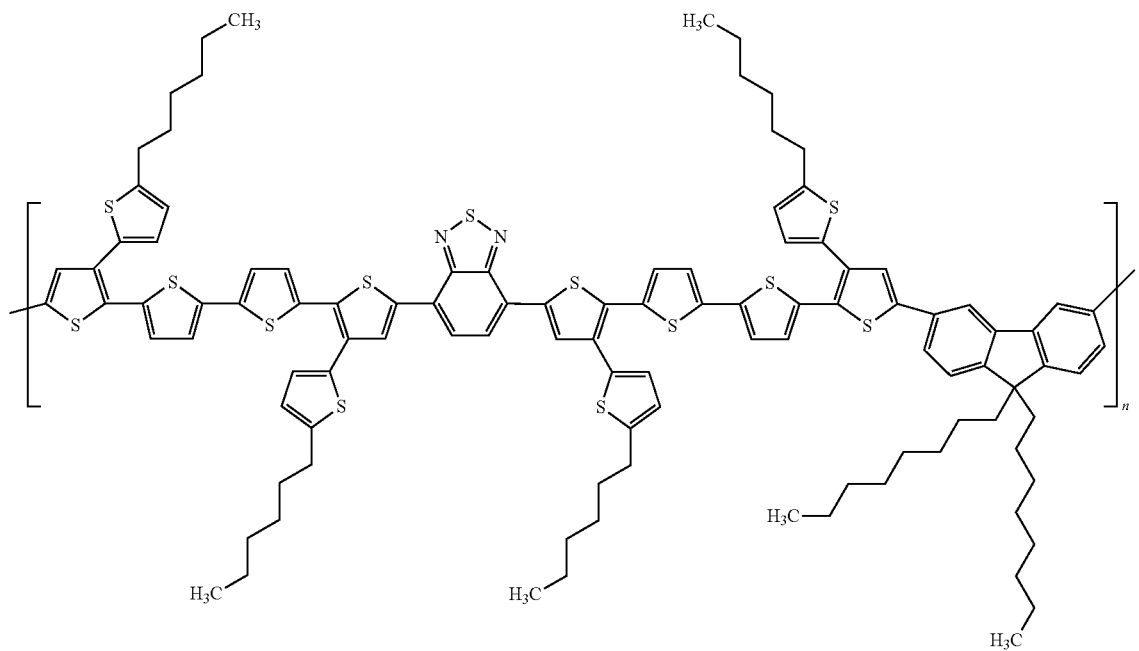
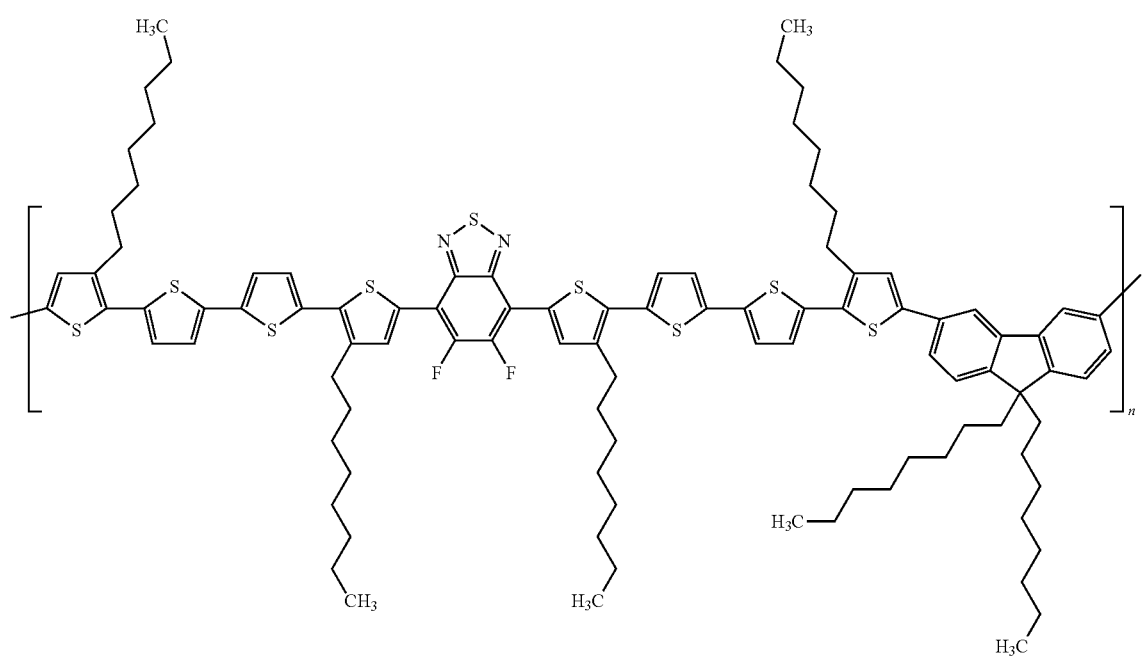

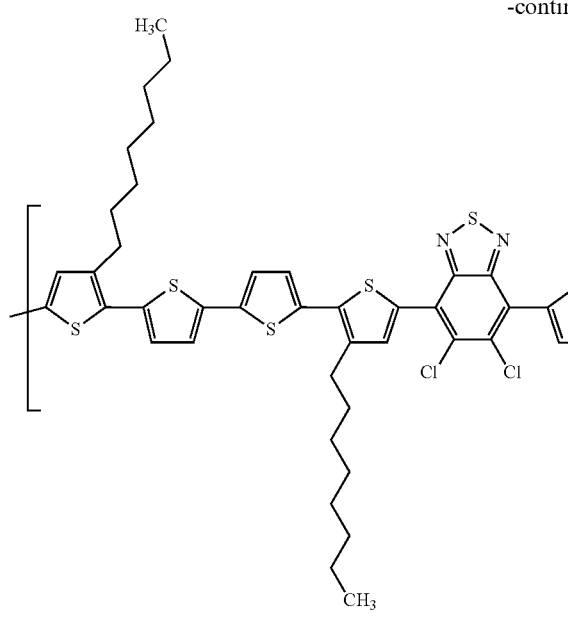
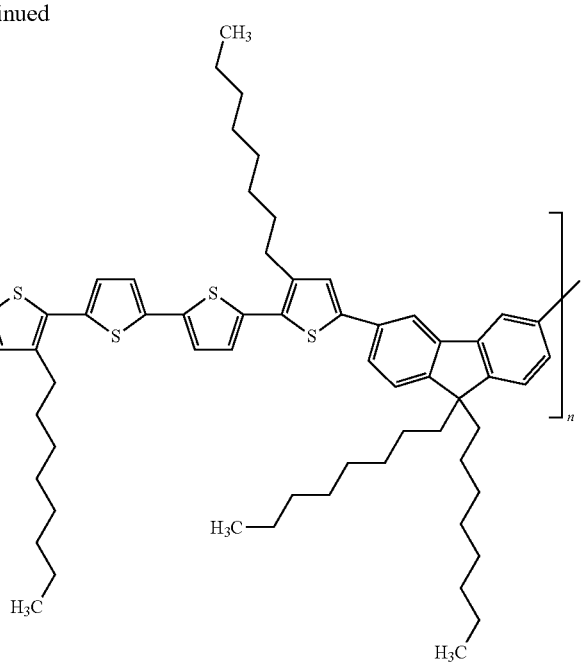

In addition, the benzothiadiazole compound having a structure represented by the formula (1) can be synthesized, for example, by a technique similar to a method described in "Macromolecules", Vol. 33, pp. 9277-9288, 2000. One example is a method in which 5,5'-dibromo-2,2'-bithiophene is reacted with a 3-alkylthiophene-2-boronic acid derivative by a Suzuki coupling method using a palladium catalyst and the resulting quaterthiophene compound is lithiated and boronic acid-esterified, and the resulting product is reacted with dibromobenzothiadiazole by the Suzuki coupling method using a palladium catalyst.

The electron donating organic material may be composed of only the benzothiadiazole compound or may contain other compounds. The content of the benzothiadiazole compound contained in the electron donating organic material is preferably within a range of 1 to 100% by weight, and more preferably within a range of 10 to 100% by weight. Examples of other compounds include conjugated polymers such as polythiophene-based polymers, poly-p-phenylene vinylene-based polymers, poly-p-phenylene-based polymers, polyfluorene-based polymers, polypyrrole-based polymers, polyaniline-based polymers, polyacetylene-based polymers and polythienylene vinylene-based polymers, and low molecular weight organic compounds including phthalocyanine derivatives such as $H_2$ phthalocyanine ($H_2Pc$), copper phthalocyanine (CuPc) and zinc phthalocyanine (ZnPc), porphyrin derivative, triarylamine derivatives such as N,N'-diphenyl-N,N'-di(3-methylphenyl)-4,4'-diphenyl-1,1'-diamine (TPD) and N,N'-dinaphthyl-N,N'-diphenyl-4,4'-diphenyl-1,1'-diamine (NPD), carbazole derivatives such as 4,4'-di(carbazol-9-yl)biphenyl (CBP), oligothiophene derivatives (terthiophene, quaterthiophene, sexithiophene, octithiophene, and the like).

The benzothiadiazole compound shows electron donating properties (p-type semiconductor properties). Therefore, to obtain higher photoelectric conversion efficiency when being used for the photovoltaic device, it is preferable to combine the benzothiadiazole compound with an electron accepting organic material (n-type organic semiconductor). The material for photovoltaic devices contains the electron donating organic material including the benzothiadiazole compound and an electron accepting organic material.

The electron accepting organic material is an organic material exhibiting n-type semiconductor properties. Examples thereof include 1,4,5,8-naphthalenetetracarboxylic dianhydride (NTCDA), 3,4,9,10-perylenetetracarboxylic dianhydride (PTCDA), 3,4,9,10-perylenetetracarboxylic bisbenzimidazole (PTCBI), N,N'-dioctyl-3,4,9,10-naphthyltetracarboxydiimide (PTCDI-C8H), oxazole derivatives such as 2-(4-biphenylyl)-5-(4-tert-butylphenyl)-1,3,4-oxadiazole (PBD) and 2,5-di(1-naphthyl)-1,3,4-oxadiazole (BND), triazole derivatives such as 3-(4-biphenylyl)-4-phenyl-5-(4-tert-butylphenyl)-1,2,4-triazole (TAZ), phenanthroline derivatives, phosphine oxide derivatives, fullerene compounds (unsubstituted compounds such as $C_{60}$, $C_{70}$, $C_{76}$, $C_{78}$, $C_{82}$, $C_{84}$, $C_{90}$ and $C_{94}$, [6,6]-phenyl C61 butyric acid methyl ester ([6,6]-PCBM), [5,6]-phenyl C61 butyric acid methyl ester ([5,6]-PCBM), [6,6]-phenyl C61 butyric acid hexyl ester ([6,6]-PCBH), [6,6]-phenyl C61 butyric acid dodecyl ester ([6,6]-PCBD), phenyl C71 butyric acid methyl ester ($PC_{70}BM$), phenyl C85 butyric acid methyl ester ($PC_{84}BM$), and the like), carbon nanotube (CNT), and derivatives (CN-PPV) formed by introducing a cyano group into a poly-p-phenylene vinylene-based polymer. In particular, fullerene compounds are preferably used because they are high in charge separation rate and electron transfer rate. Among the fullerene compounds, $C_{70}$ derivatives (for example, the above-mentioned $PC_{70}BM$) are more preferred because they are excellent in a light absorption property and can achieve higher photoelectric conversion efficiency.

The proportions (weight fractions) of the electron donating organic material and the electron accepting organic material in the material for photovoltaic devices are not particularly limited, but it is preferable that the weight fraction of the electron donating organic material : the electron accepting organic material be within a range of from 1:99 to 99:1, more preferably be within a range of from 10:90 to 90:10, and furthermore preferably be within a range of from 20:80 to 60:40. It is preferable that the electron donating organic material and the electron accepting organic material be used after being mixed.

The mixing method is not particularly limited, it may be a method in which both the materials are added to a solvent at a desired ratio and then dissolved in the solvent by, solely or in combination, heating, stirring, ultrasonic irradiation, and the like. It is noted that when a material for photovoltaic devices forms single organic semiconductor layer as described below, the above-mentioned proportions are the proportions of the electron donating organic material and the electron accepting organic material contained in the layer, whereas when an organic semiconductor layer has a layered structure including two or more layers, the proportions mean the proportions of the electron donating organic material and the electron accepting organic material contained throughout the organic semiconductor layer.

To improve the photoelectric conversion efficiency more, it is preferable to remove impurities which will serve as a trap of a carrier, as much as possible. While in the method for removing impurities from the benzothiadiazole compound described above, the electron donating organic material containing the benzothiadiazole compound and the electron accepting organic material is not particularly limited, a column chromatography method, a recrystallization method, a sublimation method, a reprecipitation method, a Soxhlet extraction method, a molecular weight fractionating method based on GPC (gel permeation chromatography), a filtration method, an ion exchange method, a chelation method, and the like can be used. Generally, the column chromatography method, the recrystallization method and the sublimation method are preferably used for the purification of low molecule weight organic materials. On the other hand, in the purification of high molecular weight materials, the reprecipitation method, the Soxhlet extraction method, and the molecular weight fractionating method based on GPC (gel permeation chromatography) are preferably used when removing low molecular weight components. When removing metal components, the reprecipitation method, the chelation method and the ion exchange method are preferably used. These methods may be used in combination of two or more.

Next, the photovoltaic device will be described. The photovoltaic device has at least a positive electrode and a negative electrode and also has a material for photovoltaic devices therebetween. FIG. 1 is a schematic diagram showing one example of the photovoltaic device. In FIG. 1, symbol 1 indicates a substrate. Symbol 2 indicates a positive electrode, and symbol 3 indicates an organic semiconductor layer containing the material for photovoltaic devices. Symbol 4 indicates a negative electrode.

Figure 2:
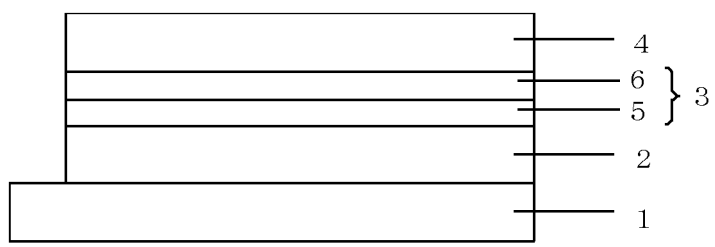
FIG. 2 is a schematic diagram showing another aspect of the photovoltaic device.

The organic semiconductor layer 3 contains the material for photovoltaic devices. That is, the organic semiconductor layer 3 contains the electron donating organic material and the electron accepting organic material. These materials may be mixed or may be layered. When these materials are mixed, the electron donating organic material and the electron accepting organic material are compatible with each other at the molecular level or are phase-separated. While the phase separation structure is not particularly limited in domain size, it ordinarily has a size of 1 nm or more and 50 nm or less. When these materials are layered, it is preferable that the layer having the electron donating organic material, which shows p-type semiconductor properties, be located on the positive electrode side, and the layer having the electron accepting organic material, which shows n-type semiconductor properties be located on the negative electrode side. One example of the photovoltaic device in which an organic semiconductor layer 3 is laminated is shown in FIG. 2. Symbol 5 indicates a layer which contains a benzothiadiazole compound having a structure represented by formula (1) and symbol 6 indicates a layer which contains an electron accepting organic material. The organic semiconductor layer is preferably 5 nm to 500 nm in thickness, and more preferably 30 nm to 300 nm in thickness. When these materials are layered, the layer containing the electron donating organic material preferably has a thickness of 1 nm to 400 nm and more preferably has a thickness of 15 nm to 150 nm, in the aforementioned thicknesses.

Further, the organic semiconductor layer 3 may contain an electron donating organic material (p-type organic semiconductor) other than the benzothiadiazole compound and the electron accepting organic materials. Examples of the electron donating organic material (p-type organic semiconductor) to be used here include compounds previously exemplified as other compounds of electron donating organic material.

In the photovoltaic device, it is preferable that the positive electrode 2 or the negative electrode 4 has light transmittance. The light transmittance of an electrode is not particularly limited as long as it is as much as an incident light reaches the organic semiconductor layer 3 to generate an electromotive force. Herein, the light transmittance is a value calculated from [transmitted light intensity $(W/m^2)$/incident light intensity $(W/m^2)$]×100(%). The thickness of the electrode, which has only to be within a range such that the film can have both light transmittance and conductivity and which may vary depending upon the electrode material, is preferably 20 to 300 nm. The other electrode is not necessarily required to be transparent if it is conductive, and its thickness is not particularly limited.

Regarding the electrode material, it is preferable to use a conductive material with a large work function for one electrode and a conductive material with a small work function for the other electrode. The electrode comprising the conductive material with a large work function serves as a positive electrode. As the conductive material with a large work function, metals such as gold, platinum, chromium and nickel, transparent metal oxides of indium, tin, and the like, and composite metal oxides (indium tin oxide (ITO), indium zinc oxide (IZO), etc.) are preferably used. The conductive material to be used for the positive electrode 2 is preferably a material which can form ohmic contact with the organic semiconductor layer 3. Furthermore, in the case of using a hole transport layer described later, the conductive material to be used for the positive electrode 2 is preferably a material which can form ohmic contact with the hole transport layer.

While the electrode comprising a conductive material with a small work function serves as a negative electrode, alkali metals and alkaline earth metals such as lithium, magnesium and calcium are used as the conductive material with a small work function. Further, tin, silver and aluminum are also preferably used. Moreover, electrodes made of alloys composed of the aforementioned metals or electrodes made of laminates of the aforementioned metals are also preferably used. Introduction of a metal fluoride such as lithium fluoride cesium fluoride in the boundary face between the negative electrode 4 and the electron transport layer enables an improvement in the extracted current. The conductive material to be used for the negative electrode 4 is preferably a material which can form ohmic contact with the organic semiconductor layer 3. Furthermore, in the case of using an electron transport layer described later, the conductive material to be used for the negative electrode 4 is preferably a material which can form ohmic contact with the electron transport layer.

As the substrate 1, a substrate, on which an electrode material or an organic semiconductor layer can be laminated in accordance with the type or the application of the photoelectric conversion material, can be used. For example, a film or a plate prepared by an arbitrary method from an inorganic material such as alkali-free glass or quartz glass or an organic material such as polyester, polycarbonate, polyolefin, polyamide, polyimide, polyphenylene sulfide, polyparaxylene, epoxy resin or fluororesin can be used. When using it while causing a light to enter from the substrate side, it is preferable that each of the substrates described above has light transmittance of about 80%.

A hole transport layer may be provided between the positive electrode 2 and the organic semiconductor layer 3. Conducting polymers such as a polythiophene-based polymers, poly-p-phenylene vinylene-based polymer and polyfluorene-based polymers and low molecular weight organic compounds showing p-type semiconductor properties such as phthalocyanine derivatives ($H_2Pc$, CuPc, ZnPc, etc.) and porphyrin derivatives are preferably used as the material which forms the hole transport layer. In particular, poly(ethylenedioxythiophene) (PEDOT), which is a polythiophene-based polymer, and a material formed by adding poly(styrenesulfonate) (PSS) to the PEDOT and are preferably used. The hole transport layer is preferably 5 nm to 600 nm, and more preferably 30 nm to 200 nm in thickness.

In the photovoltaic device, an electron transport layer may be provided between the organic semiconductor layer 3 and the negative electrode 4. The material for forming the electron transport layer is not particularly limited, but the organic materials showing n-type semiconductor properties, such as electron accepting organic materials (NTCDA, PTCDA and PTCDI-C8H, oxazole derivatives, triazole derivatives, phenanthroline derivatives, phosphine oxide derivatives, fullerene compounds, CNT and CN-PPV, and the like) described above, are preferably used. The electron transport layer is preferably 5 nm to 600 nm, and more preferably 30 nm to 200 nm in thickness.

Further, in the photovoltaic device, two or more organic semiconductor layers may be layered (configured in a tandem form) with one or more intermediate electrodes therebetween to form a direct junction. Examples of the direct junction include a layered constitution, for example, substrate/positive electrode/first organic semiconductor layer/intermediate electrode/second organic semiconductor layer/negative electrode. By forming a laminate like this, an open circuit voltage can be improved. In addition, the hole transport layer may be provided between the positive electrode and the first organic semiconductor layer and between the intermediate electrode and the second organic semiconductor layer. Further, the hole transport layer may be provided between the first organic semiconductor layer and the intermediate electrode and between the second organic semiconductor layer and the negative electrode.

In the case of these layered constitution, it is preferable that at least one of the organic semiconductor layers contains the material for photovoltaic devices and other organic semiconductor layers contain an electron donating organic material which is different in band gap from the electron donating organic material to avoid the reduction in short-circuit current. Examples of such an electron donating organic material include, as described above, conjugated polymers such as polythiophene-based polymers, poly-p-phenylene vinylene-based polymers, poly-p-phenylene-based polymers, poly-fluorene-based polymers, polypyrrole-based polymers, polyaniline-based polymers, polyacetylene-based polymers and polythienylene vinylene-based polymers, and low molecular weight organic compounds including phthalocyanine derivatives such as $H_2$ phthalocyanine ($H_2Pc$), copper phthalocyanine (CuPc) and zinc phthalocyanine (ZnPc), porphyrin derivative, triarylamine derivatives such as N,N'-diphenyl-N,N'-di(3-methylphenyl)-4,4'-diphenyl-1,1'-diamine (TPD) and N,N'-dinaphthyl-N,N'-diphenyl-4,4'-diphenyl-1,1'-diamine (NPD), carbazole derivatives such as 4,4'-di(carbazol-9-yl)biphenyl (CBP), oligothiophene derivatives (terthiophene, quaterthiophene, sexithiophene, octithiophene, and the like). Further, a material for the intermediate electrode to be used here is preferably a material having high conductivity, and examples of the material include, as described above, metals such as gold, platinum, chromium, nickel, lithium, magnesium, calcium, tin, silver and aluminum, transparent metal oxides of indium, tin or the like, composite metal oxides (indium tin oxide (ITO), indium zinc oxide (IZO), etc.), alloys composed of the above-mentioned metals, laminates of the above-mentioned metals, poly (ethylenedioxythiophene) (PEDOT) and a material formed by adding poly(styrenesulfonate) (PSS) to the PEDOT. While the intermediate electrode preferably has light transmittance, even a material having low light transmittance such as metal can often secure sufficient light transmittance by reducing a thickness of the material.

Next, the method for producing the photovoltaic device is described. A transparent electrode such as ITO, which in this case corresponds to a positive electrode, is formed on a substrate by a sputtering method or the like. Next, a solution is prepared by dissolving the material for photovoltaic devices containing the benzothiadiazole compound and an electron accepting organic material in a solvent, and then the solution is applied onto a transparent electrode to form an organic semiconductor layer. The solvent used for this purpose is preferably an organic solvent, and examples of the organic solvent include methanol, ethanol, butanol, toluene, xylene, o-chlorophenol, acetone, ethyl acetate, ethylene glycol, tetrahydrofuran, dichloromethane, chloroform, dichloroethane, chlorobenzene, dichlorobenzene, trichlorobenzene, chloronaphthalene, dimethylformamide, dimethyl sulfoxide, N-methylpyrrolidone and γ-butyrolactone. These organic solvents may be used in combination of two or more species. Further, when the organic semiconductor layer contains a fluorous solvent (organic solvent having one or more fluorine atoms in a molecule), the photoelectric conversion efficiency can be improved more. Examples of the fluorous solvent include benzotrifluoride, hexafluorobenzene, 1,1,1,3,3,3-hexafluoro-2-propanol, perfluorotoluene, perfluorodecaline, 2-fluorobenzotrifluoride, 3-fluorobenzotrifluoride, 4-fluorobenzotrifluoride, fluorobenzene, pentafluorobenzene, 1,2,4-trifluorobenzene, 1,2,5-trifluorobenzene, 1,2-difluorobenzene, 1,3-difluorobenzene, 1,4-difluorobenzene, 2H,3H-decafluoropentane, perfluorononane, perfluorooctane, perfluoroheptane, perfluorohexane, tetradecafluoro-2-methylpentane, perfluoro(1,3-dimethylcyclohexane), perfluoromethylcyclohexane, perfluorotriallylamine, perfluorotributylamine, and perfluorotriethylamine. Among these, benzotrifluoride is preferably used. The content of the fluorous solvent is preferably 0.01 to 20% by volume, and more preferably 0.1 to 5% by volume with respect to the amount of all organic solvents. Further, the content of the fluorous solvent is preferably 0.01 to 30% by weight, and more preferably 0.4 to 4% by weight with respect to the amount of all organic solvents.

When an organic semiconductor layer is formed by mixing the electron donating organic material and the electron accepting organic material, a solution is prepared by adding the electron donating organic material and the electron accepting organic material at a desired ratio to a solvent and dissolving them in the solvent with a technique such as heating, stirring or ultrasonic irradiation, and then the resulting solution is applied onto a transparent electrode. In this case, it is also possible to improve the photoelectric conversion efficiency of the photovoltaic device by using a mixture of two or more solvents. The reason for this is likely that the phase separations in the electron donating organic material and the electron accepting organic material take place at nano level to produce carrier paths which serves as a passage of an electron and a hole. With respect a combination of the solvents to be mixed, an optimal combination of the solvents can be selected according to the types of the electron donating organic material and the electron accepting organic material to be used. When the electron donating organic material is used, a preferable combination of the solvents to be mixed includes a combination of chloroform and chlorobenzene of the above-mentioned solvents. In this case, it is preferred that the volume mixing ratio between chloroform and chlorobenzene is within a range of from 5:95 to 95:5 and the weight mixing ratio is within a range of from 6.65:93.35 to 96.26:3.74. It is more preferred that the volume mixing ratio is within a range of from 10:90 to 90:10 and the weight mixing ratio is within a range of from 12.21:87.79 to 92.41:7.59. Further, when an organic semiconductor layer is formed by laminating the electron donating organic material and the electron accepting organic material, a solution of the electron donating organic material, for example, is applied to form a layer containing the electron donating organic material and then a solution of the electron accepting organic material is applied to form a layer. When the electron donating organic material and the electron accepting organic material are low molecular weight substances having a molecular weight of about 1000 or less, it is also possible to form layers of these materials by vapor deposition.

For the formation of an organic semiconductor layer, any method can be used, e.g., spin coating, blade coating, slit die coating, screen printing, bar coater coating, mold coating, a print transfer method, a dipping and picking method, an inkjet method, a spraying method and a vacuum deposition method. The forming method may be selected depending upon the intended characteristics of the organic semiconductor layer, e.g. film thickness control and orientation control. For example, in spin coating, it is preferable that the concentration of the electron donating organic material and the concentration of the electron accepting organic material are 1 to 20 g/l (weights of the electron donating organic material and the electron accepting organic material with respect to a volume of a solution containing the electron donating organic material, the electron accepting organic material and the solvent), and by employing these concentrations, a uniform organic semiconductor layer having a thickness of 5 to 200 nm can be obtained. The formed organic semiconductor layer may be subjected to annealing treatment under reduced pressure or under an inert atmosphere (e.g., under a nitrogen or argon atmosphere) for the purpose of removing the solvent. A preferable temperature of the annealing treatment is 40° C. to 300° C., and more preferable temperature is 50° C. to 200° C. Moreover, by performing the annealing treatment, the execution area, at which the laminated layers permeate mutually at their boundary face and come into contact with each other, increases, and consequently, it is possible to increase the short-circuit current. The annealing treatment may be performed after the formation of a negative electrode.

Next, a metal electrode such as Al, which corresponds to a negative electrode in this case, is formed on the organic semiconductor layer by a vacuum deposition method or sputtering method. When vacuum deposition is performed using a low molecular weight organic material in the electron transfer layer, it is preferable to continue to form the metal electrode while maintaining the vacuum.

When a hole transport layer is provided between a positive electrode and an organic semiconductor layer, a desired p-type organic semiconductor material (PEDOT, etc.) is applied onto the positive electrode by a spin coating method, bar coating method, casting method with a blade or the like, and then the solvent is removed by the use of a vacuum thermostat, a hot plate, or the like to form the hole transport layer. When using a low molecular weight organic material such as a phthalocyanine derivative or a porphyrin derivative, it is also possible to apply a vacuum deposition method using a vacuum deposition machine.

When an electron transport layer is provided between an organic semiconductor layer and a negative electrode, a desired n-type organic semiconductor material (fullerene derivative, etc.) is applied onto the organic semiconductor layer by a spin coating method, bar coating method, casting method with a blade, spraying or the like, and then the solvent is removed by the use of a vacuum thermostat, a hot plate, or the like to form the electron transport layer. When using a low molecular weight organic material such as a phenanthroline derivative or $C_{60}$, it is also possible to apply a vacuum deposition method using a vacuum deposition machine.

The positive electrode or the negative electrode may be pretreated with the above-mentioned fluorous solvent prior to the formation of the organic semiconductor layer, and thereby the photoelectric conversion efficiency can be more improved. When the hole transport layer or the electron transport layer is provided between the positive electrode or the negative electrode and the organic semiconductor layer, the hole transport layer or the electron transport layer may be pretreated with the fluorous solvent. A method of pretreatment is not particularly limited as long as it is a method in which the electrode is brought into direct contact with the fluorous solvent, and examples of the method include a method in which the fluorous solvent is applied onto the electrode, and a method in which the electrode is exposed to a vapor of the fluorous compound. Examples of the method for applying the fluorous solvent include spin coating, blade coating, slit die coating, screen printing, bar coater coating, a dipping and picking method, an inkjet method, a spraying method and a vacuum deposition method.

EXAMPLES

Our materials and devices will be hereafter described more specifically on the basis of examples. However, this disclosure is not limited to the examples. Compounds expressed by an abbreviation among the compounds used in the example are shown below.

ITO: indium tin oxide
PEDOT: poly(ethylenedioxythiophene)
PSS: poly(styrenesulfonate)
$PC_{70}BM$: phenyl C71 butyric acid methyl ester
LiF: lithium fluoride
Eg: band gap
HOMO: highest occupied molecular orbital
$I_{SC}$: short-circuit current density
$V_{OC}$: open circuit voltage FF: fill factor
η: photoelectric conversion efficiency For the $^1$H-NMR measurement was used an FT-NMR analyzer (JEOL JNM-EX270 manufactured by JEOL Ltd.). Average molecular weights (a number average molecular weight and a weight average molecular weight) were determined by the use of the absolute calibration method using a GPC analyzer (a high performance GPC apparatus HLC-8220GPC manufactured by TOSOH Corp. in which chloroform was caused to pass). The polymerization degree n was calculated by the following formula.

Polymerization degree $n$=[(Weight average molecular weight)/(Molecular weight of a monomer unit)]

Further, a wavelength at an optical absorption edge was derived from an ultraviolet visible absorption spectrum (measurement wavelength range: 300 to 900 nm) of a thin film obtained by measuring a thin film formed on a glass in a thickness of about 60 nm by the use of a spectrophotometer of U-3010 type manufactured by Hitachi, Ltd. A band gap (Eg) was calculated from a wavelength at an optical absorption edge using the formula described above. In addition, the thin film was formed by a spin coating method using chloroform as a solvent.

The level of the highest occupied molecular orbital (HOMO) was measured by analyzing, with a surface analyzing apparatus (an atmospheric type ultraviolet photoelectron spectrometer AC-1, manufactured by RIKENKIKI Co., Ltd.), a thin film formed on an ITO glass in a thickness of about 60 nm. In addition, the thin film was formed by a spin coating method using chloroform as a solvent.

Synthesis Example 1

Compound A-1 was synthesized by the method illustrated in Scheme 1.

[Chem. 12]

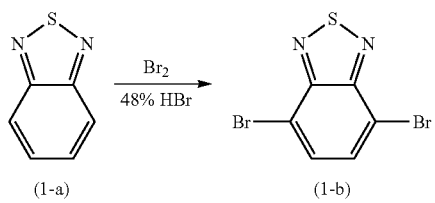

(1-a)      (1-b)

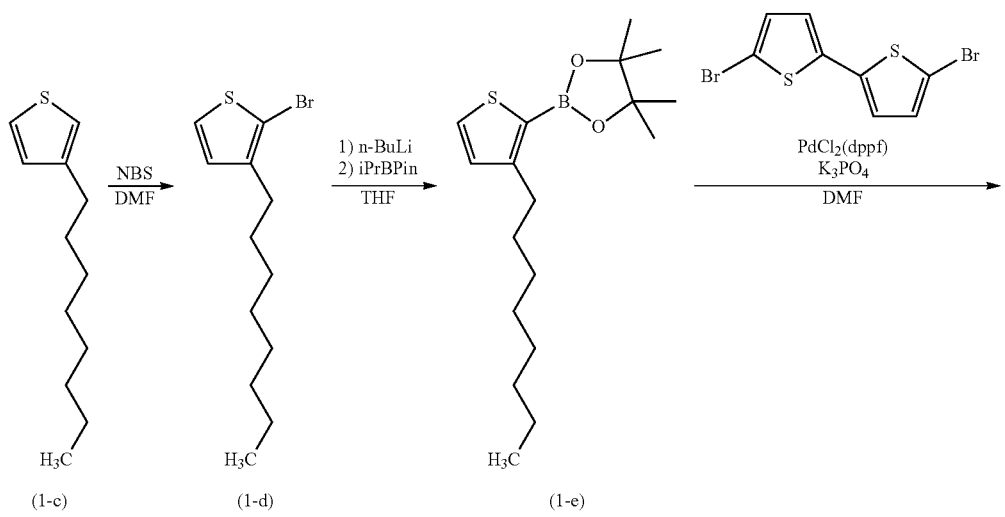

(1-c)      (1-d)      (1-e)

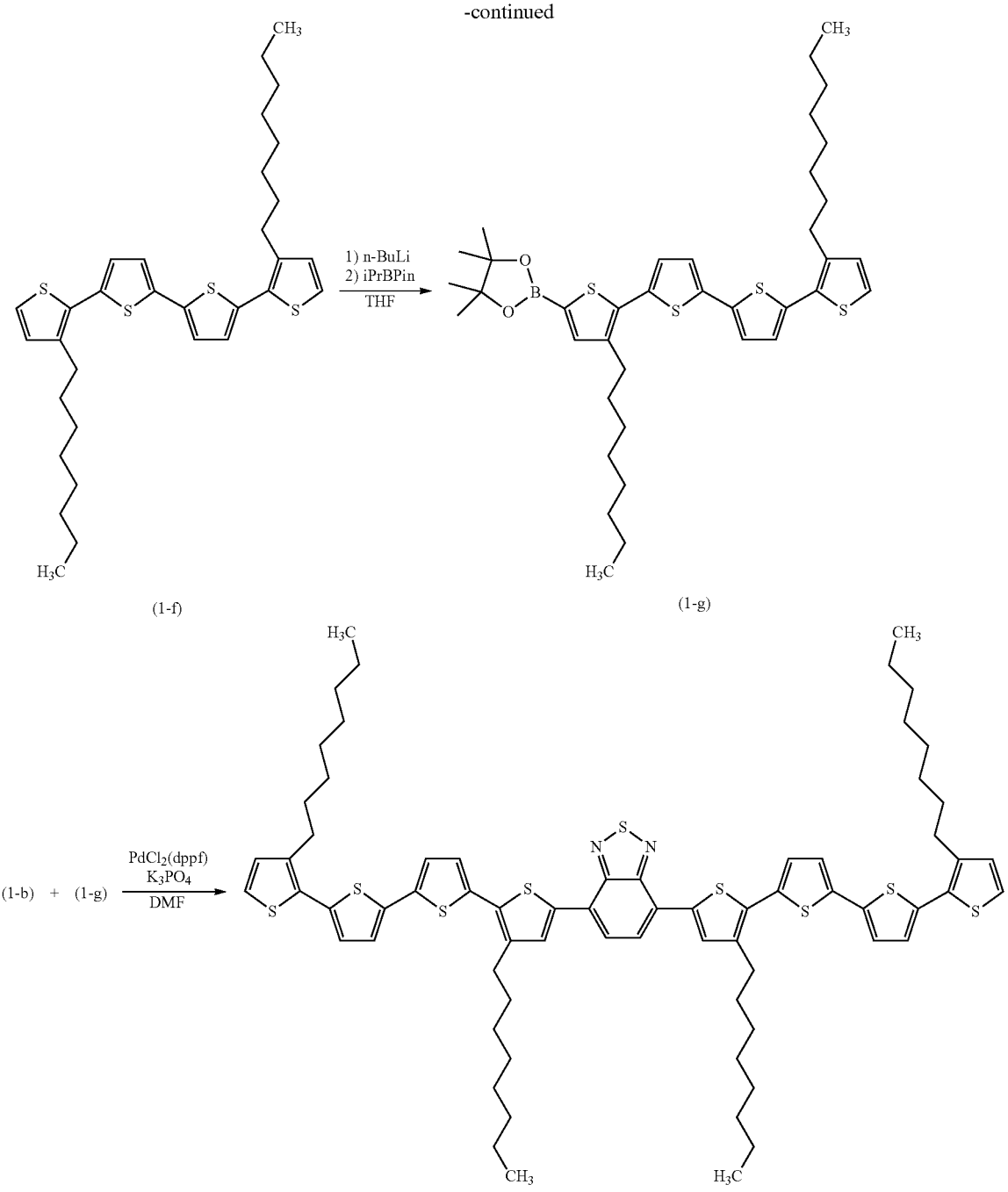

To 150 ml of 48% hydrobromic acid (produced by Wako Pure Chemical Industries, Ltd.) were added 4.3 g of compound (1-a) (produced by Tokyo Chemical Industry Co., Ltd.) and 10 g of bromine (produced by Wako Pure Chemical Industries, Ltd.), and the resulting mixture was stirred at 120° C. for 3 hours. After cooling the mixture to room temperature, precipitated solid was separated by filtration by a glass filter, and then washed with 1000 ml of water and 100 ml of acetone. The resulting solid was dried in vacuum at 60° C. to obtain 6.72 g of compound (1-b).

In 100 ml of dimethylformamide (produced by Kishida Chemical Co., Ltd.) was dissolved 10.2 g of compound (1-c) (produced by Tokyo Chemical Industry Co., Ltd.), and then 9.24 g of N-bromosuccinimide (produced by Wako Pure Chemical Industries, Ltd.) was added, and the resulting mixture was stirred under a nitrogen atmosphere at room temperature for 3 hours. To the resulting solution were added 200 ml of water, 200 ml of n-hexane and 200 ml of dichloromethane. Then, an organic layer was fractionated, washed with 200 ml of water, and then dried with magnesium sulfate. The resulting solution was purified by column chromatography (filler: silica gel, eluent: hexane) to obtain 14.4 g of compound (1-d).

In 200 ml of tetrahydrofuran (produced by Wako Pure Chemical Industries, Ltd.) was dissolved 14.2 g of the compound (1-d), and the resulting solution was cooled to −80° C. After adding 35 ml of a 1.6 M hexane solution of n-butyl lithium (produced by Wako Pure Chemical Industries, Ltd.), the temperature was raised to −50° C. and then lowered to −80° C. again. 13.6 ml of 2-isopropoxy-4,4,5,5-tetramethyl-1,3,2-dioxaborolane (produced by Wako Pure Chemical Industries, Ltd.) was added, and the temperature of the resulting mixture was raised to room temperature and the mixture was stirred under a nitrogen atmosphere for 4 hours. To the resulting solution were added 200 ml of a 1 N aqueous solution of ammonium chloride and 200 ml of ethyl acetate. Then, an organic layer was fractionated, washed with 200 ml of water, and then dried with magnesium sulfate. The resulting solution was purified by column chromatography (filler: silica gel, eluent: hexane/dichloromethane) to obtain 14.83 g of compound (1-e).

To 200 ml of dimethylformamide (produced by Wako Pure Chemical Industries, Ltd.) were added 14.83 g of the compound (1-e) and 6.78 g of 5,5'-dibromo-2,2'-bithiophene (produced by Tokyo Chemical Industry Co., Ltd.). Under a nitrogen atmosphere, 26.6 g of potassium phosphate (produced by Wako Pure Chemical Industries, Ltd.) and 1.7 g of [bis(diphenylphosphino)ferrocene]dichloropalladium (produced by Aldrich Chemical Company, Inc.) were added and the resulting mixture was stirred at 100° C. for 4 hours. To the resulting solution were added 500 ml of water and 300 ml of ethyl acetate. Then, an organic layer was fractionated, washed with 500 ml of water, and then dried with magnesium sulfate. The resulting solution was purified by column chromatography (filler: silica gel, eluent: hexane) to obtain 4.53 g of compound (1-f).

In 40 ml of tetrahydrofuran (produced by Wako Pure Chemical Industries, Ltd.) was dissolved 4.53 g of the compound (1-f), and the resulting solution was cooled to −80° C. After adding 6.1 ml of a 1.6 M hexane solution of n-butyl lithium (produced by Wako Pure Chemical Industries, Ltd.), the temperature was raised to −5° C. and then lowered to −80° C. 2.3 ml of 2-isopropoxy-4,4,5,5-tetramethyl-1,3,2-dioxaborolane (produced by Wako Pure Chemical Industries, Ltd.) was added, and the temperature of the resulting mixture was raised to room temperature and the mixture was stirred under a nitrogen atmosphere for 2 hours. To the resulting solution were added 150 ml of a 1 N aqueous solution of ammonium chloride and 200 ml of ethyl acetate. Then, an organic layer was fractionated, washed with 200 ml of water, and then dried with magnesium sulfate. The resulting solution was purified by column chromatography (filler: silica gel, eluent: dichloromethane/hexane) to obtain 2.31 g of compound (1-g).

To 17 ml of dimethylformamide (produced by Wako Pure Chemical Industries, Ltd.) were added 0.498 g of the compound (1-b) and 2.31 g of the compound (1-g). Under a nitrogen atmosphere, 2.17 g of potassium phosphate (produced by Wako Pure Chemical Industries, Ltd.) and 0.14 g of [bis(diphenylphosphino)ferrocene]dichloropalladium (produced by Aldrich Chemical Company, Inc.) were added and the resulting mixture was stirred at 90° C. for 7 hours. To the resulting solution were added 200 ml of water and 100 ml of chloroform. Then, an organic layer was fractionated, washed with 200 ml of water, and then dried with magnesium sulfate. The resulting solution was purified by column chromatography (filler: silica gel, eluent: dichloromethane/hexane) to obtain 1.29 g of compound A-1. The $^1$H-NMR measurement of the compound A-1 is shown.

$^1$H-NMR (CDCl$_3$, ppm): 8.00 (s, 2H), 7.84 (s, 2H), 7.20-7.15 (m, 8H), 7.04 (d, 2H), 6.95 (d, 2H), 2.88 (t, 4H), 2.79 (t, 4H), 1.77-1.29 (m, 48H), 0.88 (m, 12H)

The wavelength at an optical absorption edge of the compound A-1 was 727 nm, the band gap (Eg) was 1.71 eV, and the level of the highest occupied molecular orbital (HOMO) was −4.90 eV.

Synthesis Example 2

Compound A-2 was synthesized by the method illustrated in Scheme 2.

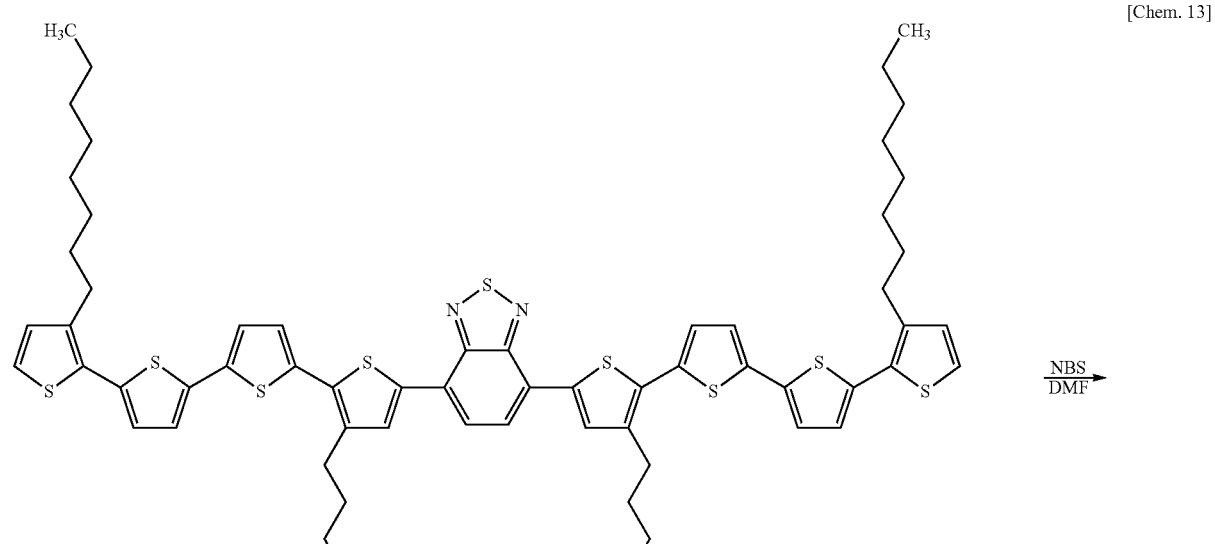

[Chem. 13]

-continued
A-1
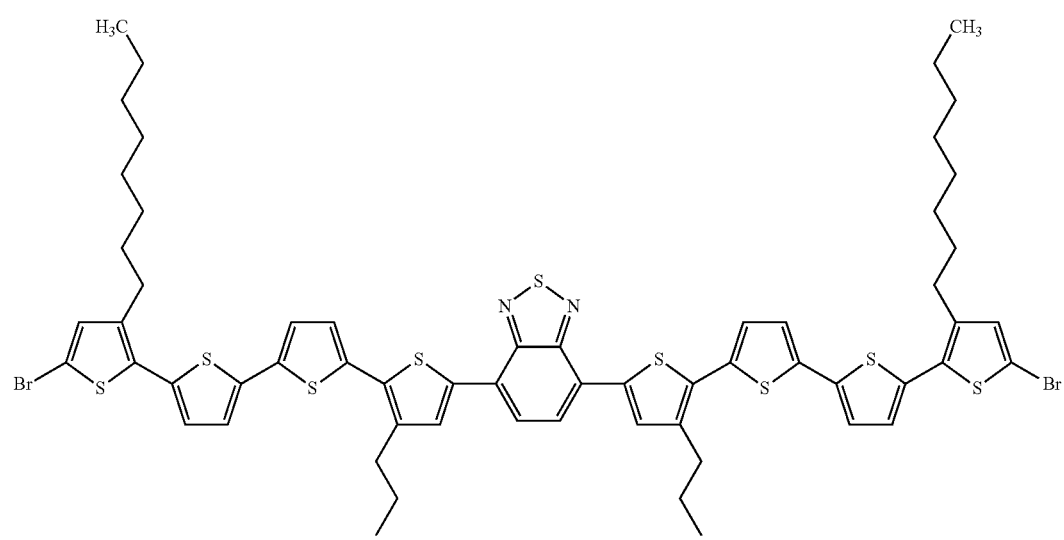
(2-a)
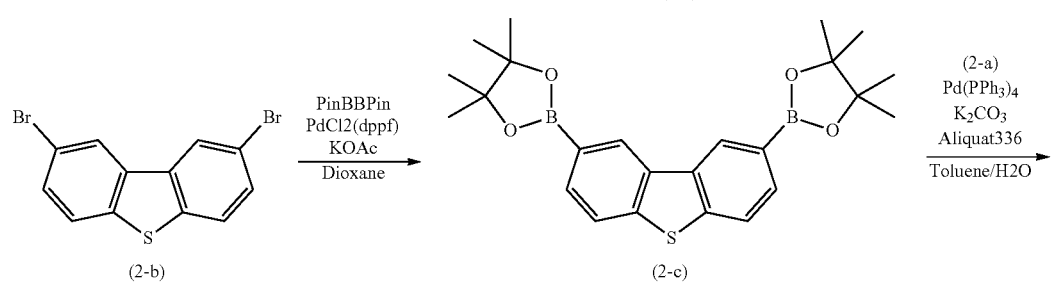

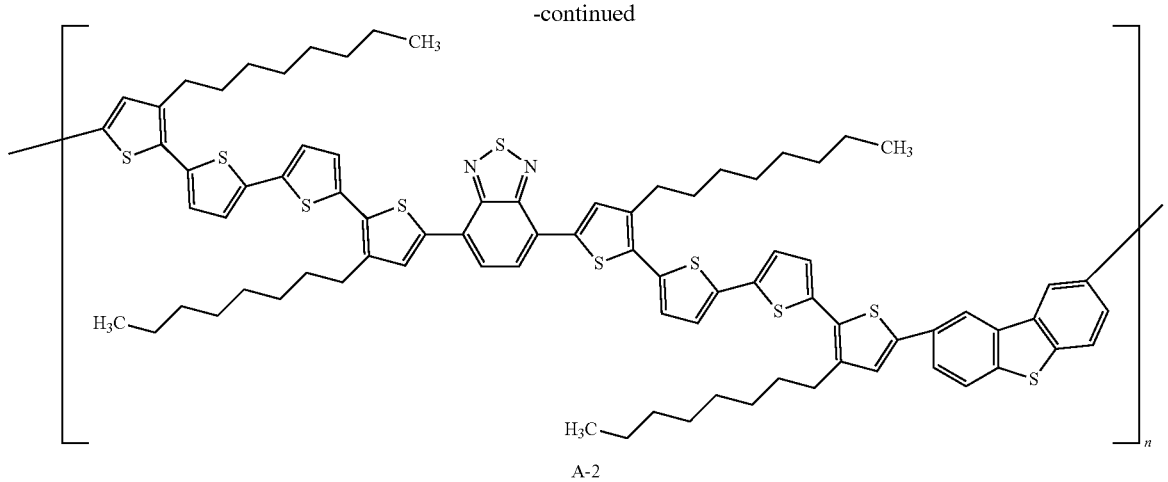

A-2

In 15 ml of chloroform (produced by NACALAI TESQUE, Inc.) was dissolved 0.734 g of the compound A-1 (produced by Tokyo Chemical Industry Co., Ltd.), and then 0.23 g of N-bromosuccinimide (produced by Tokyo Chemical Industry Co., Ltd.)/10 ml of dimethylformamide (produced by Wako Pure Chemical Industries, Ltd.) were added, and the resulting mixture was stirred under a nitrogen atmosphere at room temperature for 9 hours. To the resulting solution were added 100 ml of water and 100 ml of chloroform. Then, an organic layer was fractionated, washed with 200 ml of water, and then dried with magnesium sulfate. The resulting solution was purified by column chromatography (filler: silica gel, eluent: dichloromethane/hexane) to obtain 0.58 g of compound (2-a).

To 7 ml of 1,4-dioxane (produced by Wako Pure Chemical Industries, Ltd.) were added 0.5 g of compound (2-b) (produced by Tokyo Chemical Industry Co., Ltd.), 0.85 g of bis(pinacolato)diboron (produced by BASF Japan Ltd.) and 0.86 g of potassium acetate (produced by Wako Pure Chemical Industries, Ltd.). Under a nitrogen atmosphere, 0.21 g of [bis(diphenylphosphino)ferrocene]dichloropalladium (produced by Aldrich Chemical Company, Inc.) was added and the resulting mixture was stirred at 80° C. for 7 hours. To the resulting solution were added 100 ml of water and 100 ml of ethyl acetate. Then, an organic layer was fractionated, washed with 100 ml of water, and then dried with magnesium sulfate. The resulting solution was purified by column chromatography (filler: silica gel, eluent: dichloromethane) to obtain 57 mg of compound (2-c).

In 6 ml of toluene were dissolved 93 mg of the compound (2-a) and 19.3 mg of the compound (2-c). To this solution were added 2 ml of water, 0.18 g of potassium carbonate, 7.7 mg of tetrakis(triphenylphosphine)palladium(0) (produced by Tokyo Chemical Industry Co., Ltd.) and a drop of Aliquat 336 (produced by Aldrich Chemical Company, Inc.), and the resulting mixture was stirred under a nitrogen atmosphere at 100° C. for 25 hours. Next, 40 mg of phenylboronic acid (produced by Tokyo Chemical Industry Co., Ltd.) was added and the resulting mixture was stirred at 100° C. for 7 hours. To the resulting solution was added 50 ml of methanol, and a solid fraction produced was collected by filtration and washed with methanol, water, methanol and acetone in this order. The obtained solid was dissolved in chloroform and the resulting solution was passed through a silica gel short column (eluent: chloroform), and then concentrated to dryness to obtain 30 mg of compound A-2. The compound A-2 had the weight average molecular weight of 4376, the number average molecular weight of 3475 and the polymerization degree n of 3.1. Further, the wavelength at an optical absorption edge of the compound A-2 was 720 nm, the band gap (Eg) was 1.72 eV, and the level of the highest occupied molecular orbital (HOMO) was −5.00 eV.

Synthesis Example 3

Compound A-3 was synthesized by the method illustrated in Scheme 3.

[Chem. 14]

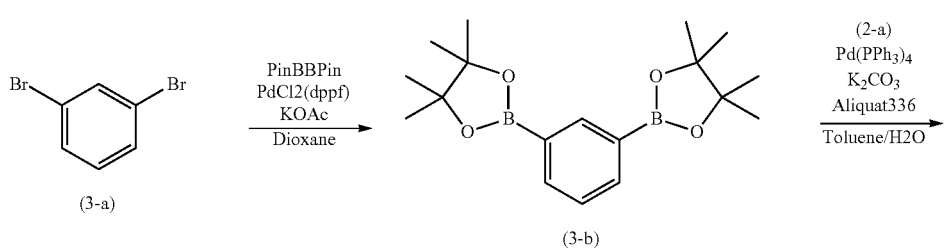

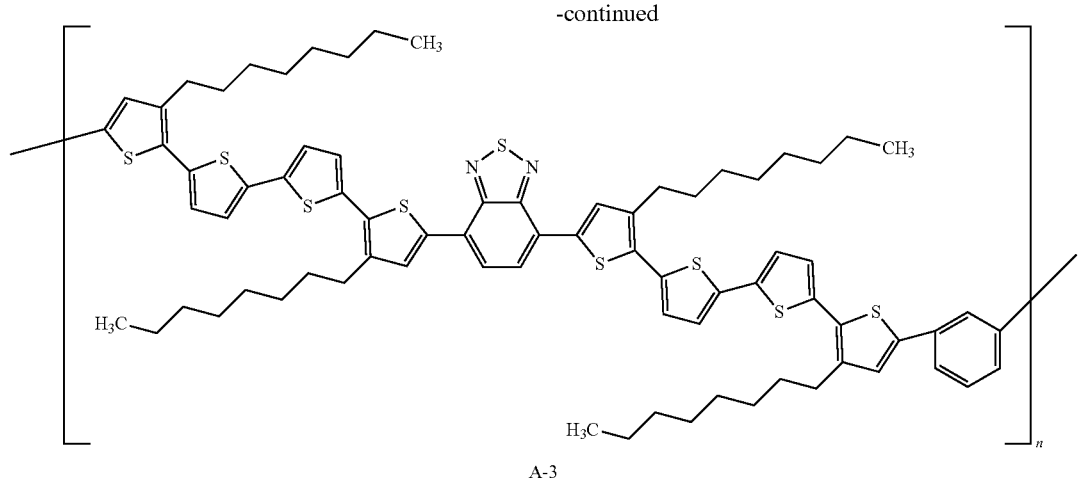

A-3

To 7 ml of 1,4-dioxane (produced by Wako Pure Chemical Industries, Ltd.) were added 0.34 g of compound (3-a) (produced by Tokyo Chemical Industry Co., Ltd.), 0.85 g of bis(pinacolato)diboron (produced by BASF Japan Ltd.) and 0.86 g of potassium acetate (produced by Wako Pure Chemical Industries, Ltd.). Under a nitrogen atmosphere, 0.21 g of [bis(diphenylphosphino)ferrocene]dichloropalladium (produced by Aldrich Chemical Company, Inc.) was added and the resulting mixture was stirred at 80° C. for 9 hours. To the resulting solution were added 100 ml of water and 100 ml of ethyl acetate. Then, an organic layer was fractionated, washed with 100 ml of water, and then dried with magnesium sulfate. The resulting solution was purified by column chromatography (filler: silica gel, eluent: dichloromethane) to obtain 167 mg of compound (3-b).

In 6 ml of toluene were dissolved 110 mg of the compound (2-a) and 17 mg of the compound (3-b). To this solution were added 2 ml of water, 0.22 g of potassium carbonate, 9 mg of tetrakis(triphenylphosphine)palladium(0) (produced by Tokyo Chemical Industry Co., Ltd.) and a drop of Aliquat 336 (produced by Aldrich Chemical Company, Inc.), and the resulting mixture was stirred under a nitrogen atmosphere at 100° C. for 45 hours. Next, 40 mg of phenylboronic acid (produced by Tokyo Chemical Industry Co., Ltd.) was added and the resulting mixture was stirred at 100° C. for 4 hours; To the resulting solution was added 50 ml of methanol, and a solid fraction produced was collected by filtration and washed with methanol, water, methanol and acetone in this order. The obtained solid was dissolved in chloroform and the resulting solution was passed through a silica gel short column (eluent: chloroform), and then concentrated to dryness to obtain 75 mg of compound A-3. The compound A-3 had the weight average molecular weight of 8691, the number average molecular weight of 5676 and the polymerization degree n of 6.7. Further, the wavelength at an optical absorption edge of the compound A-3 was 720 nm, the band gap (Eg) was 1.72 eV, and the level of the highest occupied molecular orbital (HOMO) was −5.03 eV.

Synthesis Example 4

Compound A-4 was synthesized by the method illustrated in Scheme 4.

[Chem. 15]

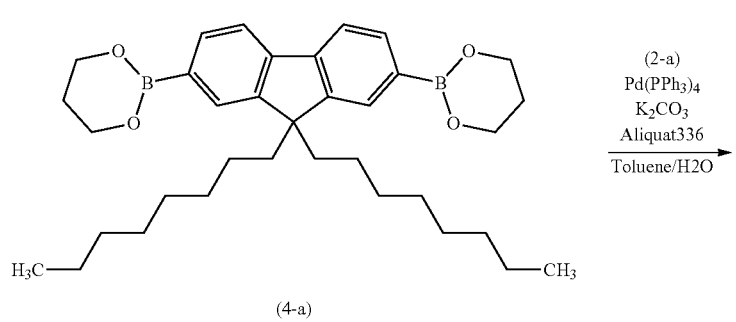

-continued

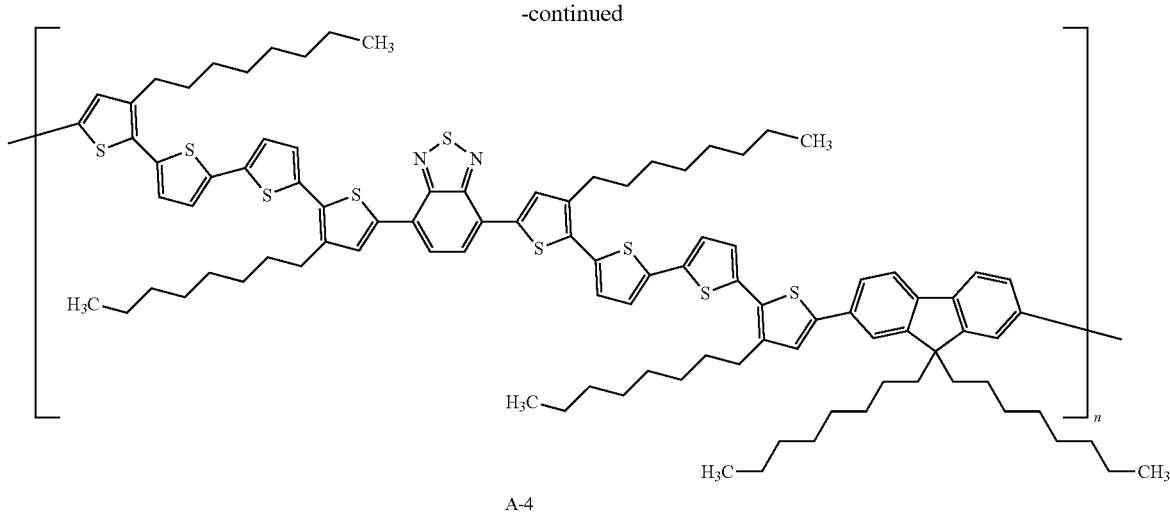

A-4

In 5 ml of toluene were dissolved 57 mg of the compound (2-a) and 18 mg of compound (4-c) (produced by Aldrich Chemical Company, Inc.). To this solution were added 2 ml of water, 0.11 g of potassium carbonate, 4.7 mg of tetrakis (triphenylphosphine)palladium(0) (produced by Tokyo Chemical Industry Co., Ltd.) and a drop of Aliquat 336 (produced by Aldrich Chemical Company, Inc.), and the resulting mixture was stirred under a nitrogen atmosphere at 100° C. for 75 hours. Next, 40 mg of phenylboronic acid (produced by Tokyo Chemical Industry Co., Ltd.) was added and the resulting mixture was stirred at 100° C. for 5 hours. To the resulting solution was added 50 ml of methanol, and a solid fraction produced was collected by filtration and washed with methanol, water, methanol and acetone in this order. The obtained solid was dissolved in chloroform and the resulting solution was passed through a silica gel short column (eluent: chloroform), and then concentrated to dryness to obtain 55 mg of compound A-4. The compound A-4 had the weight average molecular weight of 43230, the number average molecular weight of 14419 and the polymerization degree n of 26.5. Further, the wavelength at an optical absorption edge of the compound A-4 was 721 nm, the band gap (Eg) was 1.72 eV, and the level of the highest occupied molecular orbital (HOMO) was −5.14 eV.

Synthesis Example 5

Compound A-5 was synthesized by the method illustrated in Scheme 5.

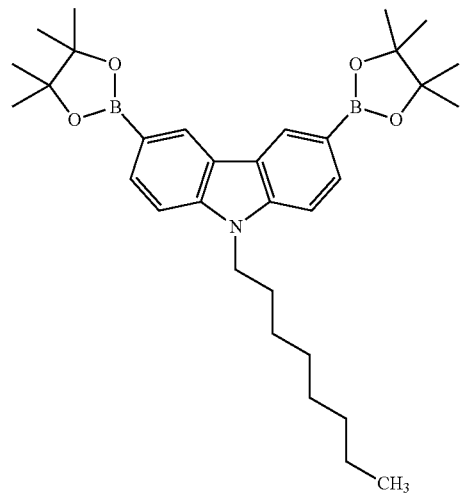

(5-d)

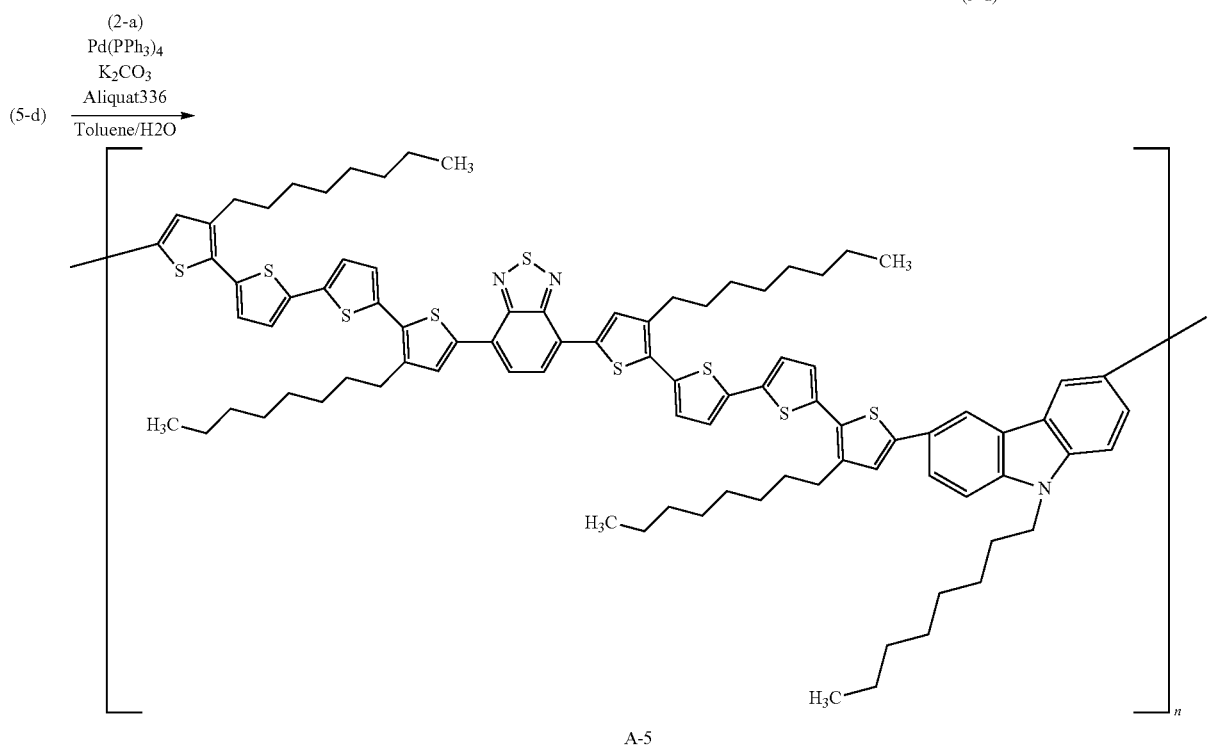

A-5

To 200 ml of acetone were added 6.33 g of compound (5-a) (produced by Tokyo Chemical Industry Co., Ltd.), 10 g of 1-iodooctane (produced by Wako Pure Chemical Industries, Ltd.) and 2.27 g of NaOH, and the resulting mixture was refluxed for 10 hours under heating under a nitrogen atmosphere. To the resulting solution were added water and hexane. Then, an organic layer was fractionated, washed with water, and then dried with magnesium sulfate. The resulting solution was purified by column chromatography (filler: silica gel, eluent: dichloromethane/hexane) to obtain 4.82 g of compound (5-b).

In 120 ml of dimethylformamide (produced by Kishida Chemical Co., Ltd.) was dissolved 4.82 g of the compound (5-b), and then 6.47 g of N-bromosuccinimide (produced by Wako Pure Chemical Industries, Ltd.) was added, and the resulting mixture was stirred under a nitrogen atmosphere at 50° C. for 10 hours. To the resulting solution were added water and dichloromethane. Then, an organic layer was fractionated, washed with water, and then dried with magnesium sulfate. The resulting solution was purified by column chromatography (filler: silica gel, eluent: dichloromethane/hexane) to obtain 6.53 g of compound (5-c).

To 18 ml of 1,4-dioxane (produced by Wako Pure Chemical Industries, Ltd.) were added 1.6 g of the compound (5-c), 2.32 g of bis(pinacolato)diboron (produced by BASF Japan Ltd.) and 2.2 g of potassium acetate (produced by Wako Pure Chemical Industries, Ltd.). Under a nitrogen atmosphere, 0.54 g of [bis(diphenylphosphino)ferrocene]dichloropalladium (produced by Aldrich Chemical Company, Inc.) was added and the resulting mixture was stirred at 80° C. for 9 hours. To the resulting solution were added 100 ml of water and 100 ml of ethyl acetate. Then, an organic layer was fractionated, washed with 100 ml of water, and then dried with magnesium sulfate. The resulting solution was purified by column chromatography (filler: silica gel, eluent: dichloromethane/hexane) to obtain 1.03 g of compound (5-d).

In 8 ml of toluene were dissolved 99 mg of the compound (2-a) and 30 mg of the compound (5-d). To this solution were added 3 ml of water, 0.195 g of potassium carbonate, 8.1 mg of tetrakis(triphenylphosphine)palladium(0) (produced by Tokyo Chemical Industry Co., Ltd.) and a drop of Aliquat 336 (produced by Aldrich Chemical Company, Inc.), and the resulting mixture was stirred under a nitrogen atmosphere at 100° C. for 92 hours. Next, 34 mg of phenylboronic acid (produced by Tokyo Chemical Industry Co., Ltd.) was added and the resulting mixture was stirred at 100° C. for 6 hours. To the resulting solution was added 50 ml of methanol, and a solid fraction produced was collected by filtration and washed with methanol, water, methanol and acetone in this order. The obtained solid was dissolved in chloroform and the resulting solution was passed through a silica gel short column (eluent: chloroform), and then concentrated to dryness to obtain 85 mg of compound A-5. The compound A-5 had the weight average molecular weight of 9380, the number average molecular weight of 5410 and the polymerization degree n of 6.2. Further, the wavelength at an optical absorption edge of the compound A-5 was 733 nm, the band gap (Eg) was 1.69 eV, and the level of the highest occupied molecular orbital (HOMO) was −4.91 eV.

Synthesis Example 6

Compound A-6 was synthesized by the method illustrated in Scheme 6.

[Chem. 17]

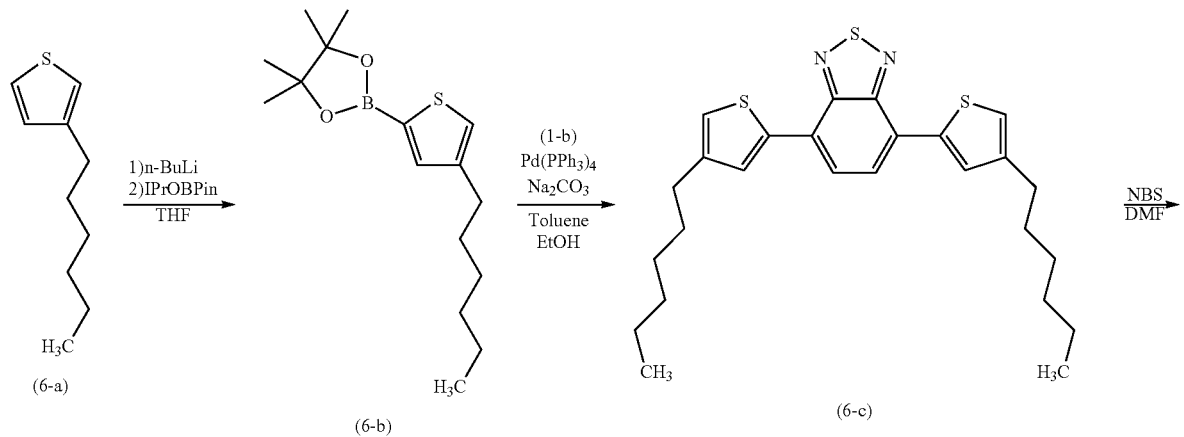

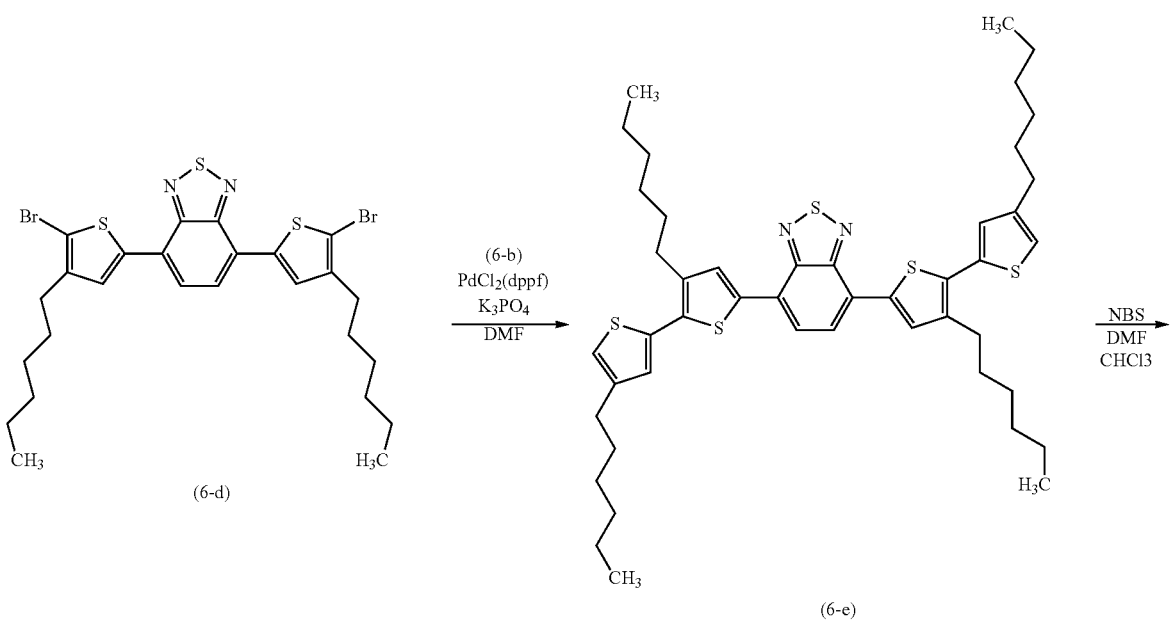

-continued
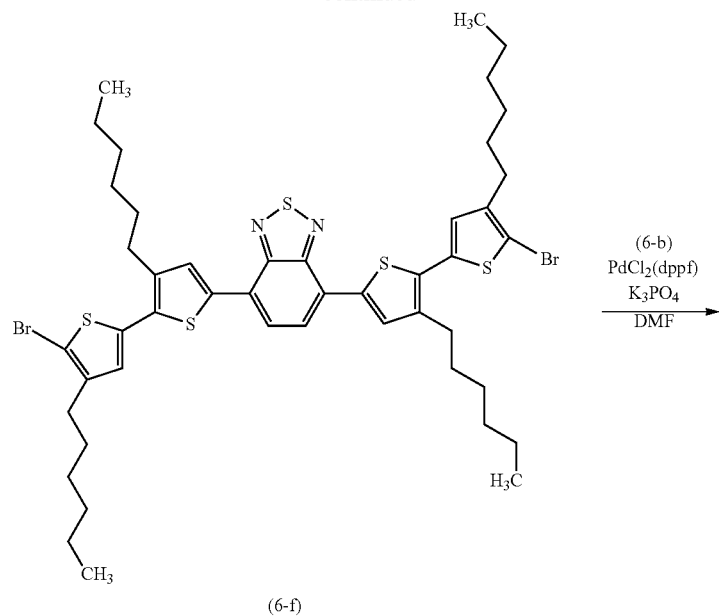
(6-f)
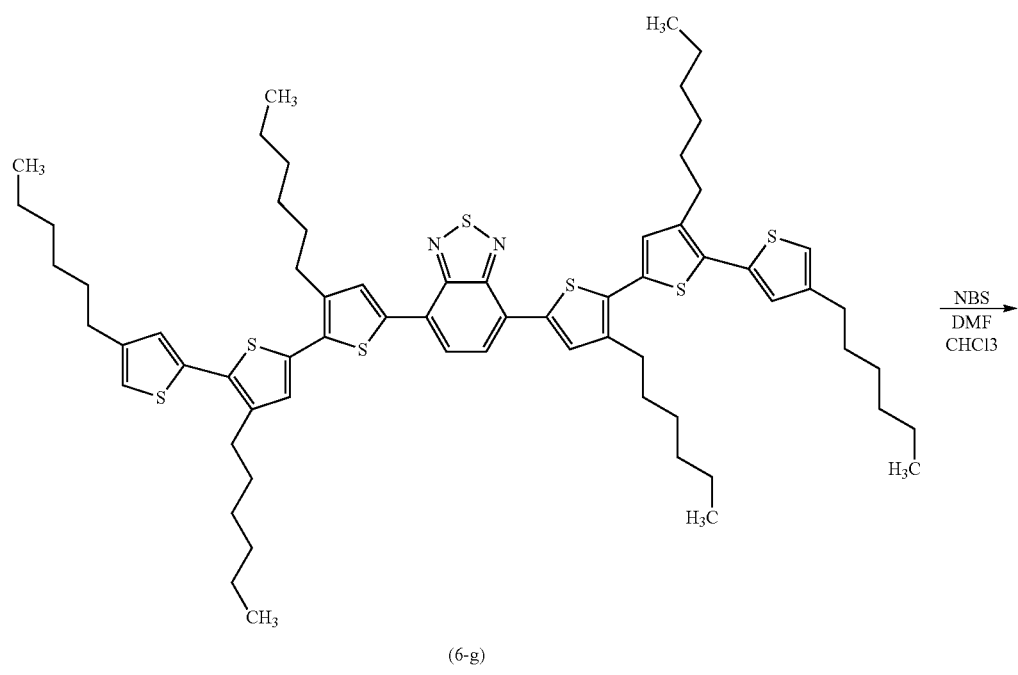
(6-g)

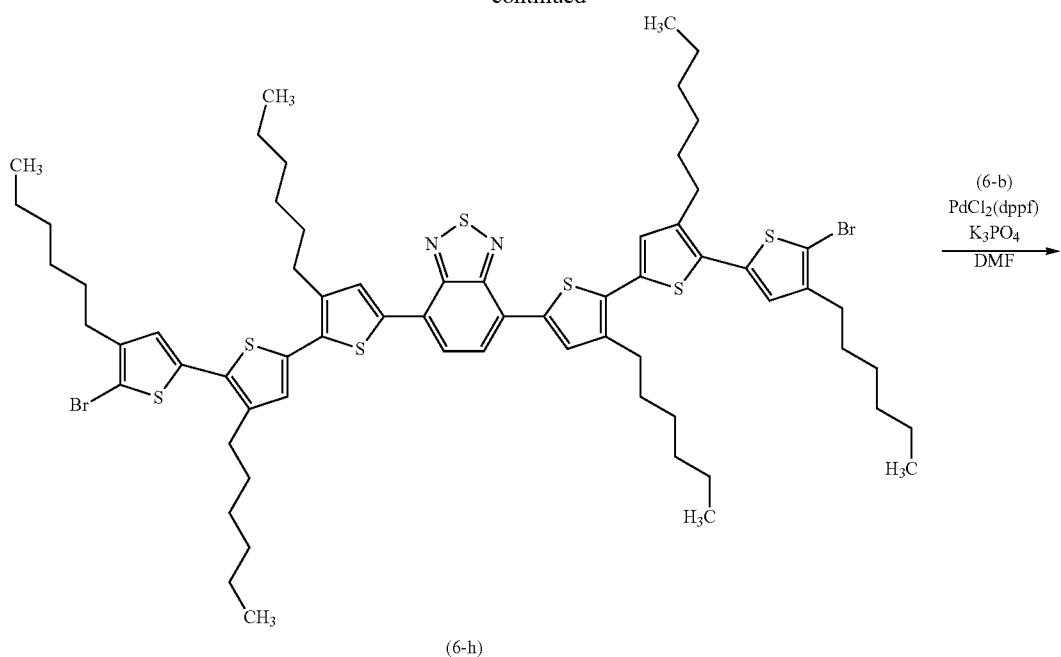
(6-h)
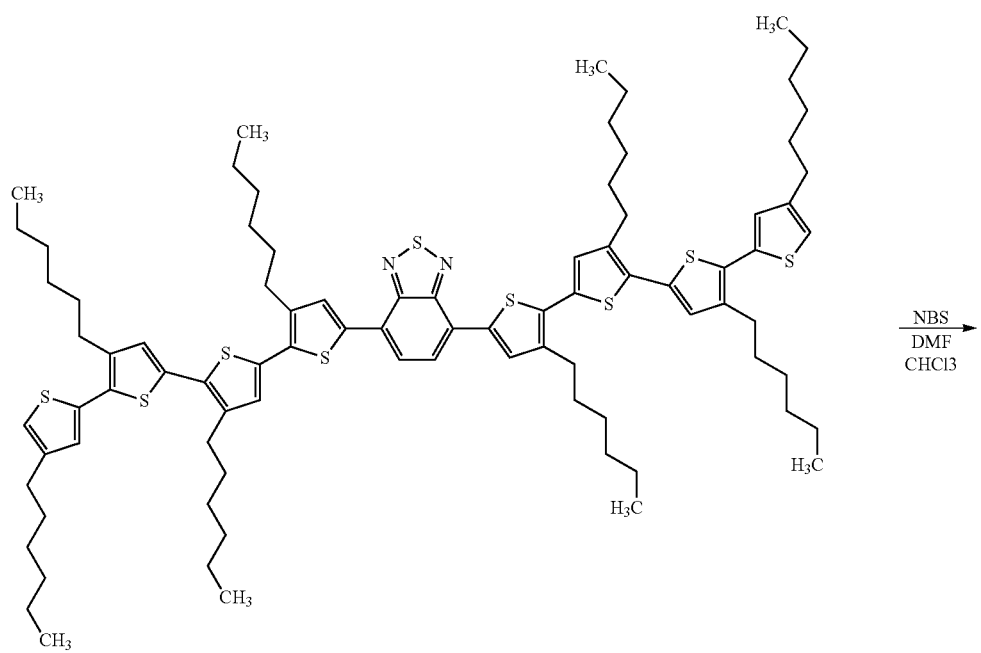
(6-i)

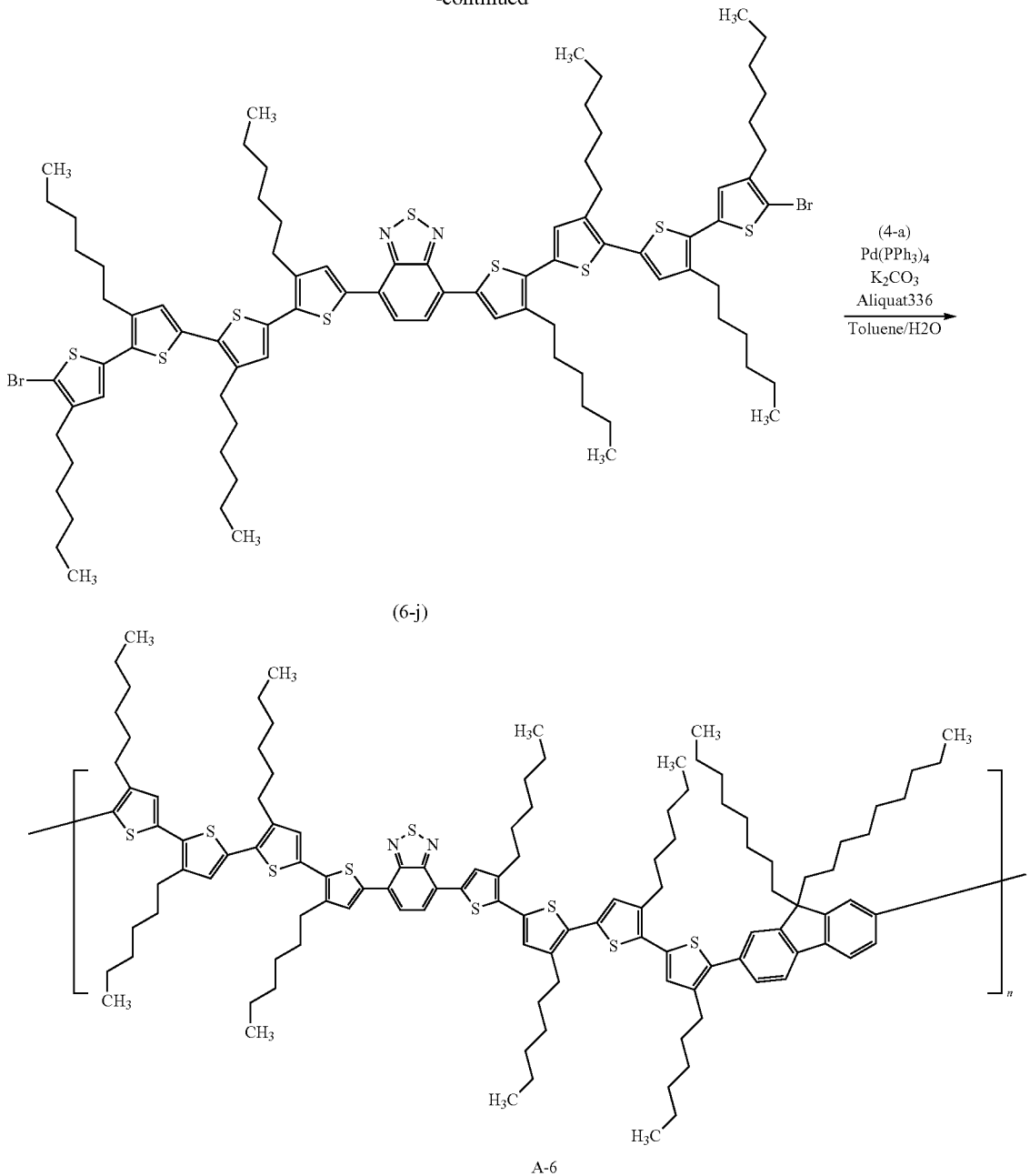

In 40 ml of tetrahydrofuran (produced by Wako Pure Chemical Industries, Ltd.) was dissolved 3 g of compound (6-a), and the resulting solution was cooled to −80° C. 12 ml of a 1.6 M hexane solution of n-butyl lithium (produced by Wako Pure Chemical Industries, Ltd.) was added and the resulting mixture was stirred for 2 hours, and then the temperature was raised to −60° C. To this was added 5.5 g of 2-isopropoxy-4,4,5,5-tetramethyl-1,3,2-dioxaborolane (produced by Wako Pure Chemical Industries, Ltd.). The temperature of the resulting mixture was raised to room temperature and the mixture was stirred under a nitrogen atmosphere for 4 hours. To the resulting solution were added 100 ml of dichloromethane and 100 ml of saturated saline. Then, an organic layer was fractionated, washed with 100 ml of water three times, and then dried with magnesium sulfate. The solvent was distilled off from the resulting solution under reduced pressure with a rotary evaporator to obtain 4.6 g of compound (6-b).

In 100 ml of toluene were dissolved 4.6 g of the compound (6-b) and 2.1 g of the compound (1-b) in Synthesis Example 1. To this solution were added 30 ml of ethanol, 30 ml of a 2M aqueous solution of sodium carbonate and 0.15 g of tetrakis (triphenylphosphine)palladium(0) (produced by Tokyo Chemical Industry Co., Ltd.), and the resulting mixture was stirred under a nitrogen atmosphere at 110° C. for 13 hours. To the resulting solution were added 100 ml of ethyl acetate and 100 ml of water, and an organic layer was fractionated. The solvent was distilled off from the resulting solution under reduced pressure with a rotary evaporator to obtain 5.8 g of compound (6-c).

In 3 ml of dimethylformamide (produced by Wako Pure Chemical Industries, Ltd.) was dissolved 5.8 g of the compound (6-c), and then 3.5 g of N-bromosuccinimide (produced by Wako Pure Chemical Industries, Ltd.) was added, and the resulting mixture was stirred under a nitrogen atmosphere at room temperature for 2 hours. To the resulting solution were added 100 ml of water and 100 ml of ethyl acetate. Then, an organic layer was fractionated, washed with 100 ml of water three times, and then dried with magnesium sulfate. The resulting solution was purified by column chromatography (filler: silica gel, eluent: dichloromethane/hexane) to obtain 1.6 g of compound (6-d).

To 10 ml of dimethylformamide were added 557 mg of the compound (6-d) and 520 mg of the compound (6-b). Under a nitrogen atmosphere, 1.13 g of potassium phosphate (produced by Wako Pure Chemical Industries, Ltd.) and 73 mg of [bis(diphenylphosphino)ferrocene]dichloropalladium (produced by Aldrich Chemical Company, Inc.) were added and the resulting mixture was stirred at 100° C. for 9 hours. To the resulting solution were added 100 ml of water and 100 ml of chloroform. Then, an organic layer was fractionated, washed with 100 ml of water, and then dried with magnesium sulfate. The resulting solution was purified by column chromatography (filler: silica gel, eluent: dichloromethane/hexane) to obtain 724 mg of compound (6-e).

In 10 ml of dimethylformamide was dissolved 724 mg g of the compound (6-e), and then 340 mg of N-bromosuccinimide (produced by Wako Pure Chemical Industries, Ltd.) was added, and the resulting mixture was stirred under a nitrogen atmosphere at room temperature for 3 hours. To the resulting solution were added 150 ml of water and 100 ml of chloroform. Then, an organic layer was fractionated, washed with 300 ml of water, and then dried with magnesium sulfate. The resulting solution was purified by column chromatography (filler: silica gel, eluent: dichloromethane/hexane) to obtain 800 mg of compound (6-f).

To 10 ml of dimethylformamide were added 800 mg of the compound (6-f) and 490 mg of the compound (6-b). Under a nitrogen atmosphere, 1.06 g of potassium phosphate (produced by Wako Pure Chemical Industries, Ltd.) and 68 mg of [bis(diphenylphosphino)ferrocene]dichloropalladium (produced by Aldrich Chemical Company, Inc.) were added and the resulting mixture was stirred at 100° C. for 5 hours. To the resulting solution were added 100 ml of water and 100 ml of chloroform. Then, an organic layer was fractionated, washed with 300 ml of water, and then dried with magnesium sulfate. The resulting solution was purified by column chromatography (filler: silica gel, eluent: dichloromethane/hexane) to obtain 672 mg of compound (6-g).

In 6 ml of chloroform was dissolved 670 mg of the compound (6-g), and then a dimethylformamide (1 ml) solution of 220 mg of N-bromosuccinimide (produced by Wako Pure Chemical Industries, Ltd.) was added, and the resulting mixture was stirred under a nitrogen atmosphere at room temperature for 7 hours. To the resulting solution were added 100 ml of water and 100 ml of chloroform. Then, an organic layer was fractionated, washed with 300 ml of water, and then dried with magnesium sulfate. The resulting solution was purified by column chromatography (filler: silica gel, eluent: dichloromethane/hexane) to obtain 797 mg of compound (6-h).

To 15 ml of dimethylformamide were added 790 mg of the compound (6-h) and 390 mg of the compound (6-b). Under a nitrogen atmosphere, 760 mg of potassium phosphate (produced by Wako Pure Chemical Industries, Ltd.) and 49 mg of [bis(diphenylphosphino)ferrocene]dichloropalladium (produced by Aldrich Chemical Company, Inc.) were added and the resulting mixture was stirred at 100° C. for 7 hours. To the resulting solution were added 50 ml of water and 50 ml of chloroform. Then, an organic layer was fractionated, washed with 300 ml of water, and then dried with magnesium sulfate. The resulting solution was purified by column chromatography (filler: silica gel, eluent: dichloromethane/hexane) to obtain 240 mg of compound (6-i).

In 5 ml of chloroform was dissolved 240 mg of the compound (6-i), and then a dimethylformamide (2 ml) solution of 610 mg of N-bromosuccinimide (produced by Wako Pure Chemical Industries, Ltd.) was added, and the resulting mixture was stirred under a nitrogen atmosphere at room temperature for 10 hours. To the resulting solution were added 100 ml of water and 50 ml of chloroform. Then, an organic layer was fractionated, washed with 300 ml of water, and then dried with magnesium sulfate. The resulting solution was purified by column chromatography (filler: silica gel, eluent: dichloromethane/hexane) to obtain 180 mg of compound (6-j).

In 7 ml of toluene were dissolved 89 mg of the compound (6-j) and 30.5 mg of the compound (4-a) in Synthesis Example 4. To this solution were added 3 ml of water, 150 mg of potassium carbonate, 6.4 mg of tetrakis(triphenylphosphine)palladium(0) (produced by Tokyo Chemical Industry Co., Ltd.) and a drop of Aliquat 336 (produced by Aldrich Chemical Company, Inc.), and the resulting mixture was stirred under a nitrogen atmosphere at 100° C. for 17 hours. Next, five drops of bromobenzene (produced by Tokyo Chemical Industry Co., Ltd.) was added and the resulting mixture was stirred at 100° C. for 12 hours. To the resulting solution was added 50 ml of methanol, and a solid fraction produced was collected by filtration and washed with methanol and acetone in this order. The obtained solid was dissolved in 100 ml of chloroform, and the resulting solution was passed through a silica gel short column (eluent: chloroform) and then concentrated to dryness, and washed with methanol and acetone in this order to obtain 20 mg of compound A-6. The compound A-6 had the weight average molecular weight of 168017, the number average molecular weight of 19085 and the polymerization degree n of 90. Further, the wavelength at an optical absorption edge of the compound A-6 was 716 nm, the band gap (Eg) was 1.73 eV, and the level of the highest occupied molecular orbital (HOMO) was −5.21 eV.

Synthesis Example 7

Compound B-2 was synthesized by the method illustrated in Scheme 7.

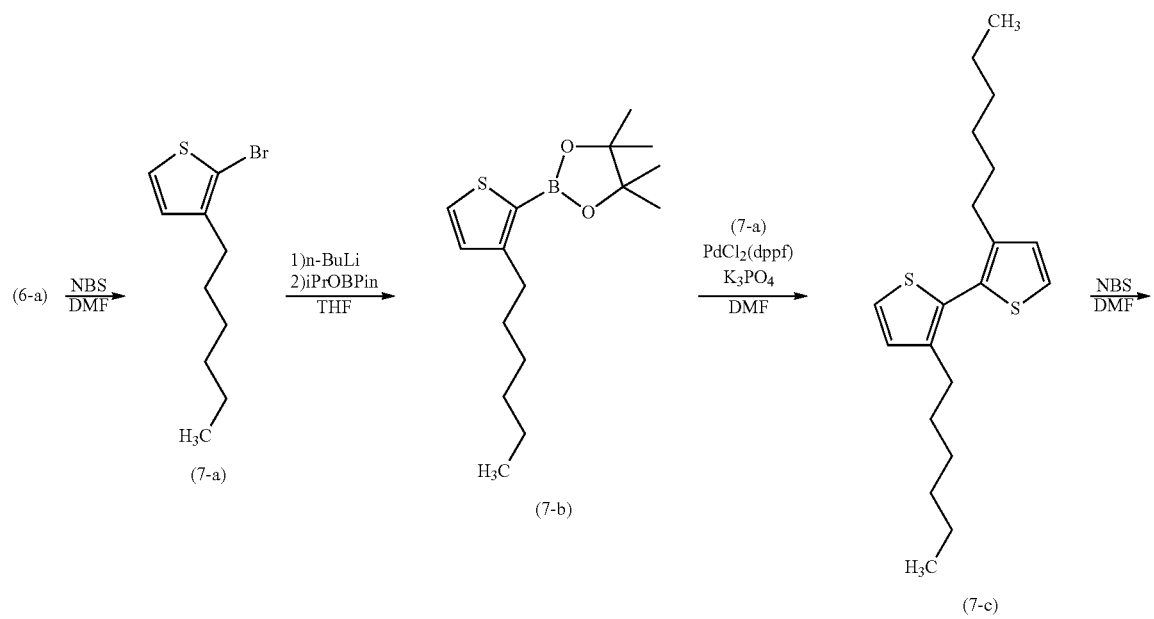
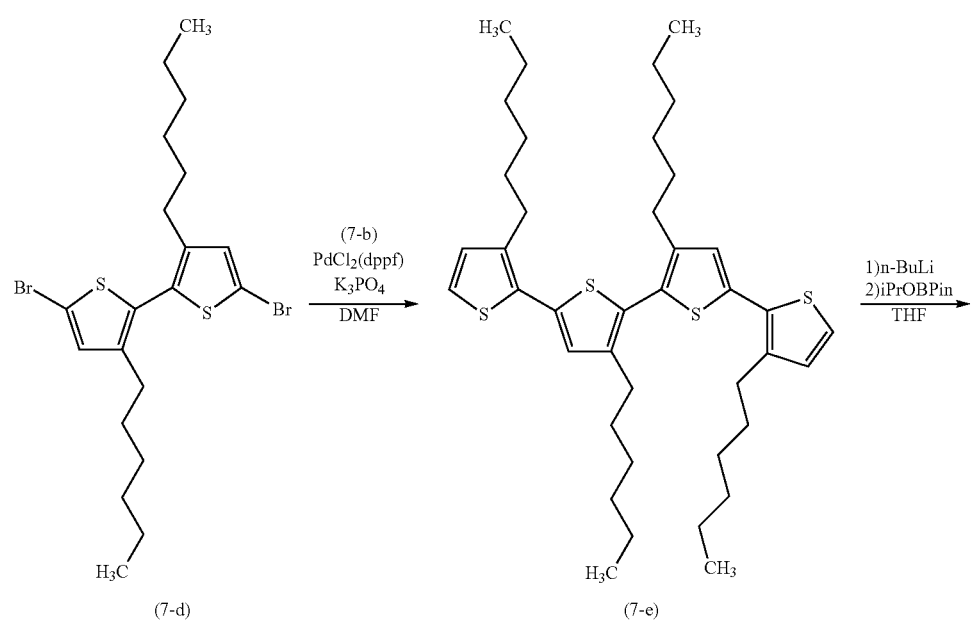

-continued
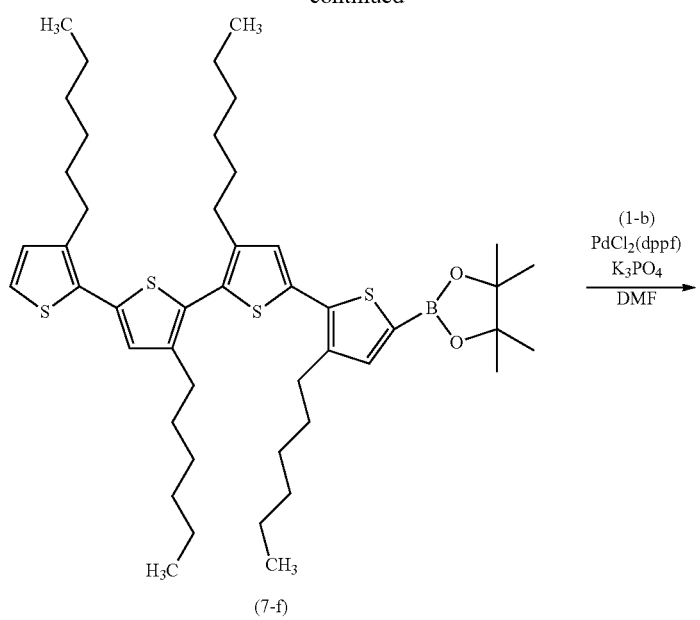
(7-f)
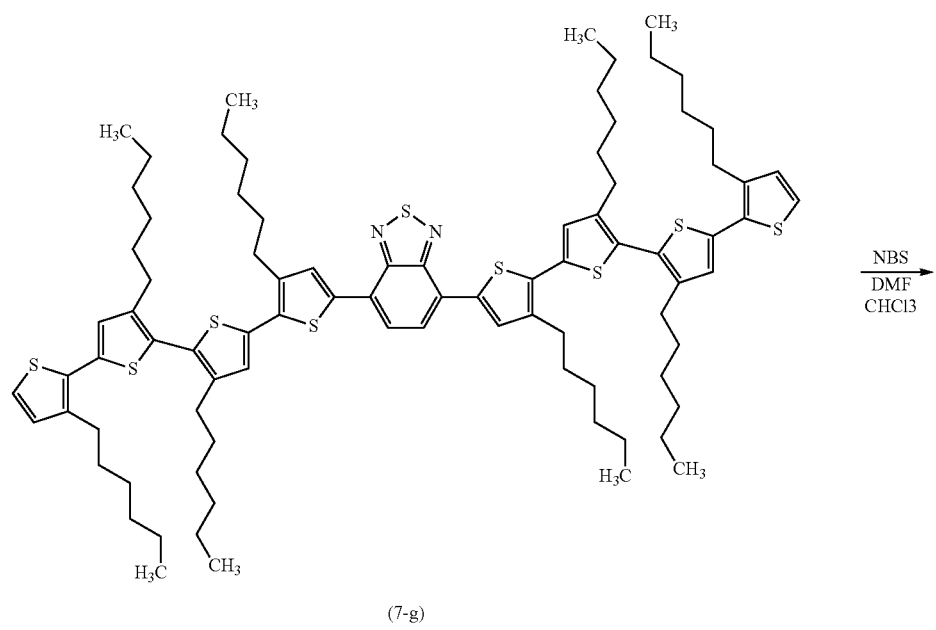
(7-g)

-continued

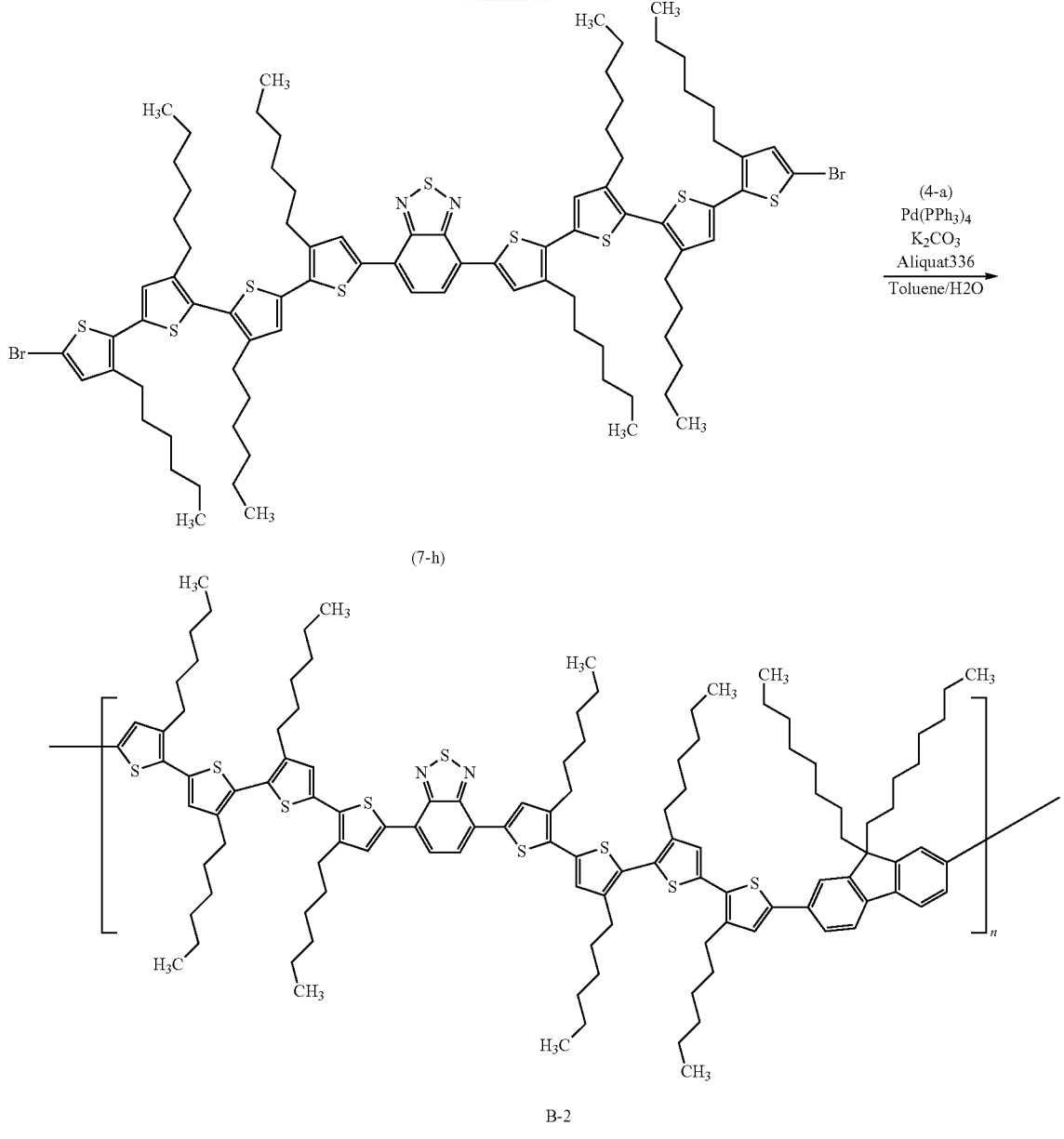

In 150 ml of dimethylformamide was dissolved 31.4 g of the compound (6-a), and then a dimethylformamide (150 ml) solution of 33.2 g of N-bromosuccinimide (produced by Wako Pure Chemical Industries, Ltd.) was added, and the resulting mixture was stirred at room temperature for 4 hours. To the resulting solution were added 500 ml of water and 300 ml of hexane. Then, an organic layer was fractionated, washed with 500 nil of water, and then dried with magnesium sulfate. The resulting solution was purified by column chromatography (filler: silica gel, eluent: hexane) to obtain 44.93 g of compound (7-a).

In 140 ml of tetrahydrofuran (produced by Wako Pure Chemical Industries, Ltd.) was dissolved 16.55 g of the compound (7-a), and the resulting solution was cooled to −90° C. After adding 44 ml of a 1.6 M hexane solution of n-butyl lithium (produced by Wako Pure Chemical Industries, Ltd.), the temperature was raised to −70° C. and then lowered to −90° C. again. 16.4 ml of 2-isopropoxy-4,4,5,5-tetramethyl-1,3,2-dioxaborolane (produced by Wako Pure Chemical Industries, Ltd.) was added, and the temperature of the resulting mixture was raised to room temperature and the mixture was stirred under a nitrogen atmosphere for 13 hours. To the resulting solution were added 500 ml of a 1 N aqueous solution of ammonium chloride and 300 ml of hexane. Then, an organic layer was fractionated, washed with 800 ml of water, and then dried with magnesium sulfate. The resulting solution was purified by column chromatography (filler: silica gel, eluent: dichloromethane/hexane) to obtain 18.73 g of compound (7-b).

To 100 ml of dimethylformamide were added 2.52 g of the compound (7-a) and 3.0 g of the compound (7-b). Under a nitrogen atmosphere, 13 g of potassium phosphate (produced by Wako Pure Chemical Industries, Ltd.) and 420 mg of [bis(diphenylphosphino)ferrocene]dichloropalladium (produced by Aldrich Chemical Company, Inc.) were added and the resulting mixture was stirred at 90° C. for 5 hours. To the resulting solution were added 200 ml of water and 100 ml of hexane. Then, an organic layer was fractionated, washed with 400 ml of water, and then dried with magnesium sulfate. The resulting solution was purified by column chromatography (filler: silica gel, eluent: hexane) to obtain 2.71 g of compound (7-c).

In 8 ml of dimethylformamide was dissolved 2.71 g of the compound (7-c), and then a dimethylformamide (16 ml) solution of 2.88 g of N-bromosuccinimide (produced by Wako Pure Chemical Industries, Ltd.) was added, and the resulting mixture was stirred at a temperature of 5 to 10° C. for 9 hours. To the resulting solution were added 150 ml of water and 100 ml of hexane. Then, an organic layer was fractionated, washed with 300 ml of water, and then dried with magnesium sulfate. The resulting solution was purified by column chromatography (filler: silica gel, eluent: hexane) to obtain 3.76 g of compound (7-d).

To 70 ml of dimethylformamide were added 3.76 g of the compound (7-d) and 4.71 g of the compound (7-b). Under a nitrogen atmosphere, 19.4 g of potassium phosphate (produced by Wako Pure Chemical Industries, Ltd.) and 310 mg of [bis(diphenylphosphino)ferrocene]dichloropalladium (produced by Aldrich Chemical Company, Inc.) were added and the resulting mixture was stirred at 90° C. for 9 hours. To the resulting solution were added 500 ml of water and 200 ml of hexane. Then, an organic layer was fractionated, washed with 300 ml of water, and then dried with magnesium sulfate. The resulting solution was purified by column chromatography (filler: silica gel, eluent: hexane) to obtain 4.24 g of compound (7-e).

In 27 ml of tetrahydrofuran (produced by Wako Pure Chemical Industries, Ltd.) was dissolved 3.65 g of the compound (7-e), and the resulting solution was cooled to −80° C. After adding 4.1 ml of a 1.6 M hexane solution of n-butyl lithium (produced by Wako Pure Chemical Industries, Ltd.), the temperature was raised to 5° C. and then lowered to −80° C. again. 1.6 ml of 2-isopropoxy-4,4,5,5-tetramethyl-1,3,2-dioxaborolane (produced by Wako Pure Chemical Industries, Ltd.) was added, and the temperature of the resulting mixture was raised to room temperature and the mixture was stirred under a nitrogen atmosphere for 2 hours. To the resulting solution were added 200 ml of a 1 N aqueous solution of ammonium chloride and 200 ml of hexane. Then, an organic layer was fractionated, washed with 400 ml of water, and then dried with magnesium sulfate. The resulting solution was purified by column chromatography (filler: silica gel, eluent: dichloromethane/hexane) to obtain 2.17 g of compound (7-f).

To 50 ml of dimethylformamide were added 2.17 g of the compound (7-f) and 400 mg of the compound (1-b) in Synthesis Example 1. Under a nitrogen atmosphere, 3.48 g of potassium phosphate (produced by Wako Pure Chemical Industries, Ltd.) and 220 mg of [bis(diphenylphosphino)ferrocene]dichloropalladium (produced by Aldrich Chemical Company, Inc.) were added and the resulting mixture was stirred at 100° C. for 6 hours. To the resulting solution were added 200 ml of water and 200 ml of dichloromethane. Then, an organic layer was fractionated, washed with 400 ml of water, and then dried with magnesium sulfate. The resulting solution was purified by column chromatography (filler: silica gel, eluent: dichloromethane/hexane) to obtain 1.02 g of compound (7-g).

In 20 ml of chloroform was dissolved 1.02 g of the compound (7-g), and then a dimethylformamide (5 ml) solution of 249 mg of N-bromosuccinimide (produced by Wako Pure Chemical Industries, Ltd.) was added, and the resulting mixture was stirred at a temperature of 5 to 10° C. for 6 hours. To the resulting solution were added 150 ml of water and 100 ml of dichloromethane. Then, an organic layer was fractionated, washed with 300 ml of water, and then dried with magnesium sulfate. The resulting solution was purified by column chromatography (filler: silica gel, eluent: hexane) to obtain 1.04 g of compound (7-h).

In 20 ml of toluene were dissolved 341 mg of the compound (7-h) and 110 mg of the compound (4-a) in Synthesis Example 4. To this solution were added 7 ml of water, 580 mg of potassium carbonate, 23 mg of tetrakis(triphenylphosphine)palladium(0) (produced by Tokyo Chemical Industry Co., Ltd.) and a drop of Aliquat 336 (produced by Aldrich Chemical Company, Inc.), and the resulting mixture was stirred under a nitrogen atmosphere at 100° C. for 8 hours. To the resulting solution was added 50 ml of methanol, and a solid fraction produced was collected by filtration and washed with methanol and acetone in this order. The obtained solid was dissolved in 300 ml of chloroform, and the resulting solution was passed through a silica gel short column (eluent: chloroform) and then concentrated to dryness, and washed with methanol and acetone in this order to obtain 320 mg of compound B-2. The compound B-2 had the weight average molecular weight of 593233, the number average molecular weight of 54251 and the polymerization degree n of 317.7. Further, the wavelength at an optical absorption edge of the compound B-2 was 661 nm, the band gap (Eg) was 1.87 eV, and the level of the highest occupied molecular orbital (HOMO) was −5.37 eV.

Synthesis Example 8

Compound B-3 was synthesized by the method illustrated in Scheme 8.

[Chem. 19]

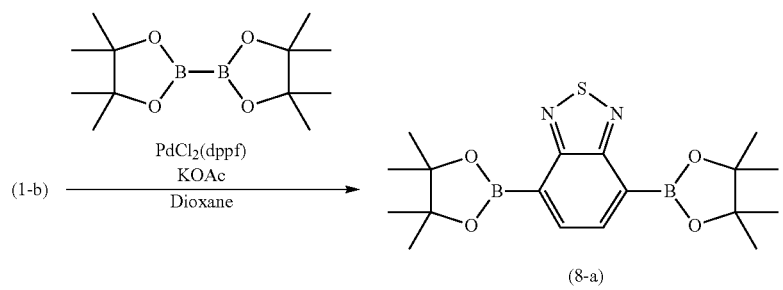

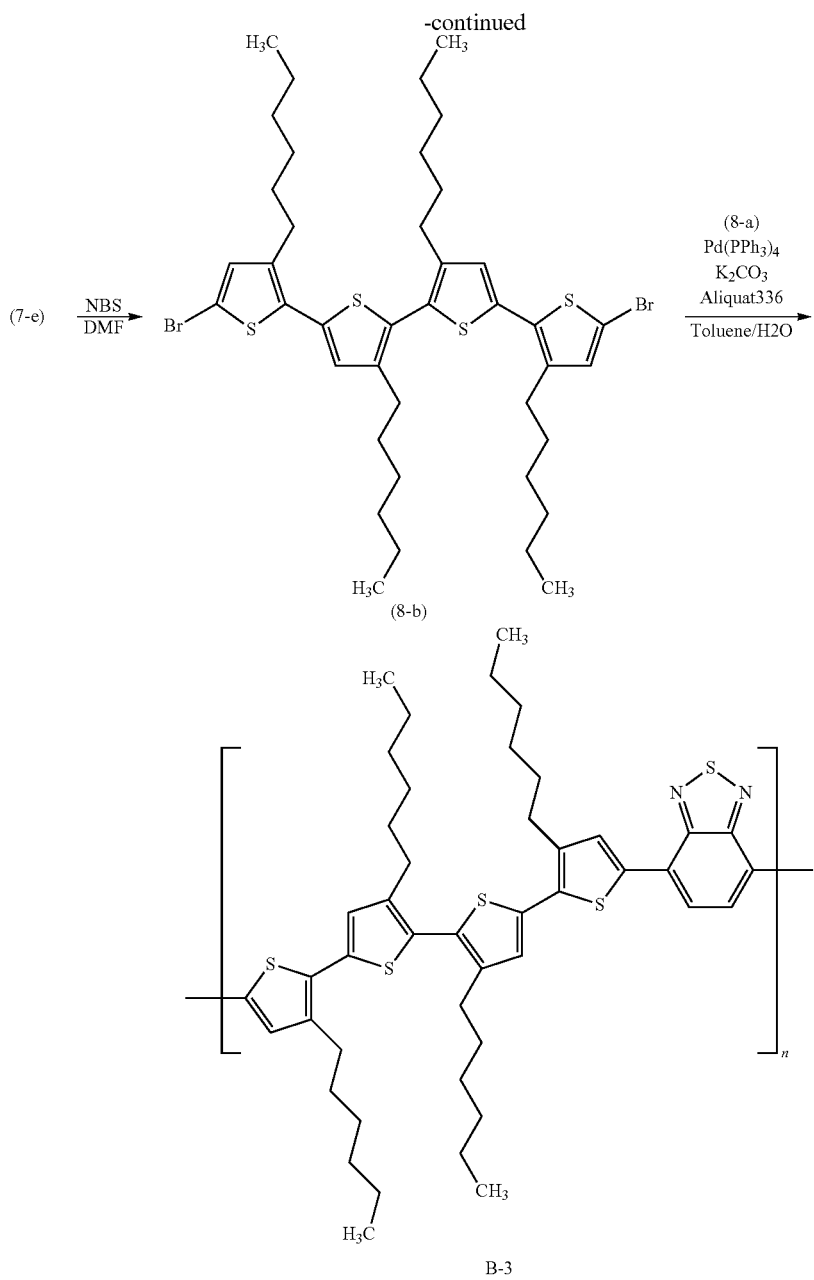

To 40 ml of 1,4-dioxane were added 2.0 g of the compound (1-b) in Synthesis Example 1 and 4.3 g of bis(pinacolato) diboron (produced by BASF Japan Ltd.). Under a nitrogen atmosphere, 4.0 g of potassium acetate (produced by Wako Pure Chemical Industries, Ltd.) and 1.0 g of bis(diphenylphosphino)ferrocene]dichloropalladium (produced by Aldrich Chemical Company, Inc.) were added and the resulting mixture was stirred at 80° C. for 8 hours. To the resulting solution were added 200 ml of water and 200 ml of ethyl acetate. Then, an organic layer was fractionated, washed with 400 ml of water, and then dried with magnesium sulfate. The resulting solution was purified by column chromatography (filler: silica gel, eluent: dichloromethane/ethyl acetate) to obtain 1.3 g of compound (8-a).

In 20 ml of chloroform was dissolved 520 mg of the compound (7-e) in Synthesis Example 7, and then a dimethylformamide (10 ml) solution of 280 mg of N-bromosuccinimide (produced by Wako Pure Chemical Industries, Ltd.) was added, and the resulting mixture was stirred at a temperature of 5 to 10° C. for 5 hours. To the resulting solution were added 150 ml of water and 100 ml of dichloromethane. Then, an organic layer was fractionated, washed with 200 ml of water, and then dried with magnesium sulfate. The resulting solution was purified by column chromatography (filler: silica gel, eluent: hexane) to obtain 610 mg of compound (8-b).

In 30 ml of toluene were dissolved 280 mg of the compound (8-a) and 596 mg of the compound (8-b). To this solution were added 10 ml of water, 1.99 g of potassium carbonate, 83 mg of tetrakis(triphenylphosphine)palladium (0) (produced by Tokyo Chemical Industry Co., Ltd.) and a drop of Aliquat 336 (produced by Aldrich Chemical Company, Inc.), and the resulting mixture was stirred under a nitrogen atmosphere at 100° C. for 20 hours. To the resulting solution was added 100 ml of methanol, and a solid fraction produced was collected by filtration and washed with methanol, water, acetone and hexane in this order. The obtained solid was dissolved in 200 ml of chloroform, and the resulting solution was passed through a silica gel short column (eluent: chloroform) and then concentrated to dryness, and washed with methanol, acetone and methanol in this order to obtain 480 mg of compound B-3. The compound B-3 had the weight average molecular weight of 29398, the number average molecular weight of 10916 and the polymerization degree n of 36.8. Further, the wavelength at an optical absorption edge of the compound B-3 was 684 nm, the band gap (Eg) was 1.81 eV, and the level of the highest occupied molecular orbital (HOMO) was −5.27 eV.

Synthesis Example 9

Compound A-7 was synthesized by the method illustrated in Scheme 9.

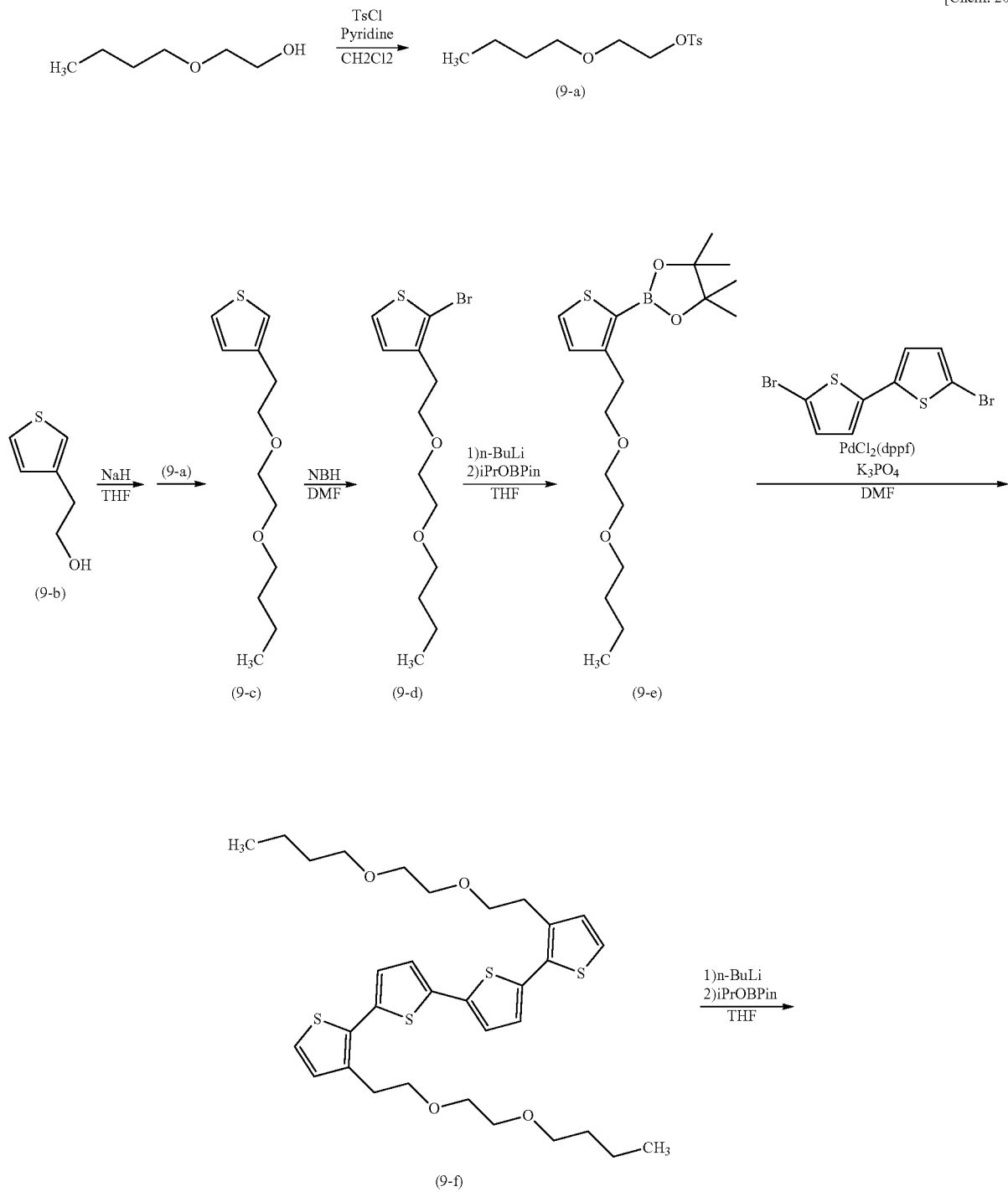

81
-continued
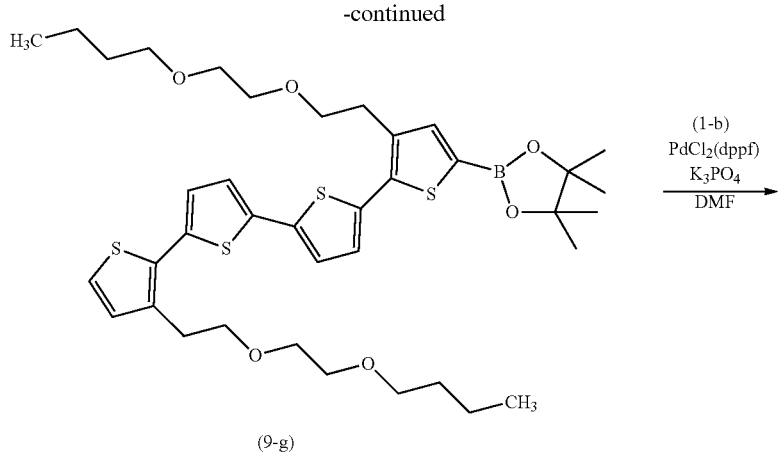
(9-g)
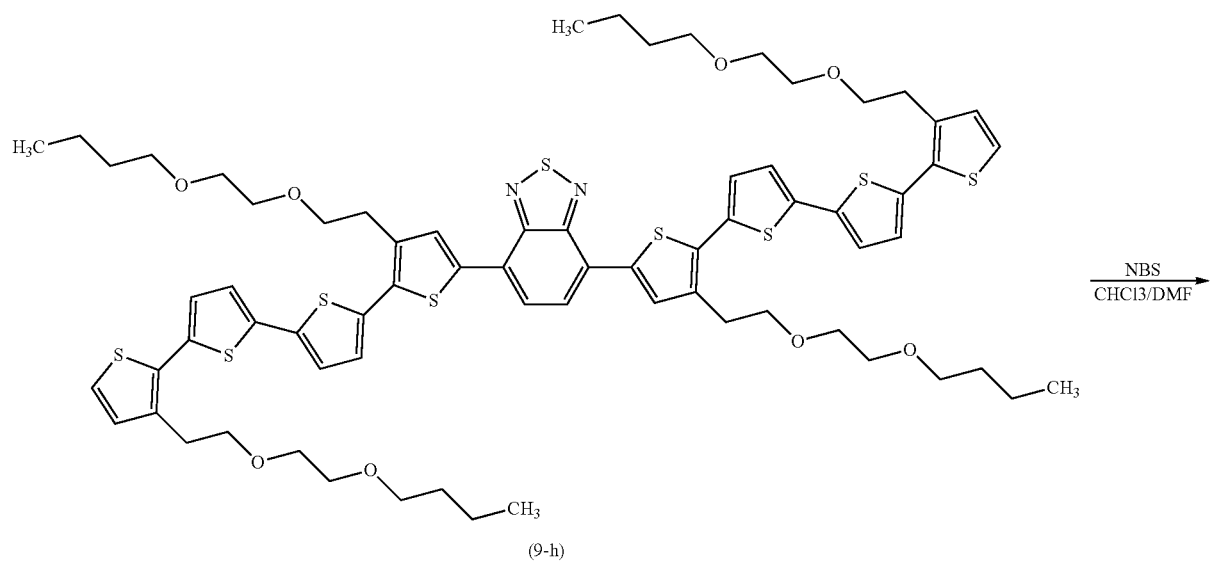
(9-h)
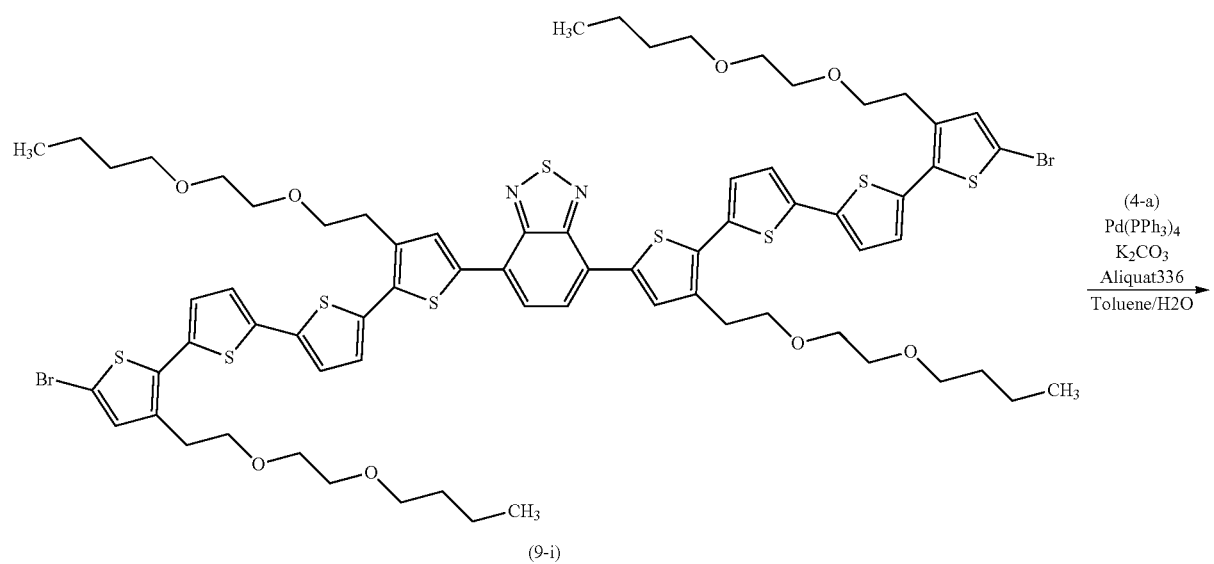
(9-i)

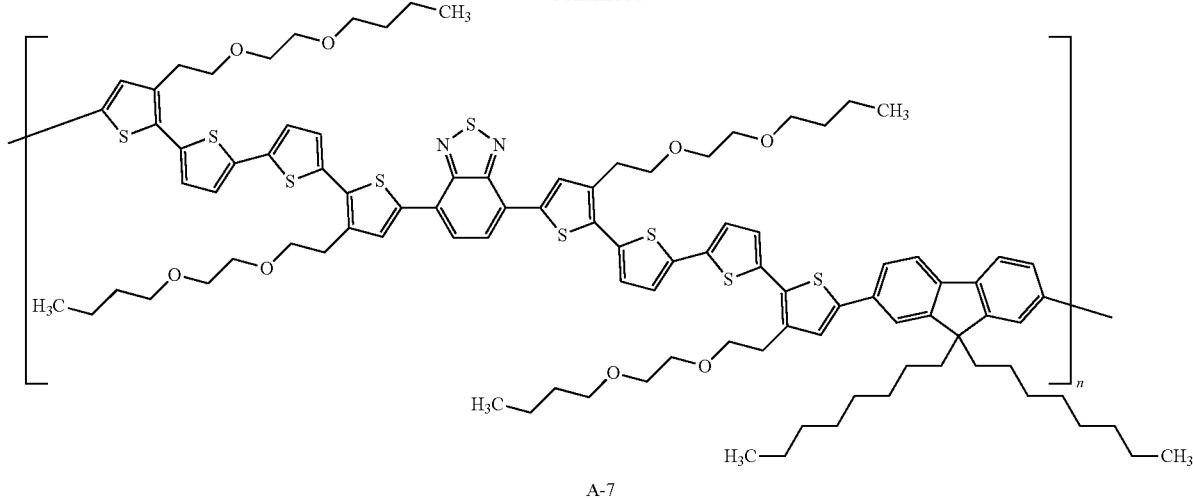

A-7

In 300 ml of dichloromethane were dissolved 20 ml of 2-buthoxyethanol (produced by Wako Pure Chemical Industries, Ltd.) and 29 ml of pyridine, and then 40 g of tosyl chloride was added at 5° C., and the resulting mixture was stirred at room temperature for 75 hours. To the resulting solution were added 500 ml of water and 200 ml of dichloromethane. Then, an organic layer was fractionated, washed with 2000 ml of water, and then dried with magnesium sulfate. The resulting solution was purified by column chromatography (filler: silica gel, eluent: dichloromethane) to obtain 21.7 g of compound (9-a).

A tetrahydrofuran (100 ml) solution of sodium hydride (87 mmol) was added to 8.54 g of compound (9-b) (produced by Wako Pure Chemical Industries, Ltd.) at 10° C., and the resulting mixture was stirred under a nitrogen atmosphere at 10° C. for 1 hour. Next, 21.7 g of the compound (9-a) was added and he resulting mixture was stirred at 80° C. for 12 hours. To the resulting solution were added 100 ml of water and 200 ml of hexane. Then, an organic layer was fractionated, washed with 400 ml of water, and then dried with magnesium sulfate. The resulting solution was purified by column chromatography (filler: silica gel, eluent: hexane/ethyl acetate) to obtain 10.74 g of compound (9-c).

In 50 ml of dimethylformamide was dissolved 10.74 g of the compound (9-c), and then a dimethylformamide (50 ml) solution of 8.37 g of N-bromosuccinimide (produced by Wako Pure Chemical Industries, Ltd.) was added, and the resulting mixture was stirred at room temperature for 12 hours. To the resulting solution were added 300 ml of water and 200 ml of hexane. Then, an organic layer was fractionated, washed with 400 ml of water, and then dried with magnesium sulfate. The resulting solution was purified by column chromatography (filler: silica gel, eluent: hexane/ethyl acetate) to obtain 13.1 g of compound (9-d).

In 150 ml of tetrahydrofuran (produced by Wako Pure Chemical Industries, Ltd.) was dissolved 13.1 g of the compound (9-d), and the resulting solution was cooled to −70° C. After adding 29 ml of a 1.6 M hexane solution of n-butyl lithium (produced by Wako Pure Chemical Industries, Ltd.), the temperature was raised to −50° C. and then lowered to −80° C. 11.3 ml of 2-isopropoxy-4,4,5,5-tetramethyl-1,3,2-dioxaborolane (produced by Wako Pure Chemical Industries, Ltd.) was added, and the temperature of the resulting mixture was raised to room temperature and the mixture was stirred under a nitrogen atmosphere for 2 days. To the resulting solution were added 200 ml of a 1 N aqueous solution of ammonium chloride and 200 ml of hexane. Then, an organic layer was fractionated, washed with 400 ml of water, and then dried with magnesium sulfate. The resulting solution was purified by column chromatography (filler: silica gel, eluent: dichloromethane/hexane) to obtain 13.3 g of compound (9-e).

To 170 ml of dimethylformamide were added 13.3 g of the compound (9-e) and 5.5 g of 5,5'-dibromo-2,2'-bithiophene (produced by Wako Pure Chemical Industries, Ltd.). Under a nitrogen atmosphere, 43.3 g of potassium phosphate (produced by Wako Pure Chemical Industries, Ltd.) and 690 mg of [bis(diphenylphosphino)ferrocene]dichloropalladium (produced by Aldrich Chemical Company, Inc.) were added and the resulting mixture was stirred at 100° C. for 8 hours. To the resulting solution were added 500 ml of water and 400 ml of hexane. Then, an organic layer was fractionated, washed with 500 ml of water, and then dried with magnesium sulfate. The resulting solution was purified by column chromatography (filler: silica gel, eluent: hexane/ethyl acetate) to obtain 3.91 g of compound (9-f).

In 40 ml of tetrahydrofuran (produced by Wako Pure Chemical Industries, Ltd.) was dissolved 3.91 g of the compound (9-f), and the resulting solution was cooled to −80° C. After adding 4.7 ml of a 1.6 M hexane solution of n-butyl lithium (produced by Wako Pure Chemical Industries, Ltd.), the temperature was raised to room temperature and then lowered to −80° C. again. 1.8 ml of 2-isopropoxy-4,4,5,5-tetramethyl-1,3,2-dioxaborolane (produced by Wako Pure Chemical Industries, Ltd.) was added, and the temperature of the resulting mixture was raised to room temperature and the mixture was stirred under a nitrogen atmosphere for 12 hours. To the resulting solution were added 200 ml of a 1 N aqueous solution of ammonium chloride and 200 ml of ethyl acetate. Then, an organic layer was fractionated, washed with 300 ml of water, and then dried with magnesium sulfate. The resulting solution was purified by column chromatography (filler: silica gel, eluent:hexane/ethyl acetate) to obtain 1.52 g of compound (9-g).

To 30 ml of dimethylformamide were added 1.52 g of the compound (9-g) and 300 mg of the compound (1-b) in Synthesis Example 1. Under a nitrogen atmosphere, 2.5 g of potassium phosphate (produced by Wako Pure Chemical Industries, Ltd.) and 41 mg of [bis(diphenylphosphino)ferrocene]dichloropalladium (produced by Aldrich Chemical Company, Inc.) were added and the resulting mixture was stirred at 100° C. for 7 hours. To the resulting solution was added 100 ml of water to obtain a solid fraction. The obtained solid fraction was collected by filtration and washed with water and then with methanol. The obtained solid fraction was purified by column chromatography (filler: silica gel, eluent: dichloromethane/ethyl acetate) to obtain 813 mg of compound (9-h).

In 20 ml of chloroform was dissolved 813 mg of the compound (9-h), and then a dimethylformamide (5 ml) solution of 211 mg of N-bromosuccinimide (produced by Wako Pure Chemical Industries, Ltd.) was added, and the resulting mixture was stirred at 5° C. for 7 hours. To the resulting solution were added 200 ml of water and 100 ml of dichloromethane. Then, an organic layer was fractionated, washed with 200 ml of water, and then dried with magnesium sulfate. The resulting solution was purified by column chromatography (filler: silica gel, eluent: dichloromethane/ethyl acetate) to obtain 730 mg of compound (9-i). The $^1$H-NMR measurement of the compound (9-i) is shown.

$^1$H-NMR (CDCl$_3$, ppm): 8.04 (s, 2H), 7.84 (s, 2H), 7.21-7.01 (m, 10H), 3.85 (t, 4H), 3.74-3.60 (m, 20H), 3.47 (t, 8H), 3.19 (t, 4H), 3.03 (t, 4H), 1.61-1.51 (m, 8H), 1.44-1.26 (m, 8H), 0.91 (m, 12H)

In 10 ml of toluene were dissolved 101 mg of the compound (9-i) and 29 mg of the compound (4-a) in Synthesis Example 4. To this solution were added 3 ml of water, 180 mg of potassium carbonate, 7.6 mg of tetrakis(triphenylphosphine)palladium(0) (produced by Tokyo Chemical Industry Co., Ltd.) and a drop of Aliquat 336 (produced by Aldrich Chemical Company, Inc.), and the resulting mixture was stirred under a nitrogen atmosphere at 100° C. for 16 hours. To the resulting solution were added concentrated hydrochloric acid/methanol (10 ml/200 ml), and a solid fraction produced was collected by filtration and washed with methanol, acetone, water and acetone in this order. The obtained solid was subjected to Soxhlet cleaning with acetone for 3 hours and then dissolved in chloroform. The resulting solution was concentrated to dryness, and washed with methanol to obtain 104 mg of compound A-8. The compound A-8 had the weight average molecular weight of 65060, the number average molecular weight of 15961 and the polymerization degree n of 37.3. Further, the wavelength at an optical absorption edge of the compound B-3 was 720 nm, the band gap (Eg) was 1.72 eV, and the level of the highest occupied molecular orbital (HOMO) was −5.00 eV.

Synthesis Example 10

Compound A-8 was synthesized by the method illustrated in Scheme 10.

[Chem. 21]

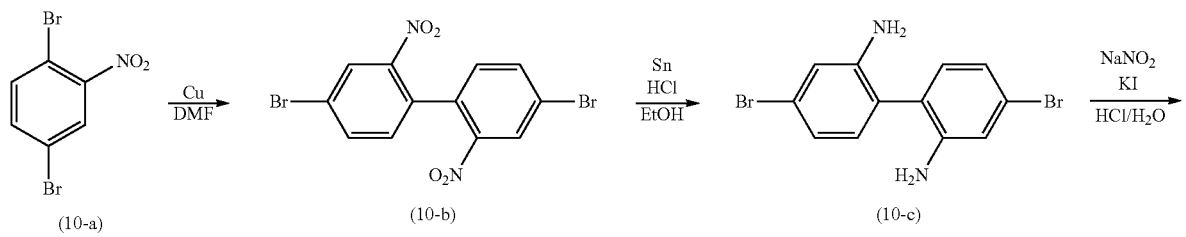

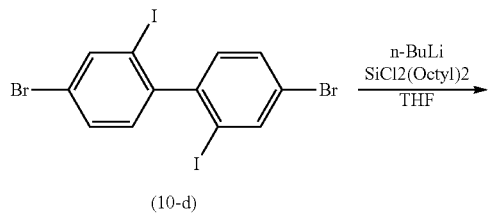

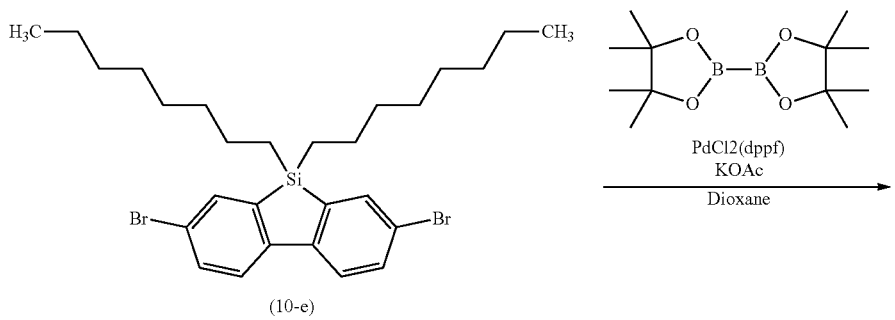

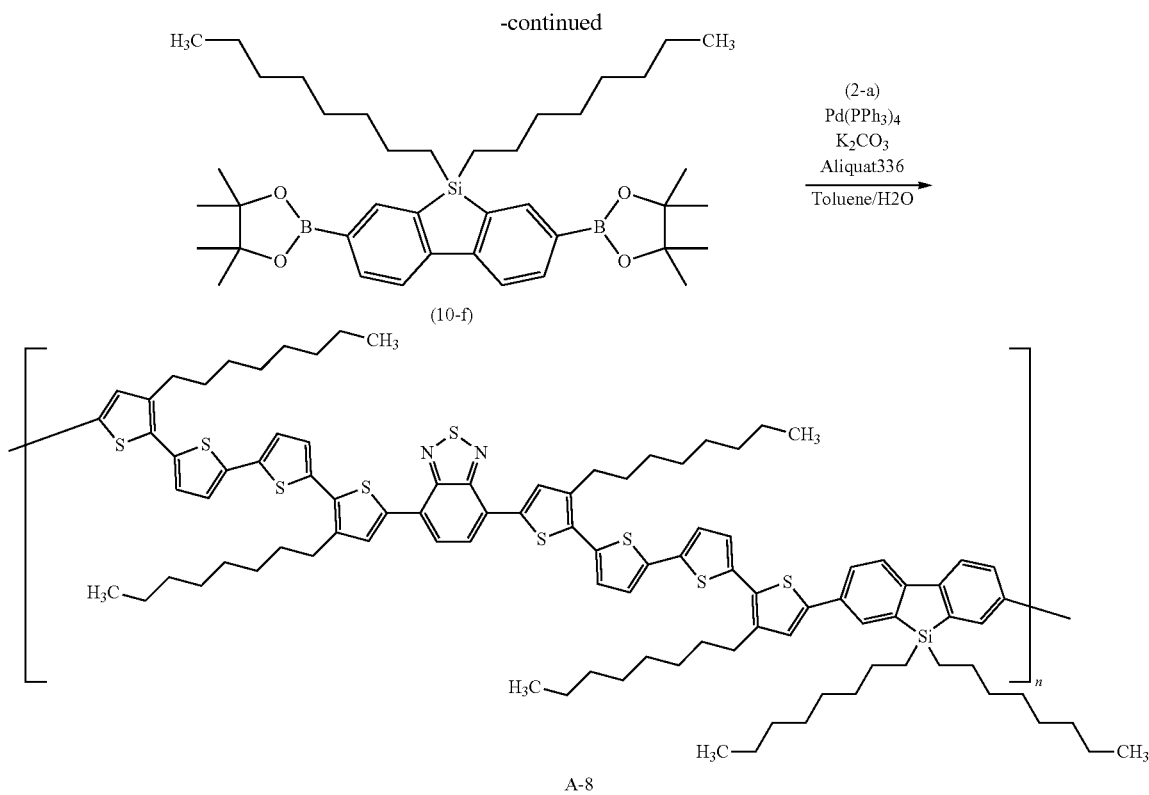

To 230 ml of dimethylformamide were added 50.25 g of compound (10-a) (produced by Wako Pure Chemical Industries, Ltd.) and 25 g of copper powder (produced by Wako Pure Chemical Industries, Ltd.), and the resulting mixture was stirred under a nitrogen atmosphere at 130° C. for 7 hours. The solvent was distilled off under reduced pressure and then 500 ml of toluene was added, and the resulting mixture was filtrated with sellite, and a filtrate was washed with 400 ml of water and 200 ml of an aqueous solution of sodium hydrogen carbonate in this order and then dried with magnesium sulfate. After distilling off the solvent from the resulting solution, the solution was washed with 300 ml of isopropanol to obtain 26 g of compound (10-b).

To 320 ml of ethanol was added 26 g of the compound (10-b), and then 180 ml of 36% hydrochloric acid and 31 g of tin powder (produced by Wako Pure Chemical Industries, Ltd.) were added and the resulting mixture was stirred under a nitrogen atmosphere at 100° C. for 4 hours. The resulting solution was added to 800 ml of water, and to this, an aqueous solution of sodium hydroxide was added to adjust a pH to about 10. A precipitation produced was collected by filtration, dissolved in 1000 ml of chloroform, washed with 1000 ml of water, and then dried with magnesium sulfate. The solvent was distilled off from the resulting solution to obtain 21.37 g of compound (10-c).

To 36% hydrochloric acid/water (75 ml/85 ml) was added 21.3 g of the compound (10-c), and to this, an aqueous $NaNO_2$ solution ($NaNO_2$ 10.7 g/water 55 ml) was added dropwise at 5° C. The resulting mixture was stirred at 5° C. for 30 minutes, and then an aqueous KI solution (KI 104 g/water 200 ml) was added dropwise and the resulting mixture was stirred at 5° C. for 1 hour, at room temperature for 1 hour and at 60° C. for 3 hours. A solid fraction produced was collected by filtration and purified by column chromatography (filler: silica gel, eluent: hexane) to obtain 4.27 g of compound (10-d).

In 85 ml of tetrahydrofuran (produced by Wako Pure Chemical Industries, Ltd.) was dissolved 4.27 g of the compound (10-d), and the resulting solution was cooled to −80° C. After adding 19 ml of a 1.6 M hexane solution of n-butyl lithium (produced by Wako Pure Chemical Industries, Ltd.) over 1 hour, the resulting mixture was stirred under a nitrogen atmosphere at −80° C. for 30 minutes. 5.2 ml of dichlorodioctylsilane (produced by Wako Pure Chemical Industries, Ltd.) was added, and the temperature of the resulting mixture was raised to room temperature and the mixture was stirred under a nitrogen atmosphere for one day. To the resulting solution was added 50 ml of water and the solvent was distilled off. After adding 150 ml of diethyl ether, an organic layer was fractionated, washed with 400 ml of water, and then dried with magnesium sulfate. The resulting solution was purified by column chromatography (filler:silica gel, eluent: hexane) to obtain 2.49 g of compound (10-e).

To 21 ml of 1,4-dioxane were added 2.49 g of the compound (10-e) and 2.58 g of bis(pinacolato)diboron (produced by BASF Japan Ltd.). Under a nitrogen atmosphere, 2.6 g of potassium acetate (produced by Wako Pure Chemical Industries, Ltd.) and 648 mg of bis(diphenylphosphino)ferrocene] dichloropalladium (produced by Aldrich Chemical Company, Inc.) were added and the resulting mixture was stirred at 80° C. for 5.5 hours. To the resulting solution were added 200 ml of water and 200 ml of diethyl ether. Then, an organic layer was fractionated, washed with 300 ml of water, and then dried with magnesium sulfate. The resulting solution was purified by column chromatography (filler: Florisil, eluent: hexane/ethyl acetate) to obtain 2.6 g of compound (10-f).

In 10 ml of toluene were dissolved 47 mg of the compound (10-f) and 100 mg of the compound (2-a) in Synthesis Example 2. To this solution were added 3 ml of water, 200 mg of potassium carbonate, 8.2 mg of tetrakis(triphenylphosphine)palladium(0) (produced by Tokyo Chemical Industry Co., Ltd.) and a drop of Aliquat 336 (produced by Aldrich Chemical Company, Inc.), and the resulting mixture was stirred under a nitrogen atmosphere at 100° C. for 7 hours. Next, five drops of bromobenzene (produced by Tokyo Chemical Industry Co., Ltd.) was added and the resulting mixture was stirred at 100° C. for 1 hour, and then 10 mg of phenylboronic acid (produced by Tokyo Chemical Industry Co., Ltd.) was added and the resulting mixture was stirred at 100° C. for 1 hour. To the resulting solution was added 100 ml of methanol, and a solid fraction produced was collected by filtration and washed with methanol, water and acetone in this order. The obtained solid was dissolved in 100 ml of chloroform, and the resulting solution was passed through a silica gel short column (eluent: chloroform) and then concentrated to dryness, and washed with hot acetone and methanol in this order to obtain 100 mg of compound A-8. The compound A-8 had the weight average molecular weight of 38843, the number average molecular weight of 22526 and the polymerization degree n of 23.6. Further, the wavelength at an optical absorption edge of the compound A-8 was 718 nm, the band gap (Eg) was 1.73 eV, and the level of the highest occupied molecular orbital (HOMO) was −5.13 eV.

Various properties (wavelength at an optical absorption edge, band gap (Eg), level of highest occupied molecular orbital (HOMO)) of the compounds A-1 to A-8, B-2 to B-3 and compound B-1 described later are shown in Table 1.

TABLE 1

| compound | optical absorption edge nm | Eg eV | HOMO eV |
| --- | --- | --- | --- |
| A-1 | 727 | 1.71 | −4.90 |
| A-2 | 720 | 1.72 | −5.00 |
| A-3 | 720 | 1.72 | −5.03 |
| A-4 | 721 | 1.72 | −5.14 |
| A-5 | 733 | 1.69 | −4.91 |
| A-6 | 716 | 1.73 | −5.21 |
| A-7 | 720 | 1.72 | −5.00 |
| A-8 | 718 | 1.73 | −5.13 |
| B-1 | 650 | 1.90 | −5.52 |
| B-2 | 661 | 1.87 | −5.37 |
| B-3 | 684 | 1.81 | −5.27 |

Example 1

To 0.25 ml of chlorobenzene contained in a sample tube were added 1 mg of the A-1 and 4 mg of $PC_{70}BM$ (produced by SCIENCE LABORATORIES, Inc.), and the resulting mixture was irradiated with ultrasonic waves for 30 minutes in an ultrasonic washing machine (US-2 (trade name) manufactured by Iuchi Seieido Co., Ltd., output 120 W) to obtain solution A.

A glass substrate on which an ITO transparent conductive layer, which would serve as a positive electrode, had been deposited in a thickness of 120 nm by sputtering was cut into a size of 38 mm×46 mm. Then, the ITO was patterned into a rectangular shape of 38 mm×13 mm in size by photolithography. The resulting substrate was ultrasonically washed for 10 minutes with an alkaline cleaning solution ("Semico Clean" EL56 (trade name) produced by Furuuchi Chemical Corp.) and then washed with ultrapure water. The substrate was subjected to UV/ozone treatment for 30 minutes and then an aqueous PEDOT:PSS solution (containing 0.8% by weight of PEDOT and 0.5% by weight of PPS), which would serve as a hole transport layer, was applied onto the substrate by spin coating to form a film in a thickness of 60 nm. After drying by heating at 200° C. for 5 minutes using a hot plate, the solution A was added dropwise to the PEDOT:PSS layer and an organic semiconductor layer of 100 nm in thickness was formed by spin coating. Thereafter, the substrate provided with the organic semiconductor layer and a mask for a cathode were placed in vacuum deposition equipment. The gas in the equipment was exhausted to a degree of vacuum of $1 \times 10^{-3}$ Pa or less again, and then an aluminum layer, which would serve as a negative electrode, was vapor-deposited in a thickness of 80 nm by resistive heating. As described above, a photovoltaic device was prepared in which each part where a striped ITO layer crossed with a striped aluminum layer had an area of 5 mm×5 mm.

The positive and the negative electrodes of the photovoltaic device thus prepared were connected to a picoammeter/voltage source 4140B manufactured by Hewlett-Packard Japan Ltd. While quasi solar light (manufactured by Yamashita Denso Corp., simplified type solar simulator YSS-E40, spectral shape: AM 1.5, Intensity: 100 mW/cm$^2$) was applied to the device from the ITO layer side in the air, the electric current value was measured when an applied voltage was changed from −1 V to +2 V. At this time, the short-circuit current density (i.e. the value of a current density at an applied voltage of 0 V) was 6.37 mA/cm$^2$, the open-circuit voltage (i.e. the value of a voltage applied when the current density became 0) was 0.914 V and the fill factor (FF) was 0.313. The photoelectric conversion efficiency calculated from those values was 1.82%. The fill factor and the photoelectric conversion efficiency were calculated by the following formulae.

Fill factor=JVmax/(Short-circuit current density× open-circuit voltage)

In the above formula, the JVmax is the value of the product of the current density and the applied voltage at the point where the product of the current density and the applied voltage becomes maximum in the applied voltage range between 0 V and the open-circuit voltage value.)

Photoelectric conversion efficiency=[(Short-circuit current density×open-circuit voltage×fill factor)/ quasi solar light intensity (mW/cm$^2$)]×100(%)

The fill factors and the photoelectric conversion efficiencies in the following Examples and Comparative Examples were all calculated by the above formulae.

Example 2

A photovoltaic device was prepared in the same manner as in Example 1 except for using the A-3 in place of the A-1, and the current/voltage characteristics were measured. At this time, the short-circuit current density was 6.12 mA/cm$^2$, the open-circuit voltage was 0.810 V and the fill factor (FF) was 0.346. The photoelectric conversion efficiency calculated from those values was 1.72%.

Example 3

A photovoltaic device was prepared in the same manner as in Example 1 except for using the A-4 in place of the A-1, and the current/voltage characteristics were measured. At this time, the short-circuit current density was 7.71 mA/cm$^2$, the open-circuit voltage was 0.842 V and the fill factor (FF) was 0.418. The photoelectric conversion efficiency calculated from those values was 2.72%.

Comparative Example 1

A photovoltaic device was prepared in the same manner as in Example 1 except for using the following B-1 (weight average molecular weight: 2630, number average molecular weight: 1604, polymerization degree n: 3.8) in place of the A-1, and the current/voltage characteristics were measured. At this time, the short-circuit current density was 3.57 mA/cm², the open-circuit voltage was 0.900 V and the fill factor (FF) was 0.280. The photoelectric conversion efficiency calculated from those values was 0.90%.

[Chem. 22]

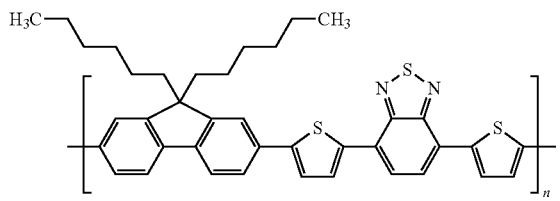

B-1

Comparative Example 2

A photovoltaic device was prepared in the same manner as in Example 1 except for using the B-2 in place of the A-1, and the current/voltage characteristics were measured. At this time, the short-circuit current density was 4.52 mA/cm², the open-circuit voltage was 0.920 V and the fill factor (FF) was 0.282. The photoelectric conversion efficiency calculated from those values was 1.17%.

Comparative Example 3

A photovoltaic device was prepared in the same manner as in Example 1 except for using the B-3 in place of the A-1, and the current/voltage characteristics were measured. At this time, the short-circuit current density was 4.58 mA/cm², the open-circuit voltage was 0.820 V and the fill factor (FF) was 0.266. The photoelectric conversion efficiency calculated from those values was 1.00%.

Example 4

A photovoltaic device was prepared in the same manner as in Example 3 except for using a mixed solution (0.2475 ml/0.0025 ml) of chlorobenzene/benzotrifluoride (trifluoromethylbenzene) in place of 0.25 ml of chlorobenzene, and the current/voltage characteristics were measured. At this time, the short-circuit current density was 7.84 mA/cm², the open-circuit voltage was 0.870 V and the fill factor (FF) was 0.438. The photoelectric conversion efficiency calculated from those values was 2.99%.

Example 5

A photovoltaic device was prepared in the same manner as in Example 4 except for vapor-depositing lithium fluoride in a thickness of 0.1 nm prior to vapor deposition of an aluminum layer to be a negative electrode, and the current/voltage characteristics were measured. At this time, the short-circuit current density was 8.44 mA/cm², the open-circuit voltage was 0.870 V and the fill factor (FF) was 0.430. The photoelectric conversion efficiency calculated from those values was 3.16%.

Example 6

A photovoltaic device was prepared in the same manner as in Example 5 except for using a mixed solution (0.0834 ml/0.3333 ml) of chlorobenzene/chloroform in place of the mixed solution (0.2475 ml/0.0025 ml) of chlorobenzene/benzotrifluoride (trifluoromethylbenzene), and the current/voltage characteristics were measured. At this time, the short-circuit current density was 8.72 mA/cm², the open-circuit voltage was 0.860 V and the fill factor (FF) was 0.466. The photoelectric conversion efficiency calculated from those values was 3.49%.

Example 7

A photovoltaic device was prepared in the same manner as in Example 1 except for using the A-6 in place of the A-1, and the current/voltage characteristics were measured. At this time, the short-circuit current density was 6.13 mA/cm², the open-circuit voltage was 0.910 V and the fill factor (FF) was 0.360. The photoelectric conversion efficiency calculated from those values was 2.00%.

Example 8

A photovoltaic device was prepared in the same manner as in Example 1 except for using the A-7 in place of the A-1, and the current/voltage characteristics were measured. At this time, the short-circuit current density was 7.54 mA/cm², the open-circuit voltage was 0.810 V and the fill factor (FF) was 0.400. The photoelectric conversion efficiency calculated from those values was 2.44%.

Example 9

A photovoltaic device was prepared in the same manner as in Example 1 except for using the A-8 in place of the A-1, and the current/voltage characteristics were measured. At this time, the short-circuit current density was 6.40 mA/cm², the open-circuit voltage was 0.859 V and the fill factor (FF) was 0.413. The photoelectric conversion efficiency calculated from those values was 2.27%.

Example 10

A photovoltaic device was prepared in the same manner as in Example 6 except for using a mixed solution (0.0825 ml/0.33 ml/0.0042 ml) of chlorobenzene/chloroform/benzotrifluoride(trifluoromethylbenzene) in place of the mixed solution (0.0834 ml/0.3333 ml) of chlorobenzene/chloroform, and the current/voltage characteristics were measured. At this time, the short-circuit current density was 8.50 mA/cm², the open-circuit voltage was 0.880 V and the fill factor (FF) was 0.490. The photoelectric conversion efficiency calculated from those values was 3.67%.

Example 11

A photovoltaic device was prepared in the same manner as in Example 6 except for forming a benzotrifluoride(trifluoromethylbenzene) layer on a PEDOT:PSS layer by a spin coating method before forming the organic semiconductor layer, and the current/voltage characteristics were measured. At this time, the short-circuit current density was 8.30 mA/cm², the open-circuit voltage was 0.890 V and the fill factor (FF) was 0.500. The photoelectric conversion efficiency calculated from those values was 3.69%.

The results of Examples 1 to 11 and Comparative Examples 1 to 3 are collectively shown in Table 2.

TABLE 2

| | compound | solvent | LiF | PEDOT:PSS pretreatment | Isc mA/cm$^2$ | Voc V | FF | η % |
|---|---|---|---|---|---|---|---|---|
| Example 1 | A-1 | chlorobenzene | none | none | 6.37 | 0.914 | 0.313 | 1.82 |
| Example 2 | A-3 | chlorobenzene | none | none | 6.12 | 0.810 | 0.346 | 1.72 |
| Example 3 | A-4 | chlorobenzene | none | none | 7.71 | 0.842 | 0.418 | 2.72 |
| Example 4 | A-4 | chlorobenzene/benzotrifluoride | none | none | 7.84 | 0.870 | 0.438 | 2.99 |
| Example 5 | A-4 | chlorobenzene/benzotrifluoride | 0.1 nm | none | 8.44 | 0.870 | 0.430 | 3.16 |
| Example 6 | A-4 | chlorobenzene/chloroform | 0.1 nm | none | 8.72 | 0.860 | 0.466 | 3.49 |
| Example 7 | A-6 | chlorobenzene | none | none | 6.13 | 0.910 | 0.360 | 2.00 |
| Example 8 | A-7 | chlorobenzene | none | none | 7.54 | 0.810 | 0.400 | 2.44 |
| Example 9 | A-8 | chlorobenzene | none | none | 6.40 | 0.859 | 0.413 | 2.27 |
| Comparative Example 1 | B-1 | chlorobenzene | none | none | 3.57 | 0.900 | 0.280 | 0.90 |
| Comparative Example 2 | B-2 | chlorobenzene | none | none | 4.52 | 0.920 | 0.282 | 1.17 |
| Comparative Example 3 | B-3 | chlorobenzene | none | none | 4.58 | 0.820 | 0.266 | 1.00 |
| Example 10 | A-4 | chlorobenzene/chloroform/benzotrifluoride | 0.1 nm | none | 8.50 | 0.880 | 0.490 | 3.67 |
| Example 11 | A-4 | chlorobenzene/chloroform | 0.1 nm | benzotrifluoride | 8.30 | 0.890 | 0.500 | 3.69 |

INDUSTRIAL APPLICABILITY

Photovoltaic devices using electron donating organic materials can be applied to various types of photoelectric conversion devices using a photoelectrically converting function, an optically rectifying function, and the like. The devices are useful for, for example, photoelectric cells (such as solar cells), electronic devices (such as photosensors, optical switches, and phototransistor), and optical record material (such as optical memory).

The invention claimed is:

1. An electron donating organic material comprising a benzothiadiazole compound comprising (a) a benzothiadiazole skeleton and (b) an oligothiophene skeleton, and having a band gap (Eg) of 1.8 eV or less, and a level of highest occupied molecular orbital (HOMO) of −4.8 eV or less, wherein said benzothiadiazole compound is formed by covalently combining the benzothiadiazole skeleton and the oligothiophene skeleton alternately, a proportion between the benzothiadiazole skeleton and the oligothiophene skeleton is 1:1 to 1:2 however, excluding 1:1, and the number of thiophene rings contained in an oligothiophene skeleton is 3 or more and 12 or less.

2. The material according to claim 1, wherein the benzothiadiazole skeleton of said benzothiadiazole compound is 2,1,3-benzothiadiazole-4,7-diyl and the oligothiophene skeleton is oligo(thiophene-2,5-diyl).

3. The material according to claim 2, wherein said benzothiadiazole compound has a structure represented by the formula (1):

[Chem. 1]

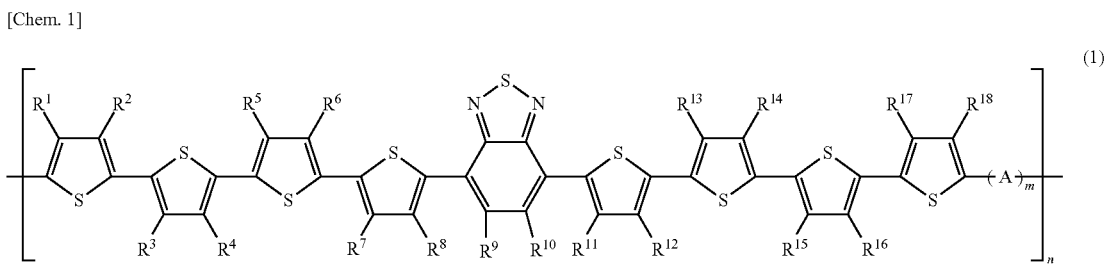

in which $R^1$ to $R^{18}$ may be the same or different from each other and are each selected from the group consisting of hydrogen, an alkyl group, an alkoxy group, an aryl group, a heteroaryl group and halogen, A represents a divalent arylene group having a six-membered ring structure or a divalent heteroarylene group having a six-membered ring structure, m is 0 or 1, and n is within a range of 1 to 1000.

4. A material for photovoltaic devices comprising an electron accepting organic material and the electron donating organic material according to claim 1.

5. The material according to claim 4, wherein the electron accepting organic material is a fullerene compound.

6. A photovoltaic device having at least a positive electrode and a negative electrode, wherein said photovoltaic device contains the material for photovoltaic devices according to claim 4 between the negative electrode and the positive electrode.

7. A photovoltaic device having at least a positive electrode and a negative electrode, wherein said photovoltaic device contains the material for photovoltaic devices according to claim 5 between the negative electrode and the positive electrode.

8. A material for photovoltaic devices comprising an electron accepting organic material and the electron donating organic material according to claim 2.

9. A material for photovoltaic devices comprising an electron accepting organic material and the electron donating organic material according to claim 3.

* * * * *